United States Patent
Miley et al.

(10) Patent No.: US 9,200,142 B2
(45) Date of Patent: *Dec. 1, 2015

(54) THERMOPLASTIC POLYMER COMPOSITION

(71) Applicant: MILLIKEN & COMPANY, Spartanburg, SC (US)

(72) Inventors: John W. Miley, Campobello, SC (US); Sanjeev K. Dey, Spartanburg, SC (US); Eduardo Torres, Boiling Springs, SC (US); Haihu Qin, Greer, SC (US)

(73) Assignee: MILLIKEN & COMPANY, Spartanburg, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/492,531

(22) Filed: Sep. 22, 2014

(65) Prior Publication Data

US 2015/0087757 A1    Mar. 26, 2015

Related U.S. Application Data

(60) Provisional application No. 61/881,212, filed on Sep. 23, 2013.

(51) Int. Cl.
| | |
|---|---|
| C08K 5/20 | (2006.01) |
| C08K 5/00 | (2006.01) |
| C07C 235/84 | (2006.01) |
| C07C 233/64 | (2006.01) |
| C07C 233/65 | (2006.01) |
| C07C 233/81 | (2006.01) |

(52) U.S. Cl.
CPC .................. *C08K 5/20* (2013.01); *C07C 233/64* (2013.01); *C07C 233/65* (2013.01); *C07C 233/81* (2013.01); *C07C 235/84* (2013.01); *C08K 5/0083* (2013.01); *C07C 2101/08* (2013.01)

(58) Field of Classification Search
CPC .......... C08K 5/20; C08K 5/00; C07C 235/84; C07C 233/64; C07C 233/65; C07C 233/81
USPC .......................... 524/89, 94, 204, 99; 562/457
See application file for complete search history.

(56) References Cited

U.S. PATENT DOCUMENTS

| | | | |
|---|---|---|---|
| 2,159,605 | A | 5/1939 | Schumacher et al. |
| 3,207,735 | A | 9/1965 | Wijga |
| 3,207,736 | A | 9/1965 | Wijga |
| 3,207,737 | A | 9/1965 | Wales |
| 3,207,738 | A | 9/1965 | Wijga |
| 3,207,739 | A | 9/1965 | Wales |
| 3,458,604 | A | 7/1969 | Palmer |
| 4,380,621 | A | 4/1983 | Nield et al. |
| 6,096,811 | A | 8/2000 | Amos et al. |
| 6,235,823 | B1 | 5/2001 | Ikeda et al. |
| 6,245,844 | B1 | 6/2001 | Kurian et al. |
| 6,787,067 | B2 | 9/2004 | Yukino et al. |
| 7,115,750 | B1 | 10/2006 | Kato et al. |
| 7,569,630 | B2 | 8/2009 | Ma et al. |
| 7,682,689 | B2 | 3/2010 | Sadamitsu et al. |
| 7,696,380 | B2 | 4/2010 | Kitagawa et al. |
| 7,723,413 | B2 | 5/2010 | Ishikawa et al. |
| 7,786,203 | B2 | 8/2010 | Hanssen et al. |
| 2007/0134296 | A1 | 6/2007 | Burgermeister et al. |

FOREIGN PATENT DOCUMENTS

| | | |
|---|---|---|
| CN | 103214736 A * | 7/2013 |
| DE | 2434953 A1 | 2/1975 |
| EP | 0 557 721 A2 | 9/1993 |
| EP | 1 266 932 A1 | 12/2002 |
| EP | 1 972 703 A1 | 9/2008 |
| EP | 2 392 458 A2 | 12/2011 |
| EP | 2392458 A2 * | 12/2011 |
| GB | 903015 A | 8/1962 |
| GB | 955304 A | 4/1964 |
| GB | 992470 A | 5/1965 |
| GB | 1001709 A | 8/1965 |
| JP | 6-155925 A | 6/1994 |
| JP | 10-25267 A | 1/1998 |
| JP | 2001-279191 A | 10/2001 |
| WO | WO 00/17265 A1 | 3/2000 |
| WO | WO 0017265 A1 * | 3/2000 |

(Continued)

OTHER PUBLICATIONS

Beck "Heterogeneous Nucleating Agents for Polypropylene Crystallization", Journal of Applied Polymer Science, vol. 11, pp. 673-685 (1967).*

Beck, H.N., "Heterogeneous Nucleating Agents for Polypropylene Crystallization", *Journal of Applied Polymer Science*, vol. 11 pp. 673-685, (1967).

Whittmann et al., "Epitaxial crystallization of monoclinic and orthorhombic polyethylene phases", *Polymer*, vol. 30 pp. 27-34, (1989), Butterworth & Co. (Publishers) Ltd.

Chemical Abstracts Service Database Accession No. 2013:1161532, Abstract of CN 103214736 A, "Amide based nucleating agent for preparation of isotactic polypropylene with beta crystal form, its preparation method and application," Guangzhou Chemistry Co., Ltd., Jul. 24, 2013.

Chemical Abstracts Service Database Accession No. 2005:104840, Abstract of Qiao et al., "Synthesis of a novel nucleating agent with thermotropic crystalline liquid behavior and its influence on the crystallization of polyethylene—(I). Synthesis and characterization of a novel nucleating agent with thermotropic liquid crystalline behavior," *Gaofenzi Cailiao Kexue Yu Gongcheng*, 2004, 20(6), 94-97.

(Continued)

*Primary Examiner* — Michael M Bernshteyn
(74) *Attorney, Agent, or Firm* — Robert M. Lanning

(57) ABSTRACT

The invention provides a compound conforming to the structure of Formula (C)

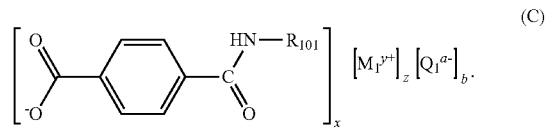

The invention also provides a thermoplastic polymer composition comprising a polyolefin polymer and a compound conforming to the structure of Formula (C) as a nucleating agent.

19 Claims, No Drawings

(56) References Cited

FOREIGN PATENT DOCUMENTS

| WO | WO 2010/144784 A1 | 12/2010 |
| WO | WO 2011/047108 A1 | 4/2011 |

OTHER PUBLICATIONS

SciFinder Search Reference Answer Set, Search for metal salts of terephthalic acid alkyl esters, Feb. 25, 2013.
Chemical Abstracts Service Database Accession No. 2013:230959, Abstract of IN 2011 MU 02218 A, "Stable formulation for calcium benzamidosalicylate," Genesen Labs Ltd., Feb. 8, 2013.
Chemical Abstracts Service Database Accession No. 1998:68515, Abstract of JP 10-25267 A, "Preparation of carboxylic acid polyvalent metal salts a developers for heat and pressure-sensitive recording materials," Mitsui Toatsu Chemicals, Inc., Jan. 27, 1998.
Chemical Abstracts Service Database Accession No. 1995:362238, Abstract of JP 6-155925 A, "Heat-sensitive recording material with improved color image storage stability," Mitsui Toatsu Chemicals, Jun. 3, 1994.
Chemical Abstracts Service Database Accession No. 1970:15789, Abstract of Koval'chuk, T.V., "UV-absorption spectra and determination of the calcium salt of p-benzamidosalicylic acid (bepascum)," *Farmatsevtichnii zhurnal,* 1969, 24(5), 62-6.
Chemical Abstracts Service CAS Registry No. 16777-78-9, Substance Detail and References, Mar. 13, 2015.
Chemical Abstracts Service CAS Registry No. 23745-26-8, Substance Detail and References, Mar. 13, 2015.
Chemical Abstracts Service CAS Registry No. 54056-74-5, Substance Detail and References, Mar. 13, 2015.
Chemical Abstracts Service CAS Registry No. 925413-00-9, Substance Detail and References, Mar. 13, 2015.
Chemical Abstracts Service CAS Registry No. 1154322-83-4, Substance Detail, Mar. 13, 2015.
Chemical Abstracts Service CAS Registry No. 1250130-73-4, Substance Detail, Mar. 13, 2015.
Chemical Abstracts Service CAS Registry No. 1395043-43-2, Substance Detail, Mar. 13, 2015.
PCT/US2014/056919 International Search Report, International Filing Date Sep. 23, 2014, 4 pages.
PCT/US2014/056919 Written Opinion of the International Searching Authority, International Filing Date Sep. 23, 2014, 7 pages.

\* cited by examiner

THERMOPLASTIC POLYMER COMPOSITION

CROSS REFERENCE TO RELATED APPLICATIONS

This application claims, pursuant to 35 U.S.C. §119(e)(1), priority to and the benefit of the filing date of U.S. Patent Application No. 61/881,212 filed on Sep. 23, 2013, which application is hereby incorporated by reference in its entirety.

TECHNICAL FIELD OF THE INVENTION

This application relates to nucleating agents for thermoplastic polymers, thermoplastic polymer compositions comprising such nucleating agents, articles made from such thermoplastic polymer compositions, and methods for making and molding such thermoplastic polymer compositions.

BACKGROUND

Several nucleating agents for thermoplastic polymers are known in the art. These nucleating agents generally function by forming nuclei or providing sites for the formation and/or growth of crystals in the thermoplastic polymer as it solidifies from a molten state. The nuclei or sites provided by the nucleating agent allow the crystals to form within the cooling polymer at a higher temperature and/or at a more rapid rate than the crystals will form in the virgin, non-nucleated thermoplastic polymer. These effects can then permit processing of a nucleated thermoplastic polymer composition at cycle times that are shorter than the virgin, non-nucleated thermoplastic polymer.

While polymer nucleating agents may function in a similar manner, not all nucleating agents are created equal. For example, a particular nucleating agent may be very effective at increasing the peak polymer recrystallization temperature of a thermoplastic polymer, but the rapid rate of crystallization induced by such a nucleating agent may cause inconsistent shrinkage of a molded part produced from a thermoplastic polymer composition containing the nucleating agent. Such a nucleating agent may also be ineffective in increasing the stiffness of the molded part to a desirable degree. Also, while nucleating agents for polyethylene polymers are known in the art, relatively few of these nucleating agents have been shown to improve the physical properties of the polyethylene polymer to any commercially significant degree.

Given the complicated interrelationship of these properties and the fact that many nucleating agents exhibit less-than-optimal behavior in at least one respect, a need remains for nucleating agents that are capable of producing thermoplastic polymer compositions exhibiting a more desirable combination of high peak polymer recrystallization temperature, tunable shrinkage, and high stiffness. Applicants believe that the nucleating agents and thermoplastic polymer compositions disclosed in the present application meet such a need.

BRIEF SUMMARY OF THE INVENTION

As noted above, the present application generally relates to nucleating agents, thermoplastic polymer compositions comprising such nucleating agents, articles (e.g., molded articles) made from such thermoplastic polymer compositions, and methods for making and molding such thermoplastic polymer compositions. The nucleating agents and thermoplastic polymer compositions according to the invention are believed to be particularly well-suited for the production of thermoplastic polymer articles (e.g., molded thermoplastic polymer articles) exhibiting a desirable combination of physical properties. In particular, articles produced using the nucleating agents and thermoplastic polymer compositions of the invention are believed to exhibit a desirable combination of a higher peak polymer recrystallization temperature and improved physical properties (e.g., tear strength) as compared to articles made from the non-nucleated thermoplastic polymer. Applicants believe that this combination of physical properties indicates that the nucleating agents and thermoplastic polymer compositions according to the invention are well-suited for use in the production of thermoplastic polymer articles.

In a first embodiment, the invention provides a thermoplastic polymer composition comprising:
(a) a polyolefin polymer; and
(b) a nucleating agent, the nucleating agent comprising a compound conforming to the structure of Formula (I)

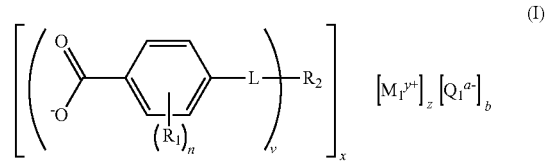

wherein $R_1$ is selected from the group consisting of hydroxy, halogens, alkyl groups, substituted alkyl groups, alkoxy groups, substituted alkoxy groups, aryl groups, and substituted aryl groups; n is zero or a positive integer from 1 to 4; L is a linking group comprising two or more atoms and at least one double bond between two atoms in the linking group; v is a positive integer from 1 to 3; $R_2$ is: (i) selected from the group consisting of alkyl groups, substituted alkyl groups, cycloalkyl groups, substituted cycloalkyl groups, aryl groups, substituted aryl groups, heteroaryl groups, and substituted heteroaryl groups when L is a divalent linking group and v is 1, (ii) selected from the group consisting of alkanediyl groups, substituted alkanediyl groups, cycloalkanediyl groups, substituted cycloalkanediyl groups, arenediyl groups, substituted arenediyl groups, heteroarenediyl groups, and substituted heteroarenediyl groups when L is a trivalent linking group and v is 1, (iii) selected from the group consisting of alkanediyl groups, substituted alkanediyl groups, cycloalkanediyl groups, substituted cycloalkanediyl groups, arenediyl groups, substituted arenediyl groups, heteroarenediyl groups, and substituted heteroarenediyl groups when L is a divalent linking group and v is 2, and (iv) selected from the group consisting of alkanetriyl groups, substituted alkanetriyl groups, cycloalkanetriyl groups, substituted cycloalkanetriyl groups, arenetriyl groups, substituted arenetriyl groups, heteroarenetriyl groups, and substituted heteroarenetriyl groups when L is a divalent linking group and v is 3; x is a positive integer; each $M_1$ is a metal cation; y is the valence of the cation; z is a positive integer; b is zero or a positive integer; when b is a positive integer, each $Q_1$ is a negatively-charged counterion and a is the valence of the negatively-charged counterion; and the values of v, x, y, z, a, and b satisfy the equation $(vx)+(ab)=yz$; wherein the cyclic portion of the cycloalkyl group or substituted cycloalkyl group comprises no more than two ring structures fused together when L is a divalent linking group, v is 1, and $R_2$ is a cycloalkyl group or a substituted cycloalkyl group.

In a second embodiment, the invention provides a compound conforming to the structure of Formula (C)

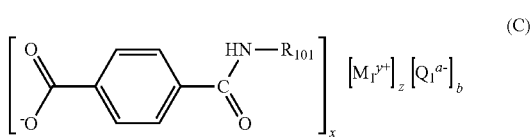
(C)

wherein $R_{101}$ is selected from the group consisting of a cyclopentyl group and moieties conforming to the structure of Formula (CI); Formula (CI) is

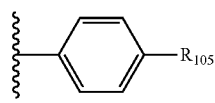
(CI)

$R_{105}$ is selected from the group consisting of hydrogen and halogens; x is a positive integer; each $M_1$ is a metal cation; y is the valence of the cation; z is a positive integer; b is zero or a positive integer; when b is a positive integer, each $Q_1$ is a negatively-charged counterion and a is the valence of the negatively-charged counterion; and the values of x, y, z, a, and b satisfy the equation x+(ab)=yz In a third embodiment, the invention provides a compound conforming to the structure of Formula (CX)

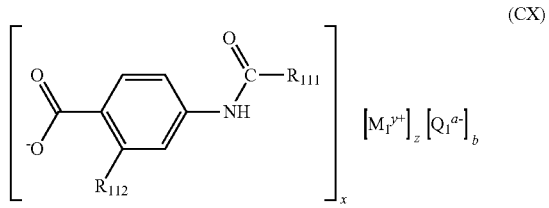
(CX)

wherein $R_{111}$ is selected from the group consisting of a cyclopentyl group and moieties conforming to the structure of Formula (CXI); $R_{112}$ is selected from the group consisting of hydrogen and hydroxy; Formula (CXI) is

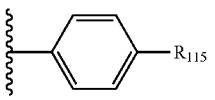
(CXI)

$R_{115}$ is selected from the group consisting of hydrogen, a halogen, methoxy, and phenyl; x is a positive integer; each $M_1$ is a metal cation; y is the valence of the cation; z is a positive integer; b is zero or a positive integer; when b is a positive integer, each $Q_1$ is a negatively-charged counterion and a is the valence of the negatively-charged counterion; and the values of x, y, z, a, and b satisfy the equation x+(ab)=yz; provided if $R_{115}$ is hydrogen, then $R_{112}$ is hydrogen, x is 1, $M_1$ is a lithium cation, y is 1, z is 1, and b is zero; and provided if $R_{115}$ is a methoxy group, then $R_{112}$ is a hydroxy group.

In a fourth embodiment, the invention provides a compound conforming to the structure of Formula (CXX)

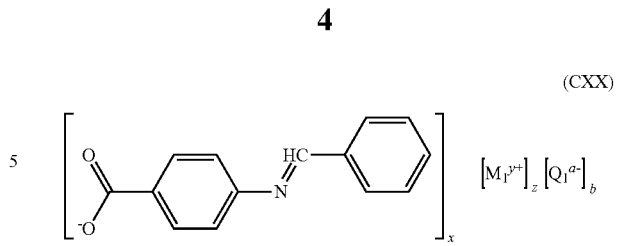
(CXX)

wherein x is a positive integer; each $M_1$ is a cation of a metal selected from the group consisting of alkali metals, alkaline earth metals, and zinc; y is the valence of the cation; z is a positive integer; b is zero or a positive integer; when b is a positive integer, each $Q_1$ is a negatively-charged counterion and a is the valence of the negatively-charged counterion; and the values of x, y, z, a, and b satisfy the equation x+(ab)=yz.

DETAILED DESCRIPTION OF THE INVENTION

The following definitions are provided to define several of the terms used throughout this application.

As used herein, the term "substituted alkyl groups" refers to univalent functional groups derived from substituted alkanes by removal of a hydrogen atom from a carbon atom of the alkane. In this definition, the term "substituted alkanes" refers to compounds derived from acyclic unbranched and branched hydrocarbons in which (1) one or more of the hydrogen atoms of the hydrocarbon is replaced with a non-hydrogen atom (e.g., a halogen atom) or a non-alkyl functional group (e.g., a hydroxy group, aryl group, or heteroaryl group) and/or (2) the carbon-carbon chain of the hydrocarbon is interrupted by an oxygen atom (as in an ether), a nitrogen atom (as in an amine), or a sulfur atom (as in a sulfide).

As used herein, the term "substituted cycloalkyl groups" refers to univalent functional groups derived from substituted cycloalkanes by removal of a hydrogen atom from a carbon atom of the cycloalkane. In this definition, the term "substituted cycloalkanes" refers to compounds derived from saturated monocyclic and polycyclic hydrocarbons (with or without side chains) in which (1) one or more of the hydrogen atoms of the hydrocarbon is replaced with a non-hydrogen atom (e.g., a halogen atom) or a non-alkyl functional group (e.g., a hydroxy group, aryl group, or heteroaryl group) and/or (2) the carbon-carbon chain of the hydrocarbon is interrupted by an oxygen atom, a nitrogen atom, or a sulfur atom.

As used herein, the term "substituted alkoxy groups" refers to univalent functional groups derived from substituted hydroxyalkanes by removal of a hydrogen atom from a hydroxy group. In this definition, the term "substituted hydroxyalkanes" refers to compounds having one or more hydroxy groups bonded to a substituted alkane, and the term "substituted alkane" is defined as it is above in the definition of substituted alkyl groups.

As used herein, the term "substituted aryl groups" refers to univalent functional groups derived from substituted arenes by removal of a hydrogen atom from a ring carbon atom. In this definition, the term "substituted arenes" refers to compounds derived from monocyclic and polycyclic aromatic hydrocarbons in which one or more of the hydrogen atoms of the hydrocarbon is replaced with a non-hydrogen atom (e.g., a halogen atom) or a non-alkyl functional group (e.g., a hydroxy group).

As used herein, the term "substituted heteroaryl groups" refers to univalent functional groups derived from substituted heteroarenes by removal of a hydrogen atom from a ring atom. In this definition, the term "substituted heteroarenes"

refers to compounds derived from monocyclic and polycyclic aromatic hydrocarbons in which (1) one or more of the hydrogen atoms of the hydrocarbon is replaced with a non-hydrogen atom (e.g., a halogen atom) or a non-alkyl functional group (e.g., a hydroxy group) and (2) at least one methine group (—C≡) of the hydrocarbon is replaced by a trivalent heteroatom and/or at least one vinylidene group (—CH═CH—) of the hydrocarbon is replaced by a divalent heteroatom.

As used herein, the term "alkanediyl groups" refers to divalent functional groups derived from alkanes by removal of two hydrogen atoms from the alkane. These hydrogen atoms can be removed from the same carbon atom on the alkane (as in ethane-1,1-diyl) or from different carbon atoms (as in ethane-1,2-diyl).

As used herein, the term "substituted alkanediyl groups" refers to divalent functional groups derived from substituted alkanes by removal of two hydrogen atoms from the alkane. These hydrogen atoms can be removed from the same carbon atom on the substituted alkane (as in 2-fluoroethane-1,1-diyl) or from different carbon atoms (as in 1-fluoroethane-1,2-diyl). In this definition, the term "substituted alkanes" has the same meaning as set forth above in the definition of substituted alkyl groups.

As used herein, the term "cycloalkanediyl groups" refers to divalent functional groups derived from cycloalkanes by removal of two hydrogen atoms from the cycloalkane. These hydrogen atoms can be removed from the same carbon atom on the cycloalkane or from different carbon atoms.

As used herein, the term "substituted cycloalkanediyl groups" refers to divalent functional groups derived from substituted cycloalkanes by removal of two hydrogen atoms from the alkane. In this definition, the term "substituted cycloalkanes" has the same meaning as set forth above in the definition of substituted cycloalkyl groups.

As used herein, the term "arenediyl groups" refers to divalent functional groups derived from arenes (monocyclic and polycyclic aromatic hydrocarbons) by removal of two hydrogen atoms from ring carbon atoms.

As used herein, the term "substituted arenediyl groups" refers to divalent functional groups derived from substituted arenes by removal of two hydrogen atoms from ring carbon atoms. In this definition, the term "substituted arenes" refers to compounds derived from monocyclic and polycyclic aromatic hydrocarbons in which one or more of the hydrogen atoms of the hydrocarbon is replaced with a non-hydrogen atom (e.g., a halogen atom) or a non-alkyl functional group (e.g., a hydroxy group).

As used herein, the term "heteroarenediyl groups" refers to divalent functional groups derived from heteroarenes by removal of two hydrogen atoms from ring atoms. In this definition, the term "heteroarenes" refers to compounds derived from monocyclic and polycyclic aromatic hydrocarbons in which at least one methine group (—C≡) of the hydrocarbon is replaced by a trivalent heteroatom and/or at least one vinylidene group (—CH═CH—) of the hydrocarbon is replaced by a divalent heteroatom.

As used herein, the term "substituted heteroarenediyl groups" refers to divalent functional groups derived from substituted heteroarenes by removal of two hydrogen atoms from ring atoms. In this definition, the term "substituted heteroarenes" has the same meaning as set forth above in the definition of substituted heteroaryl groups.

As used herein, the term "alkanetriyl groups" refers to trivalent functional groups derived from alkanes by removal of three hydrogen atoms from the alkane. These hydrogen atoms can be removed from the same carbon atom on the alkane or from different carbon atoms.

As used herein, the term "substituted alkanetriyl groups" refers to trivalent functional groups derived from substituted alkanes by removal of three hydrogen atoms from the alkane. These hydrogen atoms can be removed from the same carbon atom on the substituted alkane or from different carbon atoms. In this definition, the term "substituted alkanes" has the same meaning as set forth above in the definition of substituted alkyl groups.

As used herein, the term "cycloalkanetriyl groups" refers to trivalent functional groups derived from cycloalkanes by removal of three hydrogen atoms from the cycloalkane.

As used herein, the term "substituted cycloalkanetriyl groups" refers to trivalent functional groups derived from substituted cycloalkanes by removal of three hydrogen atoms from the alkane. In this definition, the term "substituted cycloalkanes" has the same meaning as set forth above in the definition of substituted cycloalkyl groups.

As used herein, the term "arenetriyl groups" refers to trivalent functional groups derived from arenes (monocyclic and polycyclic aromatic hydrocarbons) by removal of three hydrogen atoms from ring carbon atoms.

As used herein, the term "substituted arenetriyl groups" refers to trivalent functional groups derived from substituted arenes by removal of three hydrogen atoms from ring carbon atoms. In this definition, the term "substituted arenes" has the same meaning as set forth above in the definition of substituted arenediyl groups.

As used herein, the term "heteroarenetriyl groups" refers to trivalent functional groups derived from heteroarenes by removal of three hydrogen atoms from ring atoms. In this definition, the term "heteroarenes" has the same meaning as set forth above in the definition of heteroarenediyl groups.

As used herein, the term "substituted heteroarenetriyl groups" refers to trivalent functional groups derived from substituted heteroarenes by removal of three hydrogen atoms from ring atoms. In this definition, the term "substituted heteroarenes" has the same meaning as set forth above in the definition of substituted heteroaryl groups.

In a first embodiment, the invention provides a thermoplastic polymer composition comprising a thermoplastic polymer and a nucleating agent. The thermoplastic polymer of the thermoplastic polymer composition can be any suitable thermoplastic polymer. As utilized herein, the term "thermoplastic polymer" is used to refer to a polymeric material that will melt upon exposure to sufficient heat to form a flowable liquid and will return to a solidified state upon sufficient cooling. In their solidified state, such thermoplastic polymers exhibit either crystalline or semicrystalline morphology. Suitable thermoplastic polymers include, but are not limited to, polyolefins (e.g., polyethylenes, polypropylenes, polybutylenes, and any combinations thereof), polyamides (e.g., nylon), polyurethanes, polyesters (e.g., polyethylene terephthalate), and the like, as well as any combinations thereof. These thermoplastic polymers can be in the form of powder, fluff, flake, prill, or pellet made from freshly-produced polymer, polymer regrind, post-consumer waste, or post-industrial waste.

In certain embodiments, the thermoplastic polymer can be a polyolefin, such as a polypropylene, a polyethylene, a polybutylene, a poly(4-methyl-1-pentene), and a poly(vinyl cyclohexane). In a preferred embodiment, the thermoplastic polymer is a polyolefin selected from the group consisting of polypropylene homopolymers (e.g., atactic polypropylene, isotactic polypropylene, and syndiotactic polypropylene), polypropylene copolymers (e.g., polypropylene random copolymers), polypropylene impact copolymers, polyethylene, polyethylene copolymers, polybutylene, poly(4-methyl-1-pentene), and mixtures thereof. Suitable polypropylene copolymers include, but are not limited to, random copolymers made from the polymerization of propylene in the presence of a comonomer selected from the group consisting of ethylene, but-1-ene (i.e., 1-butene), and hex-1-ene (i.e., 1-hexene). In such polypropylene random copolymers, the comonomer can be present in any suitable amount, but typically is present in an amount of less than about 10 wt. % (e.g., about 1 to about 7 wt. %). Suitable polypropylene impact copolymers include, but are not limited to, those produced by the addition of a copolymer selected from the group consisting of ethylene-propylene rubber (EPR), ethylenepropylenediene monomer (EPDM), polyethylene, and plastomers to a polypropylene homopolymer or polypropylene random copolymer. In such polypropylene impact copolymers, the copolymer can be present in any suitable amount, but typically is present in an amount of from about 5 to about 25 wt. %.

In another preferred embodiment, the thermoplastic polymer can be a polyethylene. Suitable polyethylenes include, but are not limited to, low density polyethylene, linear low density polyethylene, medium density polyethylene, high density polyethylene, and combinations thereof. In certain preferred embodiments, the thermoplastic polymer is selected from the group consisting of linear low density polyethylene, high density polyethylene, and mixtures thereof. In another preferred embodiment, the thermoplastic polymer is a high density polyethylene.

The high density polyethylene polymers suitable for use in the invention generally have a density of greater than about 0.940 g/cm$^3$. There is no upper limit to the suitable density of the polymer, but high density polyethylene polymers typically have a density that is less than about 0.980 g/cm$^3$ (e.g., less than about 0.975 g/cm$^3$).

The high density polyethylene polymers suitable for use in the invention can be either homopolymers or copolymers of ethylene with one or more α-olefins. Suitable α-olefins include, but are not limited to, 1-butene, 1-hexene, 1-octene, 1-decene, and 4-methyl-1-pentene. The comonomer can be present in the copolymer in any suitable amount, such as an amount of about 5% by weight or less (e.g., about 3 mol. % or less). As will be understood by those of ordinary skill in the art, the amount of comonomer suitable for the copolymer is largely driven by the end use for the copolymer and the required or desired polymer properties dictated by that end use.

The high density polyethylene polymers suitable for use in the invention can be produced by any suitable process. For example, the polymers can be produced by a free radical process using very high pressures as described, for example, in U.S. Pat. No. 2,816,883 (Larchar et al.), but the polymers typically are produced in a "low pressure" catalytic process. In this context, the term "low pressure" is used to denote processes carried out at pressures less than 6.9 MPa (e.g., 1,000 psig), such as 1.4-6.9 MPa (200-1,000 psig). Examples of suitable low pressure catalytic processes include, but are not limited to, solution polymerization processes (i.e., processes in which the polymerization is performed using a solvent for the polymer), slurry polymerization processes (i.e., processes in which the polymerization is performed using a hydrocarbon liquid in which the polymer does not dissolve or swell), gas-phase polymerization processes (e.g., processes in which the polymerization is performed without the use of a liquid medium or diluent), or a staged reactor polymerization process. The suitable gas-phase polymerization processes also include the so-called "condensed mode" or "super-condensed mode" processes in which a liquid hydrocarbon is introduced into the fluidized-bed to increase the absorption of the heat producing during the polymerization process. In these condensed mode and super-condensed mode processes, the liquid hydrocarbon typically is condensed in the recycle stream and reused in the reactor. The staged reactor processes can utilize a combination of slurry process reactors (tanks or loops) that are connected in series, parallel, or a combination of series or parallel so that the catalyst (e.g., chromium catalyst) is exposed to more than one set of reaction conditions. Staged reactor processes can also be carried out by combining two loops in series, combining one or more tanks and loops in series, using multiple gas-phase reactors in series, or a loop-gas phase arrangement. Because of their ability to expose the catalyst to different sets of reactor conditions, staged reactor processes are often used to produce multimodal polymers, such as those discussed below. Suitable processes also include those in which a pre-polymerization step is performed. In this pre-polymerization step, the catalyst typically is exposed to the cocatalyst and ethylene under mild conditions in a smaller, separate reactor, and the polymerization reaction is allowed to proceed until the catalyst comprises a relatively small amount (e.g., about 5% to about 30% of the total weight) of the resulting composition. This pre-polymerized catalyst is then introduced to the large-scale reactor in which the polymerization is to be performed.

The high density polyethylene polymers suitable for use in the invention can be produced using any suitable catalyst or combination of catalysts. Suitable catalysts include transition metal catalysts, such as supported reduced molybdenum oxide, cobalt molybdate on alumina, chromium oxide, and transition metal halides. Chromium oxide catalysts typically are produced by impregnating a chromium compound onto a porous, high surface area oxide carrier, such as silica, and then calcining it in dry air at 500-900° C. This converts the chromium into a hexavalent surface chromate ester or dichromate ester. The chromium oxide catalysts can be used in conjunction with metal alkyl cocatalysts, such as alkyl boron, alkyl aluminum, alkyl zinc, and alkyl lithium. Supports for the chromium oxide include silica, silica-titania, silica-alumina, alumina, and aluminophosphates. Further examples of chromium oxide catalysts include those catalysts produced by depositing a lower valent organochromium compound, such as bis(arene) Cr$^0$, allyl Cr$^{2+}$ and Cr$^{3+}$, beta stabilized alkyls of Cr$^{2+}$ and Cr$^{4+}$, and bis(cyclopentadienyl) Cr$^{2+}$, onto a chromium oxide catalyst, such as those described above. Suitable transition metal catalysts also include supported chromium catalysts such as those based on chromocene or a silylchromate (e.g., bi(trisphenylsilyl)chromate). These chromium catalysts can be supported on any suitable high surface area support such as those described above for the chromium oxide catalysts, with silica typically being used. The supported chromium catalysts can also be used in conjunction with cocatalysts, such as the metal alkyl cocatalysts listed above for the chromium oxide catalysts. Suitable transition metal halide catalysts include titanium (III) halides (e.g., titanium (III) chloride), titanium (IV) halides (e.g., titanium (IV) chloride), vanadium halides, zirconium halides, and combinations thereof. These transition metal halides are often supported on a high surface area solid, such as magnesium chloride. The transition metal halide catalysts are typically used in conjunction with an aluminum alkyl cocatalyst, such as trimethylaluminum (i.e., Al(CH$_3$)$_3$) or triethylaluminum (i.e., Al(C$_2$H$_5$)$_3$). These transition metal halides may also be used in staged reactor processes. Suitable catalysts also include metallocene catalysts, such as cyclopentadienyl titanium halides (e.g., cyclopentadienyl titanium chlorides), cyclopentadienyl zirconium halides (e.g., cyclopentadienyl zirconium chlorides), cyclopentadienyl hafnium halides (e.g., cyclopentadienyl hafnium chlorides), and combinations thereof. Metallocene catalysts based on transition metals complexed with indenyl or fluorenyl ligands are also known and can be used to produce high density polyethylene polymers suitable for use in the invention. The catalysts typically contain multiple ligands, and the ligands can be substituted with various groups (e.g., n-butyl group) or linked with bridging groups, such as —$CH_2CH_2$— or >$SiPh_2$. The metallocene catalysts typically are used in conjunction with a cocatalyst, such as methyl aluminoxane (i.e., $(Al(CH_3)_xO_y)_n$. Other cocatalysts include those described in U.S. Pat. No. 5,919,983 (Rosen et al.), U.S. Pat. No. 6,107,230 (McDaniel et al.), U.S. Pat. No. 6,632,894 (McDaniel et al.), and U.S. Pat. No. 6,300,271 (McDaniel et al). Other "single site" catalysts suitable for use in producing high density polyethylene include diimine complexes, such as those described in U.S. Pat. No. 5,891,963 (Brookhart et al.).

The high density polyethylene polymers suitable for use in the invention can have any suitable molecular weight (e.g., weight average molecular weight). For example, the weight average molecular weight of the high density polyethylene can be from 20,000 g/mol to about 1,000,000 g/mol or more. As will be understood by those of ordinary skill in the art, the suitable weight average molecular weight of the high density polyethylene will depend, at least in part, on the particular application or end use for which the polymer is destined. For example, a high density polyethylene polymer intended for blow molding applications can have a weight average molecular weight of about 100,000 g/mol to about 1,000,000 g/mol. A high density polyethylene polymer intended for pipe applications or film applications can have a weight average molecular weight of about 100,000 g/mol to about 500,000 g/mol. A high density polyethylene polymer intended for injection molding applications can have a weight average molecular weight of about 20,000 g/mol to about 80,000 g/mol. A high density polyethylene polymer intended for wire insulation applications, cable insulation applications, tape applications, or filament applications can have a weight average molecular weight of about 80,000 g/mol to about 400,000 g/mol. A high density polyethylene polymer intended for rotomolding applications can have a weight average molecular weight of about 50,000 g/mol to about 150,000 g/mol.

The high density polyethylene polymers suitable for use in the invention can also have any suitable polydispersity, which is defined as the value obtained by dividing the weight average molecular weight of the polymer by the number average molecular weight of the polymer. For example, the high density polyethylene polymer can have a polydispersity of greater than 2 to about 100. As understood by those skilled in the art, the polydispersity of the polymer is heavily influenced by the catalyst system used to produce the polymer, with the metallocene and other "single site" catalysts generally producing polymers with relatively low polydispersity and narrow molecular weight distributions and the other transition metal catalysts (e.g., chromium catalysts) producing polymers with higher polydispersity and broader molecular weight distributions. The high density polyethylene polymers suitable for use in the invention can also have a multimodal (e.g., bimodal) molecular weight distribution. For example, the polymer can have a first fraction having a relatively low molecular weight and a second fraction having a relatively high molecular weight. The difference between the weight average molecular weight of the fractions in the polymer can be any suitable amount. In fact, it is not necessary for the difference between the weight average molecular weights to be large enough that two distinct molecular weight fractions can be resolved using gel permeation chromatography (GPC). However, in certain multimodal polymers, the difference between the weight average molecular weights of the fractions can be great enough that two or more distinct peaks can be resolved from the GPC curve for the polymer. In this context, the term "distinct" does not necessarily mean that the portions of the GPC curve corresponding to each fraction do not overlap, but is merely meant to indicate that a distinct peak for each fraction can be resolved from the GPC curve for the polymer. The multimodal polymers suitable for use in the invention can be produced using any suitable process. As noted above, the multimodal polymers can be produced using staged reactor processes. One suitable example would be a staged solution process incorporating a series of stirred tanks. Alternatively, the multimodal polymers can be produced in a single reactor using a combination of catalysts each of which is designed to produce a polymer having a different weight average molecular weight.

The high density polyethylene polymers suitable for use in the invention can have any suitable melt index. For example, the high density polyethylene polymer can have a melt index of about 0.01 dg/min to about 40 dg/min. As with the weight average molecular weight, those of ordinary skill in the art understand that the suitable melt index for the high density polyethylene polymer will depend, at least in part, on the particular application or end use for which the polymer is destined. Thus, for example, a high density polyethylene polymer intended for blow molding applications can have a melt index of about 0.01 dg/min to about 1 dg/min. A high density polyethylene polymer intended for blown film applications can have a melt index of about 0.5 dg/min to about 3 dg/min. A high density polyethylene polymer intended for cast film applications can have a melt index of about 2 dg/min to about 10 dg/min. A high density polyethylene polymer intended for pipe applications can have a melt index of about 2 dg/min to about 40 dg/min. A high density polyethylene polymer intended for injection molding applications can have a melt index of about 2 dg/min to about 80 dg/min. A high density polyethylene polymer intended for rotomolding applications can have a melt index of about 0.5 dg/min to about 10 dg/min. A high density polyethylene polymer intended for tape applications can have a melt index of about 0.2 dg/min to about 4 dg/min. A high density polyethylene polymer intended for filament applications can have a melt index of about 1 dg/min to about 20 dg/min. The melt index of the polymer is measured using ASTM Standard D1238-04c.

The high density polyethylene polymers suitable for use in the invention generally do not contain high amounts of long-chain branching. The term "long-chain branching" is used to refer to branches that are attached to the polymer chain and are of sufficient length to affect the rheology of the polymer (e.g., branches of about 130 carbons or more in length). If desired for the application in which the polymer is to be used, the high density polyethylene polymer can contain small amounts of long-chain branching. However, the high density polyethylene polymers suitable for use in the invention typically contain very little long-chain branching (e.g., less than about 1 long-chain branch per 10,000 carbons, less than about 0.5 long-chain branches per 10,000 carbons, less than about 0.1 long-chain branches per 10,000 carbons, or less than about 0.01 long-chain branches per 10,000 carbons).

The medium density polyethylene polymers suitable for use in the invention generally have a density of about 0.926 g/cm$^3$ to about 0.940 g/cm$^3$. The term "medium density polyethylene" is used to refer to polymers of ethylene that have a density between that of high density polyethylene and linear low density polyethylene and contain relatively short branches, at least as compared to the long branches present in low density polyethylene polymers produced by the free radical polymerization of ethylene at high pressures.

The medium density polyethylene polymers suitable for use in the invention generally are copolymers of ethylene and at least one α-olefin, such as 1-butene, 1-hexene, 1-octene, 1-decene, and 4-methyl-1-pentene. The α-olefin comonomer can be present in any suitable amount, but typically is present in an amount of less than about 8% by weight (e.g., less than about 5 mol %). As will be understood by those of ordinary skill in the art, the amount of comonomer suitable for the copolymer is largely driven by the end use for the copolymer and the required or desired polymer properties dictated by that end use.

The medium density polyethylene polymers suitable for use in the invention can be produced by any suitable process. Like the high density polyethylene polymers, the medium density polyethylene polymers typically are produced in "low pressure" catalytic processes such as any of the processes described above in connection with the high density polyethylene polymers suitable for use in the invention. Examples of suitable processes include, but are not limited to, gas-phase polymerization processes, solution polymerization processes, slurry polymerization processes, and staged reactor processes. Suitable staged reactor processes can incorporate any suitable combination of the gas-phase, solution, and slurry polymerization processes described above. As with high density polyethylene polymers, staged reactor processes are often used to produce multimodal polymers.

The medium density polyethylene polymers suitable for use in the invention can be produced using any suitable catalyst or combination of catalysts. For example, the polymers can be produced using Ziegler catalysts, such as transition metal (e.g., titanium) halides or esters used in combination with organoaluminum compounds (e.g., triethylaluminum). These Ziegler catalysts can be supported on, for example, magnesium chloride, silica, alumina, or magnesium oxide. The medium density polyethylene polymers suitable for use in the invention can also be produced using so-called "dual Ziegler catalysts," which contain one catalyst species for dimerizing ethylene into 1-butene (e.g., a combination of a titanium ester and triethylaluminum) and another catalyst for copolymerization of ethylene and the generated 1-butene (e.g., titanium chloride supported on magnesium chloride). The medium density polyethylene polymers suitable for use in the invention can also be produced using chromium oxide catalysts, such as those produced by depositing a chromium compound onto a silica-titania support, oxidizing the resulting catalyst in a mixture of oxygen and air, and then reducing the catalyst with carbon monoxide. These chromium oxide catalysts typically are used in conjunction with cocatalysts such as trialkylboron or trialkylaluminum compounds. The chromium oxide catalysts can also be used in conjunction with a Ziegler catalyst, such as a titanium halide- or titanium ester-based catalyst. The medium density polyethylene polymers suitable for use in the invention can also be produced using supported chromium catalysts such as those described above in the discussion of catalysts suitable for making high density polyethylene. The medium density polyethylene polymers suitable for use in the invention can also be produced using metallocene catalysts. Several different types of metallocene catalysts can be used. For example, the metallocene catalyst can contain a bis(metallocene) complex of zirconium, titanium, or hafnium with two cyclopentadienyl rings and methylaluminoxane. As with the catalysts used in high density polyethylene production, the ligands can be substituted with various groups (e.g., n-butyl group) or linked with bridging groups. Another class of metallocene catalysts that can be used are composed of bis(metallocene) complexes of zirconium or titanium and anions of perfluorinated boron-aromatic compounds. A third class of metallocene catalysts that can be used are referred to as constrained-geometry catalysts and contain monocyclopentadienyl derivatives of titanium or zirconium in which one of the carbon atoms in the cyclopentadienyl ring is linked to the metal atom by a bridging group. These complexes are activated by reacting them with methylaluminoxane or by forming ionic complexes with noncoordinative anions, such as $B(C_6F_5)_4^-$ or $B(C_6F_5)_3CH_3^-$. A fourth class of metallocene catalysts that can be used are metallocene-based complexes of a transition metal, such as titanium, containing one cyclopentadienyl ligand in combination with another ligand, such as a phosphinimine or —O—$SiR_3$. This class of metallocene catalyst is also activated with methylaluminoxane or a boron compound. Other catalysts suitable for use in making the medium density polyethylene suitable for use in the invention include, but are not limited to, the catalysts disclosed in U.S. Pat. No. 6,649,558.

The medium density polyethylene polymers suitable for use in the invention can have any suitable compositional uniformity, which is a term used to describe the uniformity of the branching in the copolymer molecules of the polymer. Many commercially-available medium density polyethylene polymers have a relatively low compositional uniformity in which the high molecular weight fraction of the polymer contains relatively little of the α-olefin comonomer and has relatively little branching while the low molecular weight fraction of the polymer contains a relatively high amount of the α-olefin comonomer and has a relatively large amount of branching. Alternatively, another set of medium density polyethylene polymers have a relatively low compositional uniformity in which the high molecular weight fraction of the polymer contains a relatively high amount of the α-olefin comonomer while the low molecular weight fraction of the polymer contains relatively little of the α-olefin comonomer. The compositional uniformity of the polymer can be measured using any suitable method, such as temperature rising elution fractionation.

The medium density polyethylene polymers suitable for use in the invention can have any suitable molecular weight. For example, the polymer can have a weight average molecular weight of about 50,000 g/mol to about 200,000 g/mol. As will be understood by those of ordinary skill in the art, the suitable weight average molecular weight of the medium density polyethylene will depend, at least in part, on the particular application or end use for which the polymer is destined.

The medium density polyethylene polymers suitable for use in the invention can also have any suitable polydispersity. Many commercially available medium density polyethylene polymers have a polydispersity of about 2 to about 30. The medium density polyethylene polymers suitable for use in the invention can also have a multimodal (e.g., bimodal) molecular weight distribution. For example, the polymer can have a first fraction having a relatively low molecular weight and a second fraction having a relatively high molecular weight. As with the high density polyethylene polymers suitable for use in the invention, the difference between the weight average molecular weight of the fractions in the multimodal medium density polyethylene polymer can be any suitable amount. In fact, it is not necessary for the difference between the weight average molecular weights to be large enough that two distinct molecular weight fractions can be resolved using gel permeation chromatography (GPC). However, in certain multimodal polymers, the difference between the weight average molecular weights of the fractions can be great enough that two or more distinct peaks can be resolved from the GPC curve for the polymer. In this context, the term "distinct" does not necessarily mean that the portions of the GPC curve corresponding to each fraction do not overlap, but is merely meant to indicate that a distinct peak for each fraction can be resolved from the GPC curve for the polymer. The multimodal polymers suitable for use in the invention can be produced using any suitable process. As noted above, the multimodal polymers can be produced using staged reactor processes. One suitable example would be a staged solution process incorporating a series of stirred tanks. Alternatively, the multimodal polymers can be produced in a single reactor using a combination of catalysts each of which is designed to produce a polymer having a different weight average molecular weight The medium density polyethylene polymers suitable for use in the invention can have any suitable melt index. For example, the medium density polyethylene polymer can have a melt index of about 0.01 dg/min to about 200 dg/min. As with the weight average molecular weight, those of ordinary skill in the art understand that the suitable melt index for the medium density polyethylene polymer will depend, at least in part, on the particular application or end use for which the polymer is destined. Thus, for example, a medium density polyethylene polymer intended for blow molding applications or pipe applications can have a melt index of about 0.01 dg/min to about 1 dg/min. A medium density polyethylene polymer intended for blown film applications can have a melt index of about 0.5 dg/min to about 3 dg/min. A medium density polyethylene polymer intended for cast film applications can have a melt index of about 2 dg/min to about 10 dg/min. A medium density polyethylene polymer intended for injection molding applications can have a melt index of about 6 dg/min to about 200 dg/min. A medium density polyethylene polymer intended for rotomolding applications can have a melt index of about 4 dg/min to about 7 dg/min. A medium density polyethylene polymer intended for wire and cable insulation applications can have a melt index of about 0.5 dg/min to about 3 dg/min. The melt index of the polymer is measured using ASTM Standard D1238-04c.

The medium density polyethylene polymers suitable for use in the invention generally do not contain a significant amount of long-chain branching. For example, the medium density polyethylene polymers suitable for use in the invention generally contain less than about 0.1 long-chain branches per 10,000 carbon atoms (e.g., less than about 0.002 long-chain branches per 100 ethylene units) or less than about 0.01 long-chain branches per 10,000 carbon atoms.

The linear low density polyethylene polymers suitable for use in the invention generally have a density of 0.925 g/cm$^3$ or less (e.g., about 0.910 g/cm$^3$ to about 0.925 g/cm$^3$). The term "linear low density polyethylene" is used to refer to lower density polymers of ethylene having relatively short branches, at least as compared to the long branches present in low density polyethylene polymers produced by the free radical polymerization of ethylene at high pressures.

The linear low density polyethylene polymers suitable for use in the invention generally are copolymers of ethylene and at least one α-olefin, such as 1-butene, 1-hexene, 1-octene, 1-decene, and 4-methyl-1-pentene. The α-olefin comonomer can be present in any suitable amount, but typically is present in an amount of less than about 6 mol. % (e.g., about 2 mol % to about 5 mol %). As will be understood by those of ordinary skill in the art, the amount of comonomer suitable for the copolymer is largely driven by the end use for the copolymer and the required or desired polymer properties dictated by that end use.

The linear low density polyethylene polymers suitable for use in the invention can be produced by any suitable process. Like the high density polyethylene polymers, the linear low density polyethylene polymers typically are produced in "low pressure" catalytic processes such as any of the processes described above in connection with the high density polyethylene polymers suitable for use in the invention. Suitable processes include, but are not limited to, gas-phase polymerization processes, solution polymerization processes, slurry polymerization processes, and staged reactor processes. Suitable staged reactor processes can incorporate any suitable combination of the gas-phase, solution, and slurry polymerization processes described above. As with high density polyethylene polymers, staged reactor processes are often used to produce multimodal polymers.

The linear low density polyethylene polymers suitable for use in the invention can be produced using any suitable catalyst or combination of catalysts. For example, the polymers can be produced using Ziegler catalysts, such as transition metal (e.g., titanium) halides or esters used in combination with organoaluminum compounds (e.g., triethylaluminum). These Ziegler catalysts can be supported on, for example, magnesium chloride, silica, alumina, or magnesium oxide. The linear low density polyethylene polymers suitable for use in the invention can also be produced using so-called "dual Ziegler catalysts," which contain one catalyst species for dimerizing ethylene into 1-butene (e.g., a combination of a titanium ester and triethylaluminum) and another catalyst for copolymerization of ethylene and the generated 1-butene (e.g., titanium chloride supported on magnesium chloride). The linear low density polyethylene polymers suitable for use in the invention can also be produced using chromium oxide catalysts, such as those produced by depositing a chromium compound onto a silica-titania support, oxidizing the resulting catalyst in a mixture of oxygen and air, and then reducing the catalyst with carbon monoxide. These chromium oxide catalysts typically are used in conjunction with cocatalysts such as trialkylboron or trialkylaluminum compounds. The chromium oxide catalysts can also be used in conjunction with a Ziegler catalyst, such as a titanium halide- or titanium ester-based catalyst. The linear low density polyethylene polymers suitable for use in the invention can also be produced using supported chromium catalysts such as those described above in the discussion of catalysts suitable for making high density polyethylene. The linear low density polyethylene suitable for use in the invention can also be produced using metallocene catalysts. Several different types of metallocene catalysts can be used. For example, the metallocene catalyst can contain a bis(metallocene) complex of zirconium, titanium, or hafnium with two cyclopentadienyl rings and methylaluminoxane. As with the catalysts used in high density polyethylene production, the ligands can be substituted with various groups (e.g., n-butyl group) or linked with bridging groups. Another class of metallocene catalysts that can be used are composed of bis(metallocene) complexes of zirconium or titanium and anions of perfluorinated boron-aromatic compounds. A third class of metallocene catalysts that can be used are referred to as constrained-geometry catalysts and contain monocyclopentadienyl derivatives of titanium or zirconium in which one of the carbon atoms in the cyclopentadienyl ring is linked to the metal atom by a bridging group. These complexes are activated by reacting them with methylaluminoxane or by forming ionic complexes with noncoordinative anions, such as $B(C_6F_5)_4^-$ or $B(C_6F_5)_3CH_3^-$. A fourth class of metallocene catalysts that can be used are metallocene-based complexes of a transition metal, such as titanium, containing one cyclopentadienyl ligand in combination with another ligand, such as a phosphinimine or —O—$SiR_3$. This class of metallocene catalyst is also activated with methylaluminoxane or a boron compound. Other catalysts suitable for use in making the linear low density polyethylene suitable for use in the invention include, but are not limited to, the catalysts disclosed in U.S. Pat. No. 6,649,558.

The linear low density polyethylene polymers suitable for use in the invention can have any suitable compositional uniformity, which is a term used to describe the uniformity of the branching in the copolymer molecules of the polymer. Many commercially-available linear low density polyethylene polymers have a relatively low compositional uniformity in which the high molecular weight fraction of the polymer contains relatively little of the α-olefin comonomer and has relatively little branching while the low molecular weight fraction of the polymer contains a relatively high amount of the α-olefin comonomer and has a relatively large amount of branching. Alternatively, another set of linear low density polyethylene polymers have a relatively low compositional uniformity in which the high molecular weight fraction of the polymer contains a relatively high amount of the α-olefin comonomer while the low molecular weight fraction of the polymer contains relatively little of the α-olefin comonomer. The compositional uniformity of the polymer can be measured using any suitable method, such as temperature rising elution fractionation.

The linear low density polyethylene polymers suitable for use in the invention can have any suitable molecular weight. For example, the polymer can have a weight average molecular weight of about 20,000 g/mol to about 250,000 g/mol. As will be understood by those of ordinary skill in the art, the suitable weight average molecular weight of the linear low density polyethylene will depend, at least in part, on the particular application or end use for which the polymer is destined.

The linear low density polyethylene polymers suitable for use in the invention can also have any suitable polydispersity. Many commercially available linear low density polyethylene polymers have a relatively narrow molecular weight distribution and thus a relatively low polydispersity, such as about 2 to about 5 (e.g., about 2.5 to about 4.5 or about 3.5 to about 4.5). The linear low density polyethylene polymers suitable for use in the invention can also have a multimodal (e.g., bimodal) molecular weight distribution. For example, the polymer can have a first fraction having a relatively low molecular weight and a second fraction having a relatively high molecular weight. As with the high density polyethylene polymers suitable for use in the invention, the difference between the weight average molecular weight of the fractions in the multimodal linear low density polyethylene polymer can be any suitable amount. In fact, it is not necessary for the difference between the weight average molecular weights to be large enough that two distinct molecular weight fractions can be resolved using gel permeation chromatography (GPC). However, in certain multimodal polymers, the difference between the weight average molecular weights of the fractions can be great enough that two or more distinct peaks can be resolved from the GPC curve for the polymer. In this context, the term "distinct" does not necessarily mean that the portions of the GPC curve corresponding to each fraction do not overlap, but is merely meant to indicate that a distinct peak for each fraction can be resolved from the GPC curve for the polymer. The multimodal polymers suitable for use in the invention can be produced using any suitable process. As noted above, the multimodal polymers can be produced using staged reactor processes. One suitable example would be a staged solution process incorporating a series of stirred tanks. Alternatively, the multimodal polymers can be produced in a single reactor using a combination of catalysts each of which is designed to produce a polymer having a different weight average molecular weight The linear low density polyethylene polymers suitable for use in the invention can have any suitable melt index. For example, the linear low density polyethylene polymer can have a melt index of about 0.01 dg/min to about 200 dg/min. As with the weight average molecular weight, those of ordinary skill in the art understand that the suitable melt index for the linear low density polyethylene polymer will depend, at least in part, on the particular application or end use for which the polymer is destined. Thus, for example, a linear low density polyethylene polymer intended for blow molding applications or pipe applications can have a melt index of about 0.01 dg/min to about 1 dg/min. A linear low density polyethylene polymer intended for blown film applications can have a melt index of about 0.5 dg/min to about 3 dg/min. A linear low density polyethylene polymer intended for cast film applications can have a melt index of about 2 dg/min to about 10 dg/min. A linear low density polyethylene polymer intended for injection molding applications can have a melt index of about 6 dg/min to about 200 dg/min. A linear low density polyethylene polymer intended for rotomolding applications can have a melt index of about 4 dg/min to about 7 dg/min. A linear low density polyethylene polymer intended for wire and cable insulation applications can have a melt index of about 0.5 dg/min to about 3 dg/min. The melt index of the polymer is measured using ASTM Standard D1238-04c.

The linear low density polyethylene polymers suitable for use in the invention generally do not contain a significant amount of long-chain branching. For example, the linear low density polyethylene polymers suitable for use in the invention generally contain less than about 0.1 long-chain branches per 10,000 carbon atoms (e.g., less than about 0.002 long-chain branches per 100 ethylene units) or less than about 0.01 long-chain branches per 10,000 carbon atoms.

The low density polyethylene polymers suitable for use in the invention generally have a density of less than 0.935 g/cm$^3$ and, in contrast to high density polyethylene, medium density polyethylene and linear low density polyethylene, have a relatively large amount of long-chain branching in the polymer.

The low density polyethylene polymers suitable for use in the invention can be either ethylene homopolymers or copolymers of ethylene and a polar comonomer. Suitable polar comonomers include, but are not limited to, vinyl acetate, methyl acrylate, ethyl acrylate, and acrylic acid. These comonomers can be present in any suitable amount, with comonomer contents as high as 20% by weight being used for certain applications. As will be understood by those skilled in the art, the amount of comonomer suitable for the polymer is largely driven by the end use for the polymer and the required or desired polymer properties dictated by that end use.

The low density polyethylene polymers suitable for use in the invention can be produced using any suitable process, but typically the polymers are produced by the free-radical initiated polymerization of ethylene at high pressure (e.g., about 81 to about 276 MPa) and high temperature (e.g., about 130 to about 330° C.). Any suitable free radical initiator can be used in such processes, with peroxides and oxygen being the most common. The free-radical polymerization mechanism gives rise to short-chain branching in the polymer and also to the relatively high degree of long-chain branching that distinguishes low density polyethylene from other ethylene polymers (e.g., high density polyethylene and linear low density polyethylene). The polymerization reaction typically is performed in an autoclave reactor (e.g., a stirred autoclave reactor), a tubular reactor, or a combination of such reactors positioned in series.

The low density polyethylene polymers suitable for use in the invention can have any suitable molecular weight. For example, the polymer can have a weight average molecular weight of about 30,000 g/mol to about 500,000 g/mol. As will be understood by those of ordinary skill in the art, the suitable weight average molecular weight of the low density polyethylene will depend, at least in part, on the particular application or end use for which the polymer is destined. For example, a low density polyethylene polymer intended for blow molding applications can have a weight average molecular weight of about 80,000 g/mol to about 200,000 g/mol. A low density polyethylene polymer intended for pipe applications can have a weight average molecular weight of about 80,000 g/mol to about 200,000 g/mol. A low density polyethylene polymer intended for injection molding applications can have a weight average molecular weight of about 30,000 g/mol to about 80,000 g/mol. A low density polyethylene polymer intended for film applications can have a weight average molecular weight of about 60,000 g/mol to about 500,000 g/mol.

The low density polyethylene polymers suitable for use in the invention can have any suitable melt index. For example, the low density polyethylene polymer can have a melt index of about 0.2 to about 100 dg/min. As noted above, the melt index of the polymer is measured using ASTM Standard D1238-04c.

As noted above, one of the major distinctions between low density polyethylene and other ethylene polymers is a relatively high degree of long-chain branching within the polymer. The low density polyethylene polymers suitable for use in the invention can exhibit any suitable amount of long-chain branching, such as about 0.01 or more long-chain branches per 10,000 carbon atoms, about 0.1 or more long-chain branches per 10,000 carbon atoms, about 0.5 or more long-chain branches per 10,000 carbon atoms, about 1 or more long-chain branches per 10,000 carbon atoms, or about 4 or more long-chain branches per 10,000 carbon atoms. While there is not a strict limit on the maximum extent of long-chain branching that can be present in the low density polyethylene polymers suitable for use in the invention, the long-chain branching in many low density polyethylene polymers is less than about 100 long-chain branches per 10,000 carbon atoms.

The thermoplastic polymer composition also comprises a nucleating agent. As utilized herein, the term "nucleating agent" is used to refer to compounds or additives that form nuclei or provide sites for the formation and/or growth of crystals in a polymer as it solidifies from a molten state. In a first embodiment, the nucleating agent comprises a compound conforming to the structure of Formula (I)

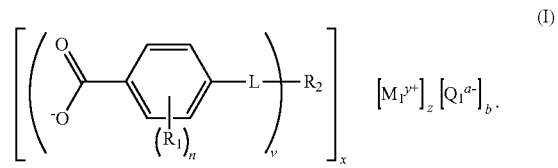

In the structure of Formula (I), $R_1$ is selected from the group consisting of hydroxy, halogens, alkyl groups, substituted alkyl groups, alkoxy groups, substituted alkoxy groups, aryl groups, and substituted aryl groups. The variable n is zero or a positive integer from 1 to 4. L is a linking group comprising two or more atoms and at least one double bond between two atoms in the linking group. The variable v is a positive integer from 1 to 3. $R_2$ is: (i) selected from the group consisting of alkyl groups, substituted alkyl groups, cycloalkyl groups, substituted cycloalkyl groups, aryl groups, substituted aryl groups, heteroaryl groups, and substituted heteroaryl groups when L is a divalent linking group and v is 1, (ii) selected from the group consisting of alkanediyl groups, substituted alkanediyl groups, cycloalkanediyl groups, substituted cycloalkanediyl groups, arenediyl groups, substituted arenediyl groups, heteroarenediyl groups, and substituted heteroarenediyl groups when L is a trivalent linking group and v is 1, (iii) selected from the group consisting of alkanediyl groups, substituted alkanediyl groups, cycloalkanediyl groups, substituted cycloalkanediyl groups, arenediyl groups, substituted arenediyl groups, heteroarenediyl groups, and substituted heteroarenediyl groups when L is a divalent linking group and v is 2, and (iv) selected from the group consisting of alkanetriyl groups, substituted alkanetriyl groups, cycloalkanetriyl groups, substituted cycloalkanetriyl groups, arenetriyl groups, substituted arenetriyl groups, heteroarenetriyl groups, and substituted heteroarenetriyl groups when L is a divalent linking group and v is 3. The variable x is a positive integer. Each $M_1$ is a metal cation; the variable y is the valence of the cation; and the variable z is a positive integer. The variable b is zero or a positive integer. When b is a positive integer, each $Q_1$ is a negatively-charged counterion, and a is the valence of the negatively-charged counterion. The values of v, x, y, z, a, and b satisfy the equation $(vx)+(ab)=yz$. In the structure of Formula (I), the cyclic portion of the cycloalkyl group or substituted cycloalkyl group comprises no more than two ring structures fused together when L is a divalent linking group, v is 1, and $R_2$ is a cycloalkyl group or a substituted cycloalkyl group.

In a preferred embodiment, $R_1$ is a halogen or hydroxy, with n=1 being particularly preferred. In a more specific embodiment, n can be 1, $R_1$ can be hydroxy and attached to the aryl ring in the ortho position relative to the carboxylate group. In another preferred embodiment, n is 0, meaning that the carboxylate-substituted aryl ring is not substituted with $R_1$ groups.

L is a linking group comprising two or more atoms and at least one double bond between two atoms in the linking group. With at least one double bond between two atoms in the linking group, two of the atoms in the linking group are $sp^2$ hybridized and the sum of the bond angles around at least one of these atoms is approximately 360 degrees. The presence of the double bond within the liking group restricts rotation of the molecule around the double bond and, while not wishing to be bound to any particular theory, is believed to maintain the compound in a configuration that is more favorable for nucleation of the polymer. In a series of preferred embodiments, L is selected from the group consisting of moieties conforming to the structure of one of Formulae (LA)-(LF) below (LA)

(LB)

(LC)

(LD)

(LE)

(LF)

As can be seen from these structures, suitable linking groups comprise at least two atoms and a double bond between two atoms in the linking group. With each of these L groups, any suitable end of the linking group can be attached to the carboxylate-substituted aryl ring and the other end(s) can be attached to the group $R_2$. In a preferred embodiment, L is a moiety selecting from the group consisting of moieties conforming to the structure of Formulae (LA) and (LD). In a particularly preferred embodiment, L is a moiety conforming to the structure of Formula (LA). In such an embodiment, the moiety can have the nitrogen atom bonded to the carboxylate-substituted aryl ring or the group $R_2$.

The group $R_2$ can be a monovalent, divalent, or trivalent moiety. The valence of $R_2$ depends on the valence of the linking group L and the number of carboxylate-substituted aryl rings in the compound. Thus, when L is a divalent linking group, v is 1, and $R_2$ can be selected from the group consisting of moieties conforming to the structure of one of Formulae (AA)-(AG) below. The structure of Formula (AA) is (AA)

In the structure of Formula (AA), the variable d is zero or a positive integer from 1 to 5, and each $R_{10}$ is independently selected from the group consisting of halogens, alkyl groups, substituted alkyl groups, alkoxy groups, substituted alkoxy groups, aryl groups, and substituted aryl groups. The structure of Formula (AB) is (AB)

In the structure of Formula (AB), the variable h is zero or a positive integer from 1 to 10, and each $R_{13}$ is independently selected from the group consisting of halogens, alkyl groups, substituted alkyl groups, alkoxy groups, substituted alkoxy groups, aryl groups, and substituted aryl groups. The structure of Formula (AC) is (AC)

In the structure of Formula (AC), the variable e is zero or a positive integer from 1 to 8, and each $R_{15}$ is independently selected from the group consisting of halogens, alkyl groups, substituted alkyl groups, alkoxy groups, substituted alkoxy groups, aryl groups, and substituted aryl groups. The structure of Formula (AD) is (AD)

In the structure of Formula (AD), the variable g is zero or a positive integer from 1 to 6, and each $R_{20}$ is independently selected from the group consisting of halogens, alkyl groups, substituted alkyl groups, alkoxy groups, substituted alkoxy groups, aryl groups, and substituted aryl groups. The structure of Formula (AE) is (AE)

In the structure of Formula (AE), the variable j is zero or a positive integer from 1 to 4, and each $R_{25}$ is independently selected from the group consisting of halogens, alkyl groups, substituted alkyl groups, alkoxy groups, substituted alkoxy groups, aryl groups, and substituted aryl groups. The structure of Formula (AF) is

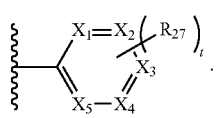
(AF)

In the structure of Formula (AF), the variable $X_1$, $X_2$, $X_3$, $X_4$, and $X_5$ are independently selected from the group consisting of a carbon atom and a nitrogen atom, provided at least one and no more than three of $X_1$, $X_2$, $X_3$, $X_4$, and $X_5$ are nitrogen atoms; t is zero or a positive integer equal to 5−X where X is the number of nitrogen atoms; and each $R_{27}$ is independently selected from the group consisting of halogens, alkyl groups, substituted alkyl groups, alkoxy groups, substituted alkoxy groups, aryl groups, and substituted aryl groups. The structure of Formula (AG) is

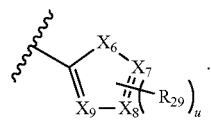
(AG)

In the structure of Formula (AG), the variable $X_6$ is selected from the group consisting of a carbon atom, an oxygen atom, a sulfur atom, and a secondary amine group, $X_7$, $X_8$, and $X_9$ are independently selected from the group consisting of a carbon atom and a nitrogen atom, at least one and no more than three of $X_6$, $X_7$, $X_8$, and $X_9$ are non-carbon atoms; u is zero or a positive integer equal to 4−Y where Y is the number of non-carbon atoms in the ring structure; and each $R_{29}$ is independently selected from the group consisting of halogens, cyano groups, alkyl groups, substituted alkyl groups, alkoxy groups, substituted alkoxy groups, aryl groups, and substituted aryl groups.

When L is a trivalent linking group, v is 1, and $R_2$ can be selected from the group consisting of moieties conforming to the structure of one of Formula (AH)-(AJ) below. The structure of Formula (AH) is

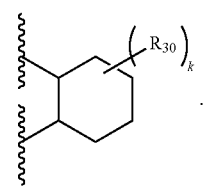
(AH)

In the structure of Formula (AH), the variable k is zero or a positive integer from 1 to 8, and each $R_{30}$ is independently selected from the group consisting of halogens, alkyl groups, substituted alkyl groups, alkoxy groups, substituted alkoxy groups, aryl groups, and substituted aryl groups. The structure of Formula (AI) is

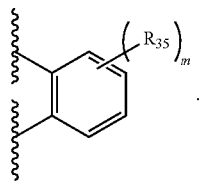
(AI)

In the structure of Formula (AI), the variable m is zero or a positive integer from 1 to 4, and each $R_{35}$ is independently selected from the group consisting of halogens, alkyl groups, substituted alkyl groups, alkoxy groups, substituted alkoxy groups, aryl groups, and substituted aryl groups. The structure of Formula (AJ) is

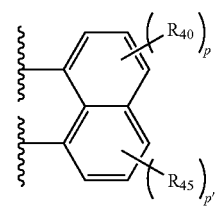
(AJ)

In the structure of Formula (AJ), the variable p is zero or a positive integer from 1 to 3, p' is zero or a positive integer from 1 to 3, and each $R_{40}$ and $R_{45}$ is independently selected from the group consisting of halogens, alkyl groups, substituted alkyl groups, alkoxy groups, substituted alkoxy groups, aryl groups, and substituted aryl groups.

When L is a divalent liking group, v is 2, and $R_2$ can selected from the group consisting of moieties conforming to the structure of Formula (BA) below

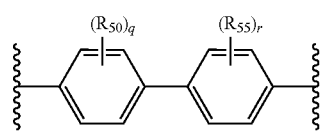
(BA)

In the structure of Formula (BA), the variable q is zero or a positive integer from 1 to 4, r is zero or a positive integer from 1 to 4, and each $R_{50}$ and $R_{55}$ is independently selected from the group consisting of halogens, alkyl groups, substituted alkyl groups, alkoxy groups, substituted alkoxy groups, aryl groups, and substituted aryl groups.

When L is a divalent linking group, v is 3, and $R_2$ can be selected from the group consisting of moieties conforming to the structure of Formula (CA) below

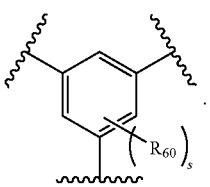
(CA)

In the structure of Formula (CA), the variable s is zero or a positive integer from 1 to 3, and each $R_{60}$ is independently selected from the group consisting of halogens, alkyl groups, substituted alkyl groups, alkoxy groups, substituted alkoxy groups, aryl groups, and substituted aryl groups.

In a series of preferred embodiments, L is a divalent linking group, v is 1, and $R_2$ is a moiety conforming to the structure of Formula (AA). Within this series of preferred embodiments, the variable d preferably is zero or 1. If d is 1, the group $R_{10}$ preferably is attached to the aryl ring in the para position relative to the bond to the linking group L. Further if d is 1, the group $R_{10}$ preferably is a halogen (e.g., bromine), an alkoxy group (e.g., a methoxy group), or an aryl group (e.g., a phenyl group).

In a series of preferred embodiments, L is a divalent linking group, v is 1, and $R_2$ is a moiety conforming to the structure of Formula (AC). Within this series of preferred embodiments, the variable d preferably is zero or 1, with zero being particularly preferred.

As noted above, $M_1$ is a metal cation. Suitable metal cations include, but are not limited to, alkali metal cations (e.g., sodium), alkaline earth metal cations (e.g., calcium), transition metal cations (e.g., zinc), and group 13 metal cations (e.g., aluminum). As utilized herein, the term "transition metal" is used to refer those elements in the d-block of the periodic table of elements, which corresponds to groups 3 to 12 on the periodic table of elements. In a preferred embodiment, $M_1$ is a metal cation selected from the group consisting of lithium, sodium, magnesium, aluminum, potassium, calcium, and zinc. In another preferred embodiment, $M_1$ is a lithium cation. In those embodiments in which the compound contains more than one metal cation $M_1$, each $M_1$ can be the same or different.

In a series of preferred embodiments, the nucleating agent can comprise a compound conforming to the structure of one of Formulae (IA)-(IM) below

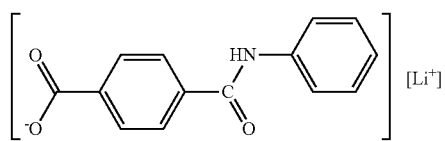
(IA)

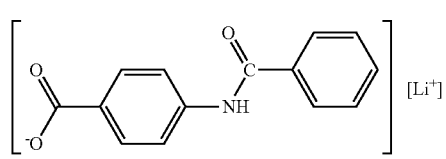
(IB)

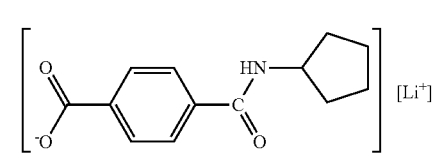
(IC)

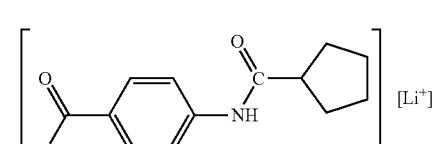
(ID)

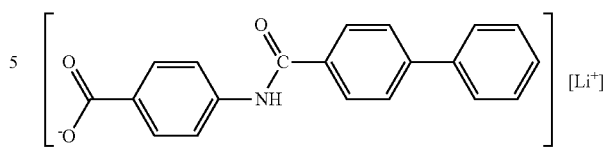
(IE)

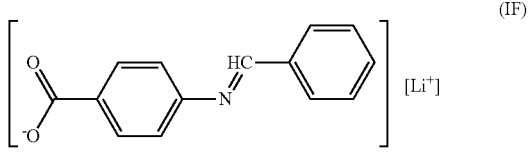
(IF)

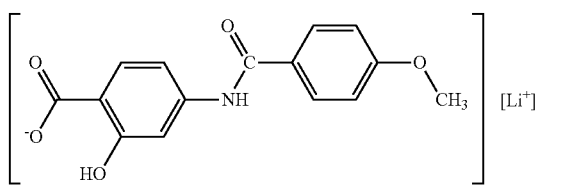
(IG)

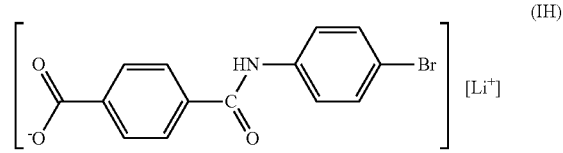
(IH)

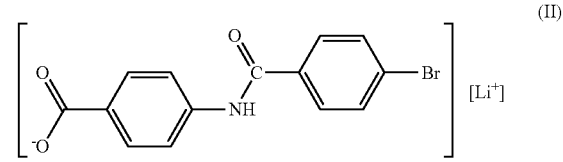
(II)

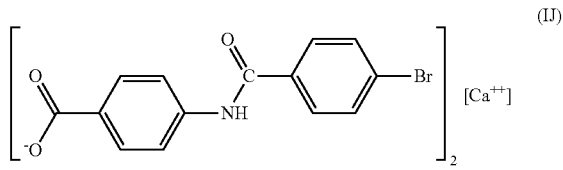
(IJ)

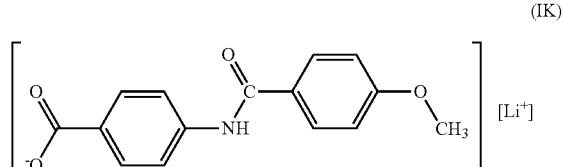
(IK)

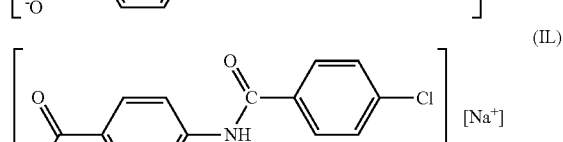
(IL)

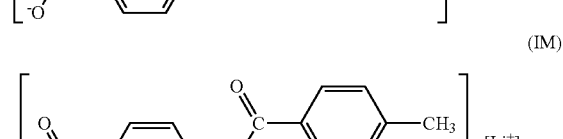
(IM)

The composition can comprise one or more metal salt compounds conforming to the structure of Formula (I). For example, the composition can comprise any suitable combination of the compounds conforming to the structures of (IA)-(IM) depicted above. More specifically, the composition can comprise a compound conforming to the structure of Formula (IA) and compound conforming to the structure of Formula (IL). In another specific embodiment, the composition can comprise a compound conforming to the structure of Formula (IB) and a compound conforming to the structure of Formula (IL). In yet another specific embodiment, the composition can comprise a compound conforming to the structure of Formula (IC) and a compound conforming to the structure of Formula (IL). Blends of these compounds can be used to produce compositions that exhibit a desired combination of properties, with one compound providing one benefit and another compound providing an additional benefit.

The metal salt compounds of Formula (I) and the more specific structures encompassed by Formula (I) can be synthesized using any suitable technique, many of which will be readily apparent to those of ordinary skill in the art. For example, if the acid used in making the compound is commercially available, the compound can be prepared by reacting the acid with a suitable base (e.g., a base comprising the desired metal cation and a Brønsted base) in a suitable medium (e.g., an aqueous medium). If the acid to be used in making the metal salt compound is not commercially available, the acid can be synthesized, for example, using any of the techniques illustrated below in the examples. Once the desired acid is obtained, the compound can be produced as described above (e.g., by reacting the acid with a suitable base in an appropriate medium).

The metal salt compounds of Formula (I) and the more specific structures encompassed by Formula (I) can be produced in various particle shapes and sizes. In general, these salt compounds form layered crystalline structures wherein the metal ions are present in galleries which are sandwiched between alternating layers of organic surfaces. As a result, flat platelet-like particles are often produced wherein the nucleating surfaces are exposed on the top and bottom of the particles, rather than the edges. The aspect ratio of these platelet-like particles is typically defined as the diameter, or breadth, versus the thickness. Elongated platelets, or "lath-like" crystals, are another particle morphology possible with these metal salt compounds. In these elongated structures, the aspect ratio typically is defined as the ratio of the length to the width. Aspect ratios of 2:1 up through 50:1 are possible. Particles with aspect ratios can align in molten polymer flow fields such that the flat surfaces are parallel to the machine, or flow, direction and parallel to the transverse, or cross, direction. As a result, the nucleating surfaces are exposed only in the normal direction of the polymer melt during part fabrication (exceptions would result when platelet-shaped particles possessed an aspect ratio insufficient for flat registry, and tumbling in the polymer flow direction results). Preferred particle orientations, or "registry", combined with specific crystallographic interactions with polyethylene during the nucleation event, can create directed lamellar growth which can result in unique and beneficial orientations of polyethylene crystals within the articles produced.

The particles of the nucleating agent discussed above can have any suitable size. Preferably, the particles of the nucleating agent are small enough that they are not visible in a finished article made from the thermoplastic polymer composition. Thus, in a preferred embodiment, the particles of the nucleating agent preferably are less than 25 microns in diameter, more preferably less than 20 microns in diameter, and most preferably less than 15 microns in diameter.

The nucleating agent can be present in the thermoplastic polymer composition in any suitable amount. The nucleating agent can be present in the thermoplastic polymer composition in an amount of about 50 parts per million (ppm) or more, about 100 ppm or more, about 250 ppm or more, or about 500 ppm or more, based on the total weight of the thermoplastic polymer composition. The nucleating agent typically is present in the thermoplastic polymer composition in an amount of about 10,000 ppm or less, about 7,500 ppm or less, about 5,000 ppm or less, about 4,000 ppm or less, or about 3,000 ppm or less, based on the total weight of the thermoplastic polymer composition. Thus, in certain embodiments of the thermoplastic polymer composition, the nucleating agent is present in the thermoplastic polymer composition in an amount of about 50 to about 10,000 ppm, about 100 to about 7,500 ppm (e.g., about 100 to about 5,000 ppm), about 250 to about 5,000 ppm (e.g., about 250 to about 4,000 ppm or about 250 to about 3,000 ppm), or about 500 to about 5,000 ppm (e.g., about 500 to about 4,000 ppm or about 500 to about 3,000 ppm), based on the total weight of the polymer composition.

The thermoplastic polymer composition of the invention can also be provided in the form of a masterbatch composition designed for addition or let-down into a virgin thermoplastic polymer. In such an embodiment, the thermoplastic polymer composition will generally contain a higher amount of the nucleating agent as compared to a thermoplastic polymer composition intended for use in the formation of an article of manufacture without further dilution or addition to a virgin thermoplastic polymer. For example, the nucleating agent can be present in such a thermoplastic polymer composition in an amount of about 1 wt. % to about 10 wt. % (e.g., about 1 wt. % to about 5 wt. % or about 2 wt. % to about 4 wt. %), based on the total weight of the thermoplastic polymer composition.

The thermoplastic polymer composition of the invention can contain other polymer additives in addition to the aforementioned nucleating agent. Suitable additional polymer additives include, but are not limited to, antioxidants (e.g., phenolic antioxidants, phosphite antioxidants, and combinations thereof), anti-blocking agents (e.g., amorphous silica and diatomaceous earth), pigments (e.g., organic pigments and inorganic pigments) and other colorants (e.g., dyes and polymeric colorants), fillers and reinforcing agents (e.g., glass, glass fibers, talc, calcium carbonate, and magnesium oxysulfate whiskers), nucleating agents, clarifying agents, acid scavengers (e.g., metal salts of fatty acids, such as the metal salts of stearic acid, and dihydrotalcite), polymer processing additives (e.g., fluoropolymer polymer processing additives), polymer cross-linking agents, slip agents (e.g., fatty acid amide compounds derived from the reaction between a fatty acid and ammonia or an amine-containing compound), fatty acid ester compounds (e.g., fatty acid ester compounds derived from the reaction between a fatty acid and a hydroxyl-containing compound, such as glycerol, diglycerol, and combinations thereof), and combinations of the foregoing.

As noted above, the thermoplastic polymer composition of the invention can contain other nucleating agents in addition to those compounds conforming to the structure of Formula (I). Suitable nucleating agents include, but are not limited to, 2,2'-methylene-bis-(4,6-di-tert-butylphenyl)phosphate salts (e.g., sodium 2,2'-methylene-bis-(4,6-di-tert-butylphenyl) phosphate or aluminum 2,2'-methylene-bis-(4,6-di-tert-butylphenyl)phosphate), bicyclo[2.2.1]heptane-2,3-dicarboxylate salts (e.g., disodium bicyclo[2.2.1]heptane-2,3-dicarboxylate or calcium bicyclo[2.2.1]heptane-2,3-dicarboxylate), cyclohexane-1,2-dicarboxylate salts (e.g., calcium cyclohexane-1,2-dicarboxylate, monobasic aluminum cyclohexane-1,2-dicarboxylate, dilithium cyclohexane-1,2-dicarboxylate, or strontium cyclohexane-1,2-dicarboxylate), glycerolate salts (e.g., zinc glycerolate), phthalate salts (e.g., calcium phthalate), phenylphosphonic acid salts (e.g., calcium phenylphosphonate), and combinations thereof. For the bicyclo[2.2.1]heptane-2,3-dicarboxylate salts and the cyclohexane-1,2-dicarboxylate salts, the carboxylate moieties can be arranged in either the cis- or trans-configuration, with the cis-configuration being preferred.

As noted above, the thermoplastic polymer composition of the invention can also contain a clarifying agent. Suitable clarifying agents include, but are not limited to, trisamides and acetal compounds that are the condensation product of a polyhydric alcohol and an aromatic aldehyde. Suitable trisamide clarifying agents include, but are not limited to, amide derivatives of benzene-1,3,5-tricarboxylic acid, derivatives of N-(3,5-bis-formylamino-phenyl)-formamide (e.g., N-[3,5-bis-(2,2-dimethyl-propionylamino)-phenyl]-2,2-dimethyl-propionamide), derivatives of 2-carbamoyl-malonamide (e.g., N,N'-bis-(2-methyl-cyclohexyl)-2-(2-methyl-cyclohexylcarbamoyl)-malonamide), and combinations thereof. As noted above, the clarifying agent can be an acetal compound that is the condensation product of a polyhydric alcohol and an aromatic aldehyde. Suitable polyhydric alcohols include acyclic polyols such as xylitol and sorbitol, as well as acyclic deoxy polyols (e.g., 1,2,3-trideoxynonitol or 1,2,3-trideoxynon-1-enitol). Suitable aromatic aldehydes typically contain a single aldehyde group with the remaining positions on the aromatic ring being either unsubstituted or substituted. Accordingly, suitable aromatic aldehydes include benzaldehyde and substituted benzaldehydes (e.g., 3,4-dimethyl-benzaldehyde or 4-propyl-benzaldehyde). The acetal compound produced by the aforementioned reaction can be a mono-acetal, di-acetal, or tri-acetal compound (i.e., a compound containing one, two, or three acetal groups, respectively), with the di-acetal compounds being preferred. Suitable acetal-based clarifying agents include, but are not limited to, the clarifying agents disclosed in U.S. Pat. Nos. 5,049,605; 7,157,510; and 7,262,236.

The thermoplastic polymer composition of the invention can be produced by any suitable method or process. For example, the thermoplastic polymer composition can be produced by simple mixing of the individual components of the thermoplastic polymer composition (e.g., thermoplastic polymer, nucleating agent, and other additives, if any). The thermoplastic polymer composition can also be produced by mixing the individual components under high shear or high intensity mixing conditions. The thermoplastic polymer composition of the invention can be provided in any form suitable for use in further processing to produce an article of manufacture from the thermoplastic polymer composition. For example, the thermoplastic polymer compositions can be provided in the form of a powder (e.g., free-flowing powder), flake, pellet, prill, tablet, agglomerate, and the like.

The thermoplastic polymer composition of the invention is believed to be useful in producing thermoplastic polymer articles of manufacture. The thermoplastic polymer composition of the invention can be formed into a desired thermoplastic polymer article of manufacture by any suitable technique, such as injection molding (e.g., thin-wall injection molding, multicomponent molding, overmolding, or 2K molding), blow molding (e.g., extrusion blow molding, injection blow molding, or injection stretch blow molding), extrusion (e.g., fiber extrusion, tape (e.g., slit tape) extrusion, sheet extrusion, film extrusion, cast film extrusion, pipe extrusion, extrusion coating, or foam extrusion), thermoforming, roto-molding, film blowing (blown film), film casting (cast film), compression molding, extrusion compression molding, extrusion compression blow molding, and the like. Thermoplastic polymer articles made using the thermoplastic polymer composition of the invention can be comprised of multiple layers (e.g., multilayer blown or cast films or multilayer injection molded articles), with one or any suitable number of the multiple layers containing a thermoplastic polymer composition of the invention.

The thermoplastic polymer composition of the invention can be used to produce any suitable article of manufacture. Suitable articles of manufacture include, but are not limited to, medical devices (e.g., pre-filled syringes for retort applications, intravenous supply containers, and blood collection apparatus), food packaging, liquid containers (e.g., containers for drinks, medications, personal care compositions, shampoos, and the like), apparel cases, microwavable articles, shelving, cabinet doors, mechanical parts, automobile parts, sheets, pipes, tubes, rotationally molded parts, blow molded parts, films, fibers, and the like.

The addition of the heterogeneous nucleating agents described above has consistently been demonstrated to nucleate the thermoplastic polymer (e.g., polyolefin, such as polyethylene), as observed, for example, through an increase in the peak polymer recrystallization temperature of the polymer. Further, the addition of the nucleating agent has been observed to favorably improve certain physical properties of the thermoplastic polymer, such as the haze, tear strength (either absolute tear strength or the balance between tear strength in the machine and transverse directions), stiffness, and barrier properties. When the thermoplastic polymer composition is used to produce an article, the physical property effects of the nucleating agent on the polymer can be improved by manipulating the characteristic process time (T) and/or selecting a polymer exhibiting an appropriate average relaxation time ($\lambda$). In this context, the characteristic process time (T) is the time during which the molten polymer is subjected to strain, which results in stress (e.g., extensional melt stress) in the polymer melt. The average relaxation time ($\lambda$) is a characteristic of the polymer and is a measure of the time it takes the polymer melt to relieve stress. The average relaxation time ($\lambda$) is dependent upon, inter alia, the molecular weight of the polymer, the molecular weight distribution of the polymer, and the degree of branching in the polymer. For example, it is known that $\lambda$ is proportional to the molecular weight of the polymer, with higher molecular weights leading to longer relaxation times. Further, most commercial polyolefins are more or less polydisperse, with the degree of polydispersity typically indicated by Mw/Mn as determined by GPC. This polydispersity inherently yields a series of molecular weight-dependent relaxation times, though many techniques can only measure a single average relaxation time for such polydisperse systems. The polydispersity of the polymer, and the series of molecular weight-dependent relaxation times and/or average relaxation time, can be intentionally further broadened or manipulated by making bimodal blends, as described above.

Many thermoplastic polymers, such as polyethylene, crystallize by chain folding, producing crystalline lamellae interspersed with an amorphous phase. In processes in which the molten polymer is subject to relatively little strain, the polymer chains in the polymer melt are not well aligned and the polymer melt (e.g., polyethylene melt) cools until sufficient chain alignment occurs to spontaneously initiate crystalline lamellae growth. When this spontaneous lamellae growth occurs, the nucleation density is relatively low, and the growing lamellae travel further before impinging on each other. This allows the lamellae to begin to change their direction or splay out, with the extreme of splaying being the formation of full spherulites. Because of the relatively long time it takes for self-nucleation to occur under these conditions, a nucleating agent (such as that described in this application) added to the polymer melt will have the opportunity to control a larger proportion of the lamellae growth. And with a larger proportion of the lamellae being formed by the nucleating agent, the nucleating agent will effectively influence the physical properties of the polymer and article.

Certain processes, such as film blowing, can impart significant extensional strain to the polymer melt in the machine direction (i.e., the direction in which the molten polymer exits the die). The resulting stress causes polymer chains to uncoil from their entropic random coil, resulting in extended polymer chain alignments in the machine direction. If this orientation persists as the polymer melt cools, some of these aligned, extended chain segments can crystallize from the melt to form relatively long fibrils. The fibrils are very effective in nucleating chain-folding lamellae growth. The lamellae form and begin to grow perpendicular to the fibril axis and more or less radially around the fibrils. Since the nucleation density is higher, growing lamellae may impinge on each other before significant splaying begins. This process is referred to herein as "stress-induced fibril self-nucleation." Under certain conditions as described below, this stress-induced fibril self-nucleation can become prominent in the polymer (e.g., a polyethylene polymer). Thus, any heterogeneous nucleating agent must compete with this stress-induced fibril self-nucleation, making the nucleating agent less effective at favorably influencing the physical properties of the polymer and the article. The effects of $\lambda$ and T on stress-induced fibril self-nucleation and the effectiveness of nucleating agents are described below.

Assuming a constant T, a shorter $\lambda$ means that more stress relaxation occurs and less polymer chain orientation (e.g., polymer chain orientation induced by the extensional strain on the polymer melt) remains at the end of T. Under such conditions, stress-induced fibril self-nucleation will be less prominent in the polymer, and a nucleating agent will be more effective at controlling lamellae growth and influencing the physical properties of the polymer and the article. At the same T, a longer $\lambda$ means that less stress relaxation occurs and more polymer chain orientation remains at the end of T. Under this set of conditions, stress-induced fibril self-nucleation will be more prominent in the polymer, and a nucleating agent will be less effective at controlling lamellae growth and influencing the physical properties of the polymer and the article.

In assessing the effects of $\lambda$ and T on stress-induced fibril self-nucleation and the effectiveness of heterogeneous nucleating agents (such as those described herein) in, for example, blown film processes, it can be instructive to consider the ratio of $\lambda$ to T ($\lambda$/T), which will be referred to hereinafter as the "Fabrication Time Ratio" (FTR). The FTR is of the same form as and roughly analogous to the Deborah number (De). As illustrated by the foregoing discussion, a lower FTR means that less stress-induced fibril self-nucleation will occur in the polymer, making a nucleating agent more effective at influencing the physical properties. And a higher FTR means that more stress-induced fibril self-nucleation will occur in the polymer, making a nucleating agent less effective at influencing the physical properties. Since the process times of most commercial processes can only be varied within a relatively narrow window, the more viable option for changing the FTR to improve or optimize the effect of the nucleating agent is to change $\lambda$, which is done by varying the polymer properties. More specifically, for a given process, the effect of the nucleating agent can be optimized to achieve the desired result by varying the polymer properties and $\lambda$ to better match the process time T.

Thus, if one is unable to achieve the desired degree of nucleation effects (e.g., improved barrier properties or increased tear strength) using a given nucleating agent and polymer in a process, one can improve the results by selecting a different polymer having a shorter $\lambda$. For example, one can select a bimodal polymer containing a first fraction having a relatively low Melt Index (which is typically indicative of a higher molecular weight and therefore a longer $\lambda$) and a second fraction having a relatively high Melt Index (which is typically indicative of a lower molecular weight and therefore a shorter $\lambda$). In this system, the higher Melt Index fraction may provide a $\lambda$ for the entire polymer that results in less stress-induced fibril self-nucleation and improved response to the heterogeneous nucleating agent. Alternatively, the nucleating agent may only nucleate the higher Melt Index fraction (due to the shorter $\lambda$ exhibited by the fraction), leaving the lower Melt Index fraction to undergo stress-induced fibril self-nucleation in basically the same manner as if no nucleating agent were present. Regardless of the mechanism at work, the end result is that the nucleating agent controls more lamellae growth in the polymer and exerts an increased influence on the physical properties of the polymer. While the foregoing example describes the use of bimodal polymers, the same effects can be achieved using multimodal polymers and physical blends of distinct polymers because each of these alternatives also provides a means to reduce $\lambda$. Further, similar improvements can be achieved by selecting a polymer having a narrower molecular weight distribution (as indicated by a lower melt flow ratio). A narrower molecular weight distribution typically indicates the absence of a higher molecular weight "tail" or fraction in the polymer that might increase $\lambda$ for the polymer. Also, similar improvements can be achieved by selecting a polymer having less long chain branching, since long chain branching can result in melt entanglement that can increase $\lambda$.

In a second embodiment, the invention provides a compound conforming to the structure of Formula (C)

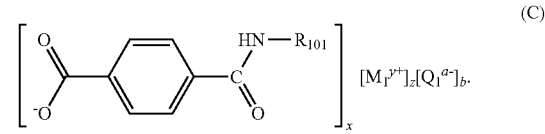

In the structure of Formula (C), $R_{101}$ is selected from the group consisting of a cyclopentyl group and moieties conforming to the structure of Formula (CI). The structure of Formula (CI) is

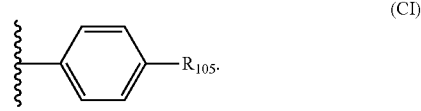

In the structure of (CI), $R_{105}$ is selected from the group consisting of hydrogen and halogens. The variable x is a positive integer; each $M_1$ is a metal cation; y is the valence of the cation; and z is a positive integer. The variable b is zero or a positive integer. When b is a positive integer, each $Q_1$ is a negatively-charged counterion and a is the valence of the negatively-charged counterion. The values of x, y, z, a, and b satisfy the equation x+(ab)=yz.

$M_1$ can be any of the cations described above as being suitable for the compound conforming to the structure of Formula (I), including those cations noted as being preferred for the structure of Formula (I). In a preferred embodiment, $M_1$ is a cation of a metal selected from the group consisting of alkali metals and alkaline earth metals. In another preferred embodiment, $M_1$ is a cation of a metal selected from the group consisting of alkali metals. In a preferred embodiment, $M_1$ is a lithium cation. $Q_1$, if present, can be any of the anions described above as being suitable for the compound conforming to the structure of Formula (I), including those anions noted as being preferred for the structure of Formula (I).

In a preferred embodiment, $R_{101}$ is a cyclopentyl group. The cyclopentyl group can be unsubstituted or substituted. The substituted cyclopentyl group can conform to the structure of Formula (AC) above. Preferably, the cyclopentyl group is unsubstituted. In a more specific embodiment, $R_{101}$ is a cyclopentyl group, the variable x is 1, $M_1$ is a lithium cation, y is 1, z is 1, and b is zero.

In another preferred embodiment, $R_{101}$ is a moiety conforming to the structure of Formula (CI). In a more specific embodiment, $R_{101}$ is a moiety conforming to the structure of Formula (CI), and $R_{105}$ is hydrogen. In another specific embodiment, $R_{101}$ is a moiety conforming to the structure of Formula (CI), $R_{105}$ is hydrogen, x is 1, $M_1$ is a lithium cation, y is 1, z is 1, and b is zero. In another specific embodiment, $R_{101}$ is a moiety conforming to the structure of Formula (CI), and $R_{105}$ is a halogen, preferably bromine. In a more specific embodiment, $R_{101}$ is a moiety conforming to the structure of Formula (CI), $R_{105}$ is bromine, x is 1, $M_1$ is a lithium cation, y is 1, z is 1, and b is zero.

In a series of additional embodiments, the compound of this second embodiment can be used as a nucleating agent for a thermoplastic polymer as described above in the first embodiment of the invention. In particular, these additional embodiments include thermoplastic polymer compositions comprising a thermoplastic polymer, preferably a polyolefin polymer (e.g., a polyethylene polymer), and one or more of the specific compounds described in the preceding paragraphs.

In a third embodiment, the invention provides a compound conforming to the structure of Formula (CX)

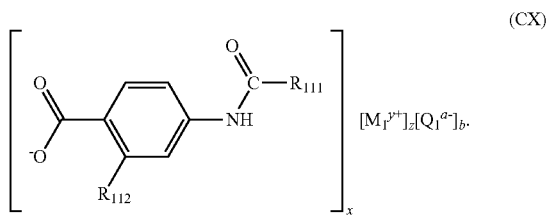

(CX)

In the structure of (CX), $R_{111}$ is selected from the group consisting of a cyclopentyl group and moieties conforming to the structure of Formula (CXI); and $R_{112}$ is selected from the group consisting of hydrogen and hydroxy. The structure of Formula (CXI) is

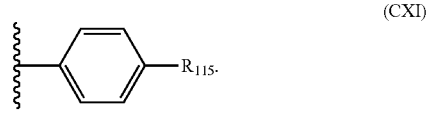

(CXI)

In the structure of (CXI), $R_{115}$ is selected from the group consisting of hydrogen, a halogen, methoxy, and phenyl. The variable x is a positive integer; each $M_1$ is a metal cation; y is the valence of the cation; and z is a positive integer. The variable b is zero or a positive integer. When b is a positive integer, each $Q_1$ is a negatively-charged counterion and a is the valence of the negatively-charged counterion. The values of x, y, z, a, and b satisfy the equation x+(ab)=yz. Further, if $R_{115}$ is hydrogen, then $R_{112}$ is hydrogen, x is 1, $M_1$ is a lithium cation, y is 1, z is 1, and b is zero. Also, if $R_{115}$ is a methoxy group, then $R_{112}$ is a hydroxy group.

$M_1$ can be any of the cations described above as being suitable for the compound conforming to the structure of Formula (I), including those cations noted as being preferred for the structure of Formula (I). In a preferred embodiment, $M_1$ is a cation of a metal selected from the group consisting of alkali metals and alkaline earth metals. In another preferred embodiment, $M_1$ is a cation of a metal selected from the group consisting of alkali metals. In a preferred embodiment, $M_1$ is a lithium cation. $Q_1$, if present, can be any of the anions described above as being suitable for the compound conforming to the structure of Formula (I), including those anions noted as being preferred for the structure of Formula (I).

In a preferred embodiment, $R_{111}$ is a cyclopentyl group. The cyclopentyl group can be unsubstituted or substituted. The substituted cyclopentyl group can conform to the structure of Formula (AC) above. Preferably, the cyclopentyl group is unsubstituted. In a more specific embodiment, $R_{111}$ is a cyclopentyl group, the variable x is 1, $M_1$ is a lithium cation, y is 1, z is 1, and b is zero.

In another preferred embodiment, $R_{111}$ is a moiety conforming to the structure of Formula (CXI). In a more specific embodiment, $R_{111}$ is a moiety conforming to the structure of Formula (CXI), and $R_{115}$ is hydrogen. In another more specific embodiment, $R_{111}$ is a moiety conforming to the structure of Formula (CXI), and $R_{115}$ is a methoxy group. In yet another specific embodiment, $R_{111}$ is a moiety conforming to the structure of Formula (CXI), $R_{115}$ is a methoxy group, x is 1, $M_1$ is a lithium cation, y is 1, z is 1, and b is zero. In another more specific embodiment, $R_{111}$ is a moiety conforming to the structure of Formula (CXI), and $R_{115}$ is a halogen, preferably chlorine. In a yet more specific embodiment, $R_{111}$ is a moiety conforming to the structure of Formula (CXI), $R_{115}$ is a halogen, preferably chlorine, and $R_{112}$ is hydrogen. In another more specific embodiment, $R_{111}$ is a moiety conforming to the structure of Formula (CXI), $R_{115}$ is chlorine, $R_{112}$ is hydrogen, and $M_1$ a cation of a metal selected from the group consisting of alkali metals, preferably sodium. In a more specific embodiment, $R_{111}$ is a moiety conforming to the structure of Formula (CXI), $R_{115}$ is chlorine, $R_{112}$ is hydrogen, x is 1, $M_1$ a sodium cation, y is 1, z is 1, and b is zero.

In a series of additional embodiments, the compound of this third embodiment can be used as a nucleating agent for a thermoplastic polymer as described above in the first embodiment of the invention. In particular, these additional embodiments include thermoplastic polymer compositions comprising a thermoplastic polymer, preferably a polyolefin polymer (e.g., a polyethylene polymer), and one or more of the specific compounds described in the preceding paragraphs.

In a fourth embodiment, the invention provides a compound conforming to the structure of Formula (CXX)

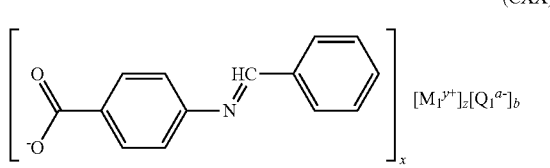

(CXX)

In the structure of (CXX), the variable x is a positive integer. Each $M_1$ is a cation of a metal selected from the group consisting of alkali metals, alkaline earth metals, and zinc; y is the valence of the cation; and z is a positive integer. The variable b is zero or a positive integer. When b is a positive integer, each $Q_1$ is a negatively-charged counterion and a is the valence of the negatively-charged counterion. The values of x, y, z, a, and b satisfy the equation x+(ab)=yz.

In a preferred embodiment, $M_1$ is a cation of a metal selected from the group consisting of alkali metals and alkaline earth metals. In another preferred embodiment, $M_1$ is a cation of a metal selected from the group consisting of alkali metals. In a more specific embodiment, $M_1$ is a lithium cation. In another specific embodiment, x is 1, $M_1$ is a lithium cation, y is 1, z is 1, and b is zero.

In a series of additional embodiments, the compound of this fourth embodiment can be used as a nucleating agent for a thermoplastic polymer as described above in the first embodiment of the invention. In particular, these additional embodiments include thermoplastic polymer compositions comprising a thermoplastic polymer, preferably a polyolefin polymer (e.g., a polyethylene polymer), and one or more of the specific compounds described in the preceding paragraphs.

In another embodiment, the invention provides an additive composition comprising a nucleating agent as described above and an acid scavenger compound. The nucleating agent present in the composition can be any one or more of the nucleating agent compounds described above, such as a compound conforming to the structure of Formula (I), a compound conforming to the structure of Formula (C), a compound conforming to the structure of Formula (CX), a compound conforming to the structure of Formula (CXX), or any suitable mixture of such compounds. Preferably, the nucleating agent in the additive composition is selected from the group consisting of compounds conforming to the structure of Formula (CX). More preferably, the nucleating agent is a compound conforming to the structure of Formula (CX) in which $R_{112}$ is hydrogen, $R_{111}$ is a moiety conforming to the structure of Formula (CXI), and $R_{115}$ is a halogen. In a more specific preferred embodiment, the nucleating agent is a compound conforming to the structure of Formula (CX) in which $R_{112}$ is hydrogen, $R_{111}$ is a moiety conforming to the structure of Formula (CXI), $R_{115}$ is chlorine, $M_1$ is a sodium cation, x is 1, y is 1, z is 1, and b is 0.

Preferably, the acid scavenger is selected from the group consisting of metal salts of fatty acids and synthetic hydrotalcite compounds. Suitable metal salts of fatty acids include, but are not limited to, the metal salts of $C_{12}$-$C_{22}$ fatty acids, such as stearic acid. In a preferred embodiment, the acid scavenger is selected from the group consisting of the zinc, potassium, and lanthanum salts of stearic acid. Suitable synthetic hydrotalcite compounds include, but are not limited to, DHT-4A acid scavenger sold by Kyowa Chemical Industry Co., Ltd.

The nucleating agent and the acid scavenger can be present in the additive composition in any suitable amounts. For example, the nucleating agent and the acid scavenger can be present in the additive composition in a ratio (nucleating agent to acid scavenger) of about 10:1 to about 1:10 based on the weight of the nucleating agent and the acid scavenger in the composition. More preferably, the nucleating agent and the acid scavenger are present in the additive composition in a ratio (nucleating agent to acid scavenger) of about 4:1 to about 1:4, about 3:1 to about 1:3, about 1:1 to about 1:4, or about 1:1 to about 1:3 based on the weight of the nucleating agent and the acid scavenger in the additive composition.

Surprisingly, it has been found that the nucleating agent and the acid scavenger synergistically interact when the additive composition described above is added to a thermoplastic polymer. In particular, it has been found that the addition of the acid scavenger can improve the performance of the nucleating agent. For example, the addition of both the nucleating agent and the acid scavenger can improve the physical property enhancements to the polymer beyond those realized when the nucleating agent alone is used. Also, the addition of the acid scavenger can permit one to achieve a desired level of physical property enhancements to the polymer using less nucleating agent than would be required if the nucleating agent were added alone. This synergy is considered especially surprising given the fact that the acid scavenger has not been observed to nucleate the polymer itself. For example, the addition of the acid scavenger alone does not have an appreciable effect on the physical properties of the polymer.

The additive composition described above is intended for incorporation into a thermoplastic polymer, such as the polyethylene and polypropylene polymers described earlier in this application. In particular, it is believed that the additive composition is particularly effective when used in a high density polyethylene polymer. In these polymers, the addition of the additive composition has been observed to significantly lower the machine direction shrinkage, which is indicative of increased machine direction orientation of the crystalline lamellae, and significantly improve the stiffness and heat deflection temperature of the polymer.

The following examples further illustrate the subject matter described above but, of course, should not be construed as in any way limiting the scope thereof.

PREPARATION EXAMPLE EX1

This example demonstrates the preparation of 4-chlorocarbonyl-benzoic acid methyl ester having the following structure

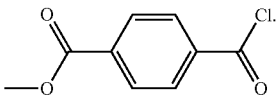

In a 4 L kettle with mechanical stirrer, reflux condenser, addition funnel, thermometer, water bath and hot plate, 438 g dimethyl terephthalate (DMT) and 2700 mL toluene were added. The kettle was heated to about 65° C. to dissolve all the DMT. After dissolution, a potassium hydroxide solution (144.54 g in 700 mL methanol) was added dropwise over 45 minutes. The reaction was stirred at 65° C. for three hours and then the reaction cooled to room temperature overnight. The solid was collected after filtration and washed with 3750 mL toluene at 80° C. The product was filtered again and dried in the oven at 110° C. The yield was 465.9 g (95.3%).

In a 2 L three neck round bottom flask with mechanical stirrer, addition funnel, water bath, thermometer, nitrogen sweep, and hot plate, 130.31 g of the product made in previous step and 1000 mL toluene were added. Then 48 mL of thionyl chloride was added dropwise. After the completion of addition, the mixture was heated to 67° C. for three hours. The reaction cooled to room temperature and was stirred overnight. The contents were filtered to collect the filtrate. The excess solvent was removed by vacuum and 86.52 g of product was obtained (73% yield).

PREPARATION EXAMPLE EX2

This example demonstrates the synthesis of N-cyclopentyl-terephthalamic acid having the following structure

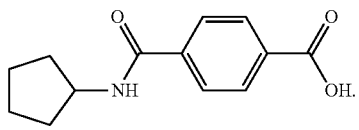

A 2 L round bottom flask was charged with 15.44 g of sodium bicarbonate, 15.75 g of cyclopentyl amine, 0.5 g of triethylamine, and 200 mL of tetrahydrofuran (THF). The flask was chilled in an ice bath, and then a solution of 4-chlorocarbonyl-benzoic acid methyl ester (36.78 g in about 100 mL of THF) was added dropwise to the flask. After addition, the mixture was heated to reflux. The reaction was monitored with infrared spectroscopy (IR) until the peak at 1780 cm$^{-1}$ disappeared. Then the mixture was poured into about 2 L of water and stirred for approximately 20 minutes. The solid product was collected after filtration and dried in the oven at 100° C.

To a 2 L three neck round bottom flask, 21 gram of the product made in the previous step and 150 mL of methanol were added. The mixture was heated to reflux and potassium hydroxide (4.76 g, pre-dissolved in methanol) was added. The reaction was monitored with IR until the peak at 1720 cm$^{-1}$ disappears. Then, 400 mL of water was added, and any insoluble impurities were filtered off. The pH of the filtrate was adjusted to about 2 and a precipitate formed. The solid product was filtered and dried in an oven at 100° C.

PREPARATION EXAMPLE EX3

This example demonstrates the production of the potassium salt of N-cyclopentyl-terephthalamic acid having the following structure

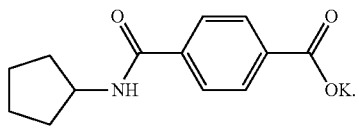

In a beaker, 10 g of N-cyclopentyl-terephthalamic acid was added to 50 mL H$_2$O. Then, 2.41 g of potassium hydroxide was dissolved in a separate beaker with about 20 mL of H$_2$O. The potassium hydroxide solution was added into the N-cyclopentyl-terephthalamic acid slurry and most of the solid dissolved. To remove any undissolved material, the mixture was filtered. The filtrate was collected and the water was evaporated off to yield the product. The product was dried overnight in an oven at 110° C.

PREPARATION EXAMPLE EX4

This example demonstrates the production of N-phenyl-terephthalamic acid having the following structure

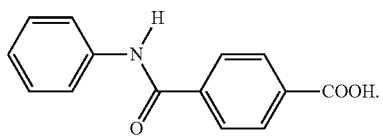 [SMILES: O=C(O)c1ccc(C(=O)Nc2ccccc2)cc1]

To a 1 L three neck round bottom flask with magnetic stirrer, addition funnel, ice bath, nitrogen sweep, scrubber and hot plate, 93.13 g of aniline, 42.30 g of sodium bicarbonate, 0.5 g of triethylamine, and 300 mL of tetrahydrofuran (THF) were added. The mixture was cooled to below 10° C. and then a solution of 100 g of 4-chlorocarbonyl-benzoic acid methyl ester in 100 mL of tetrahydrofuran was added dropwise. The temperature was maintained at about 10° C. during addition. After addition, the mixture was heated to reflux and monitored to completion of reaction by IR (disappearance of peak at 1780 cm$^{-1}$). After completion, the reaction was diluted to 2 L with cold deionized (DI) water and stirred for approximately 20 minutes. The solid product was filtered and dried in an oven at 110° C. After drying, 105.6 g of product was obtained (82.2% yield).

In a 1 L Erlenmeyer flask with magnetic stir bar and stir plate, 15.94 g of the product made in previous step and 200 mL of methanol were added. Then, potassium hydroxide (3.87 g) that was pre-dissolved in methanol was added. The reaction was monitored by IR (disappearance of the peak at about 1720 cm$^{-1}$). After completion, the reaction was diluted with 400 mL water. Solid impurities were removed by filtration and the pH of the filtration was adjusted to about 2. A product precipitated out at this step and was collected by filtration. The product was washed with more DI water wash until neutral, and the product was dried in an oven at 100° C. After drying, 14.47 g of the product was obtained (95% yield).

PREPARATION EXAMPLE EX5

This example demonstrates the production of the lithium salt of N-phenyl-terephthalamic acid having the following structure.

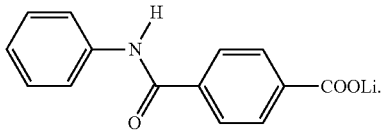

In a 500 mL Erlenmeyer flask with magnetic stir bar and stir plate, 13.3 g of N-phenyl-terephthalamic acid and 200 mL of water were added. The mixture was heated to near boiling and then an aqueous solution of lithium hydroxide (containing 1.49 g of anhydrous lithium hydroxide) was added. The reaction was monitored by IR (disappearance of the peak at 1677 cm$^{-1}$). After completion, the reaction was cooled down and filtered to collect the product. The product was dried in an oven at 110° C. and 11.56 g of product was obtained.

PREPARATION EXAMPLE EX6

This example demonstrates the production of 4-(4-bromo-benzoylamino)benzoic acid having the following structure

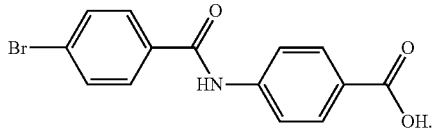

In a 1 L three neck round bottom flask, 40 g of 4-aminobenzoic acid and 400 mL of dioxane were added. The mixture was stirred until the acid dissolved. Then, 4-bromobenzoyl chloride solution (32.04 g in 100 mL dioxane) was added dropwise to the reaction. After addition, the reaction was stirred overnight and then filtered to collect the solid. The solid was washed with boiling water and then cold DI water until the pH was neutral. After drying, the product was obtained with 99.6% yield.

PREPARATION EXAMPLE EX7

This example demonstrates the production of the potassium salt of 4-(4-bromo-benzoylamino)benzoic acid having the following structure

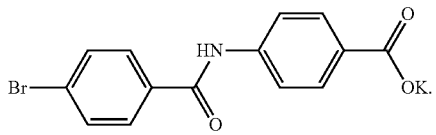

In a beaker, 25 g of 4-(4-bromo-benzoylamino)benzoic acid and 200 mL of DI water were added. The mixture was stirred until it formed a uniform slurry. Then, a potassium hydroxide solution (4.4 g in 100 mL water) was added. The reaction was stirred overnight, and the pH value dropped to 10.6. The solid product was filtered and dried in an oven at 110° C.

PREPARATION EXAMPLE EX8

This example demonstrates the production of the lithium salt of 4-(4-bromo-benzoylamino)benzoic acid having the following structure

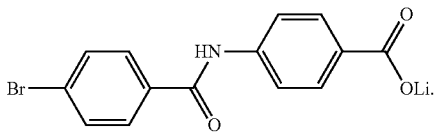

In a beaker, 3 grams of 4-(4-bromo-benzoylamino)benzoic acid was dispersed into about 50 mL of water with stirring. Then a lithium hydroxide monohydrate solution (0.39 g in 50 mL of $H_2O$) was added to the slurry. The reaction was stirred overnight and then the solid was collected through filtration. The filtrate was washed with DI water and then dried in an oven at 110° C.

PREPARATION EXAMPLE EX9

This example demonstrates the production of the calcium salt of 4-(4-bromo-benzoylamino)benzoic acid having the following structure

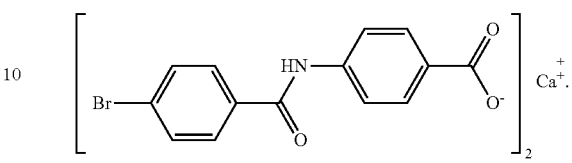

In a beaker, 3 grams of 4-(4-bromo-benzoylamino)benzoic acid was dispersed into about 50 mL of water with stirring. Then, a calcium hydroxide solution (0.35 g in 50 mL water) was added to the slurry. The reaction was stirred over the weekend and then filtered to collect the resulting solid. The filtrate was washed with DI water and then dried in an oven at 110° C.

PREPARATION EXAMPLE EX10

This example demonstrates the production of 4-(cyclopropanecarbonyl-amino)-benzoic acid having the following structure

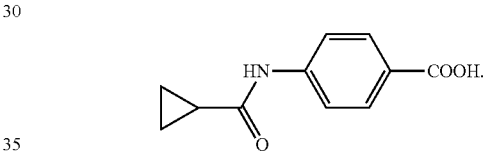

In a three neck flask, 20.3 g of sodium carbonate was dispersed in 80 mL of THF under N2. While stirring, 13.1 g of 4-aminibenzoic acid dispersion (in 15 mL of THF) and 10.0 g of cyclopropane carbonyl chloride solution (in 15 mL of THF) were separately added dropwise. The reaction was stirred overnight. Next, 10.15 g of sodium carbonate was added and the mixture was stirred for another 3 hours. Then, the THF was evaporated and the reaction mixture was transferred to a 1 L beaker and diluted with 600 mL of water. The pH was adjusted to about 2 with hydrochloric acid to form the product as a precipitate. The mixture was filtered to collect the precipitate, and the precipitate was dried in a vacuum oven.

PREPARATION EXAMPLE EX11

This example demonstrates the production of the lithium salt of 4-(cyclopropanecarbonyl-amino)-benzoic acid having the following structure

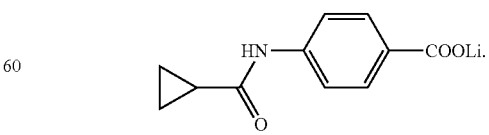

In a beaker, 5 gram of 4-(cyclopropanecarbonyl-amino)-benzoic acid was dispersed in 20 mL of water and then 1.13 g of lithium hydroxide monohydrate was added. After a 20 minute stir, the reaction was concentrated in vaccuo to obtain the product. The product was dried, and the yield was about 2.59 g.

PREPARATION EXAMPLE EX12

This example demonstrates the production of the sodium salt of 4-(Cyclopropanecarbonyl-amino)-benzoic acid having the following structure

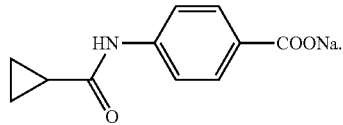

In a beaker, 20 gram of 4-(cyclopropanecarbonyl-amino)-benzoic acid was mixed with 80 mL of water, and then 8.58 g of sodium hydroxide solution (50% in water) was added. After a 20 minute stir, the reaction was concentrated in vaccuo to obtain the product.

PREPARATION EXAMPLE EX13

This example demonstrates the production of the lithium salt of 4-stilbenecarboxylic acid having the following structure

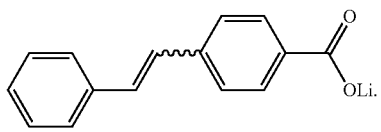

In a beaker, 1 gram of 4-stilbenecarboxylic acid (a mixture of trans and cis isomers) was dispersed in 25 mL of water. Then, 0.19 g of lithium hydroxide monohydrate was dissolved in 25 mL of water and then added to the acid suspension. The reaction was stirred overnight. The solid product was collected by filtration, washed three times with water, and then dried in an oven at 110° C.

PREPARATION EXAMPLE EX14

This example demonstrates the production of 4-(1,3-Dioxo-octahydro-isoindol-2-yl)-2-hydroxy-benzoic acid having the following structure

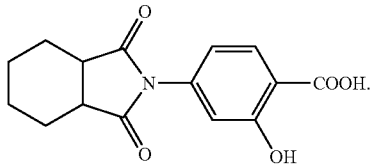 [SMILES: O=C(O)c1ccc(N2C(=O)C3CCCCC3C2=O)cc1O]

In a 500 mL four-neck round bottom flask equipped with temperature probe, heating mantle, agitator, and condenser, 21.20 g of hexahydrophthalic anhydride and 50 mL of acetic acid were charged. At 70° C., the mixture was stirred until uniform and then 21.7 g of 4-aminosalicylic acid and 100 mL of acetic acid were charged. After heating to reflux for 6 hours, the contents were poured into ice cold DI H$_2$O and vacuum filtered to collect the solid. After washing with DI H$_2$O and drying, 33.07 g of product were obtained.

PREPARATION EXAMPLE EX15

This example demonstrates the production of the zinc salt of 4-(1,3-dioxo-octahydro-isoindol-2-yl)-2-hydroxy-benzoic acid having the following structure

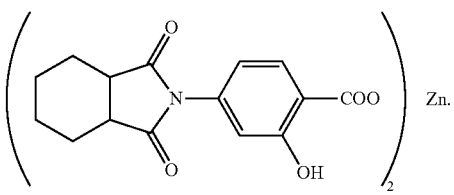

In a beaker, 4-(1,3-dioxo-octahydro-isoindol-2-yl)-2-hydroxy-benzoic acid is suspended in about 100-150 mL of water with a magnetic stirrer. Then, a 25% solution of sodium hydroxide was slowly added until the pH stabilized at 12.5 and the solution became clear. Then, one equivalent of zinc chloride was added (used 1 eq instead of 0.5 because metal ions can coordinate with the meta hydroxy group as well). The products precipitated out, and the mixture was filtered to collect the product.

PREPARATION EXAMPLE EX16

This example demonstrates the production of 4-(2,2-dimethyl-propionylamino)-benzoic acid having the following structure

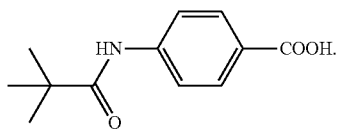

In a three neck round bottom flask with overhead stirring, temperature probe, dry ice bath and reflux condenser, 25 g of 4-aminobenzoic acid, 15.12 g of soda ash, and 200 mL of THF were added. Under stirring, 21.98 g of pivaloyl chloride was added dropwise over 1-1.5 hour. Then, 22.68 g of soda ash was added, and the mixture was heated to 40° C. to drive the reaction to completion. The resulting mixture was diluted with 2 L of DI H$_2$O. The pH of the mixture was adjusted to 2.37 with concentrated hydrochloric acid, and then the mixture was filtered to collect the product.

PREPARATION EXAMPLE EX17

This example demonstrates the production of the potassium salt of 4-(2,2-Dimethyl-propionylamino)-benzoic acid having the following structure

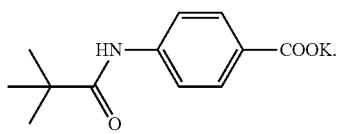

In a beaker, 4-(2,2-dimethyl-propionylamino)-benzoic acid was suspended in about 100-150 mL of water with a magnetic stirrer. Then, a 25% solution of potassium hydroxide was slowly added until the pH stabilized at 12.5 and the solution became clear. The water was stripped off, and the product was obtained.

PREPARATION EXAMPLE EX18

This example demonstrates the production of the calcium salt of 4-(2,2-Dimethyl-propionylamino)-benzoic acid having the following structure.

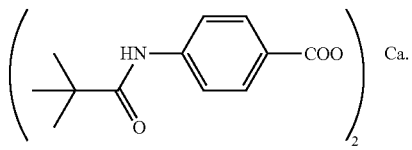

In a beaker, 4-(2,2-Dimethyl-propionylamino)-benzoic acid was suspended in about 100-150 mL of water with a magnetic stirrer. Then, a 25% solution of potassium hydroxide was slowly added until the pH stabilized at 12.5 and the solution became clear. Then, one equivalent of calcium chloride was added. The product precipitated out, and the mixture was filtered to collect the product.

PREPARATION EXAMPLE EX19

This example demonstrates the production of N-4-methoxybenzoyl aminosalicylic acid having the following structure

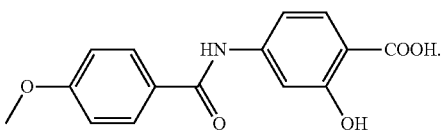

A three-neck round bottom flask was equipped with overhead stirring, temperature probe, dry ice bath, and reflux condenser. Then, 12.36 g of 4-aminosalicylic acid, 16.75 g of soda ash, and 500 mL of tetrahydrofuran were charged into the flask. The mixture was cooled below 10° C. and then 14.85 g of 4-methoxybenzoyl chloride was added dropwise over 1-1.5 hour. The resulting mixture was diluted with 2 L of water and filtered to collect the product.

PREPARATION EXAMPLE EX20

This example demonstrates the production of N-4-methoxybenzoyl aminosalicylic acid having the following structure

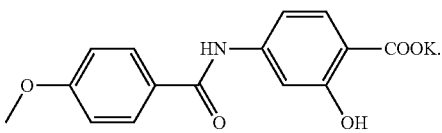

In a beaker, N-4-methoxybenzoyl aminosalicylic acid was suspended in about 100-150 mL of water with a magnetic stirrer. Then, a 25% solution of potassium hydroxide was slowly added until the pH stabilized at 12.5 and the solution became clear. The water was stripped off and the product was obtained.

PREPARATION EXAMPLE EX21

This example demonstrates the production of the lithium salt of N-4-methoxybenzoyl aminosalicylic acid having the following structure

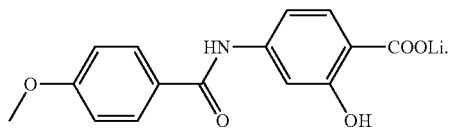

In a beaker, N-4-methoxybenzoyl aminosalicylic acid was suspended in about 100-150 mL of water with a magnetic stirrer. Then, a 25% solution of lithium hydroxide was slowly added until the pH stabilized at 12.5 and the solution became clear. The water was stripped off and the product was obtained.

PREPARATION EXAMPLE EX22

This example demonstrates the production of the sodium salt of N-4-methoxybenzoyl aminosalicylic acid having the following structure

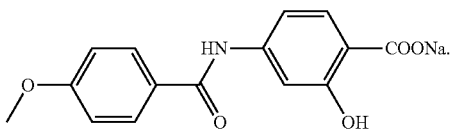

In a beaker, N-4-methoxybenzoyl aminosalicylic acid was suspended in about 100-150 mL of water with a magnetic stirrer. Then, a 25% solution of sodium hydroxide was slowly added until the pH stabilized at 12.5 and the solution became clear. The water was stripped off and the product was obtained.

PREPARATION EXAMPLE EX23

This example demonstrates the production of 4-(cyclobutanecarbonyl-amino)-benzoic acid having the following structure

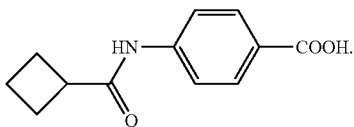 [SMILES: O=C(O)c1ccc(NC(=O)C2CCC2)cc1]

In a flask, 20.3 g of sodium carbonate, 6.3 g of 4-aminobenzoic acid and 80 mL of THF were added. Then, 5 g of cyclobutanecarbonyl chloride (diluted in 15 mL of THF) was added. The reaction was stirred under nitrogen over the weekend and the THF evaporated. The mixture was transferred to a 1 L beaker and dissolved with 400 mL of water. The solution was acidified with hydrochloric acid until the pH was about 2 and the product precipitated out. The product was collected by filtration, then washed with water and dried.

PREPARATION EXAMPLE EX24

This example demonstrates the production of the potassium salt of 4-(cyclobutanecarbonyl-amino)-benzoic acid having the following structure

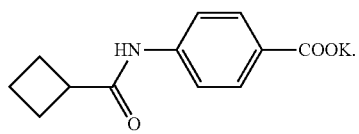

In a beaker, 4-(Cyclobutanecarbonyl-amino)-benzoic acid was suspended in approximately 100-150 mL of water with a magnetic stir bar. Then, a 25% sodium hydroxide solution was added to raise the pH of the solution to about 12.5. A clear solution was obtained, and then the water was stripped away to collect the product as a powder.

PREPARATION EXAMPLE EX25

This example demonstrates the production of 4-(1,3-dioxo-1,3-dihydro-isoindol-2-yl)-benzoic acid having the following structure

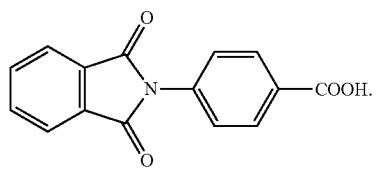 [SMILES: O=C(O)c1ccc(N2C(=O)c3ccccc3C2=O)cc1]

In a 500 mL four-neck round bottom flask equipped with a temperature probe, heating mantle, agitator, and condenser, 25.03 g of phthalic anhydride and 87 mL of acetic acid were charged. At 70° C., the reaction was stirred until a clear solution was obtained. Then, 24.37 g of 4-aminobenzoic acid was charged and the mixture was heated at reflux for 2 hours. Then, 50 more mL of acetic acid was added. The contents were poured into DI $H_2O$. The product was collected by filtration and then washed with DI $H_2O$. After drying, 43.345 g of product was obtained (96% yield).

PREPARATION EXAMPLE EX26

This example demonstrates the production of the lithium salt of 4-(1,3-dioxo-1,3-dihydro-isoindol-2-yl)-benzoic acid having the following structure

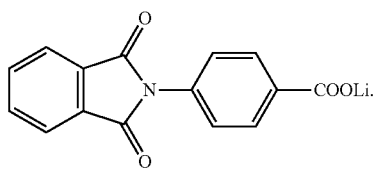

In a 1000 mL beaker equipped with an agitator, 5.03 g of 4-(1,3-Dioxo-1,3-dihydro-isoindol-2-yl)-benzoic acid and 100 mL of DI $H_2O$ were charged. Lithium hydroxide was charged into the beaker and the mixture stirred until all the acid was in solution. If the acid was not completely dissolved, lithium hydroxide in 0.1 g increments was added until the acid fully dissolved. Rotary evaporation was used to recover the product.

PREPARATION EXAMPLE EX27

This example demonstrates the production of the sodium salt of 4-(1,3-Dioxo-1,3-dihydro-isoindol-2-yl)-benzoic acid having the following structure

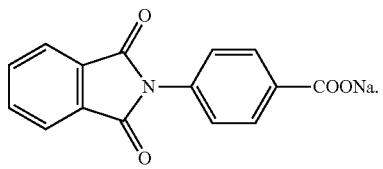

In a 1000 mL beaker equipped with an overhead agitator, 4-(1,3-dioxo-1,3-dihydro-isoindol-2-yl)-benzoic acid and 100 mL of DI $H_2O$ were added. The solution was stirred and a 25% sodium hydroxide solution was slowly added until all the acid was in solution. The water was removed by rotary evaporation to recover the product.

PREPARATION EXAMPLE EX28

This example demonstrates the production of N-cyclobutyl-terephthalamic acid methyl ester having the following structure

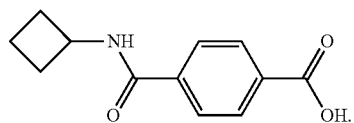

In a three-neck round bottom flask, 14.8 g of sodium carbonate and 50 mL of tetrahydrofuran were added. 5 g of cyclobutylamine was then added. Next, 11.59 g of 4-carbonylchloride methylbenzoate (diluted in 30 mL of tetrahydrofuran) was added dropwise. The reaction was stirred overnight at room temperature. The reaction mixture was then transferred to a beaker and mixed with 200 mL of water. The mixture was acidified with 1 M hydrochloric acid. Then, the mixture was transferred to a separation funnel and extracted with ethyl acetate three times (80 mL each). The organic phase was concentrated to collect the product.

The product obtained in the prior step was mixed with 200 mL of water and then heated to 80° C. A 50% solution of sodium hydroxide was added during the course of heating to keep the pH above 12. After 4 hours, the reaction was acidified to a pH of about 2 and the product precipitated out. The product was separated by filtration.

PREPARATION EXAMPLE EX29

This example demonstrates the production of the lithium salt of N-cyclobutyl-terephthalamic acid having the following structure

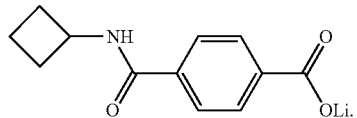

In a beaker, 300 mg of N-cyclobutyl-terephthalamic acid was dispersed in about 40 mL of water. Lithium hydroxide was slowly added until the pH was about 12. Then, the solution was concentrated to obtain the desired product.

PREPARATION EXAMPLE EX30

This example demonstrates the production of N-cyclopropyl-terephthalamic acid having the following structure

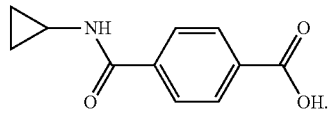 [SMILES: O=C(O)c1ccc(C(=O)NC2CC2)cc1]

In a flask, 9.3 g of sodium carbonate, 5 g of cyclopropylamine, and 80 mL of tetrahydrofuran were added. Then, 16.43 g of 4-chlorocarbonyl-benzoic acid methyl ester was diluted in 30 mL of THF and then added dropwise to the reaction. The reaction was stirred overnight. The product was from the mixture with 400 mL of water. The product was collected and dried, about 18 grams were obtained.

In a flask, 18 g of the product obtained in the previous step was mixed with 200 mL of water and then heated to 80° C. A 50% solution of sodium hydroxide was added during the course of heating to keep the pH above 12. After 4 hours, the reaction was acidified to a pH of about 2 and the product precipitated out. The solution was filtered to obtain the product.

PREPARATION EXAMPLE EX31

This example demonstrates the production of the lithium salt of N-cyclopropyl-terephthalamic acid having the following structure

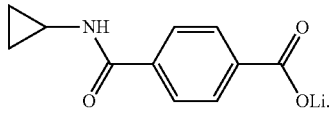

In a beaker, 2.46 g of wet N-cyclopropyl-terephthalamic acid was mixed with 100 mL water and then lithium hydroxcide monohydrate was added until the pH was 12. The reaction was stirred for 20 minutes and was concentrated to yield the product.

PREPARATION EXAMPLE EX32

This example demonstrates the production of the calcium salt of N-cyclopropyl-terephthalamic acid having the following structure

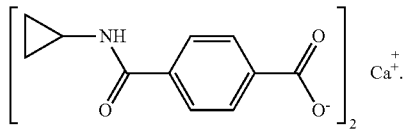

In a beaker, 2.51 g of N-Cyclopropyl-terephthalamic acid was mixed with 50 mL water. Then, a 50% solution of sodium hydroxide was added until the pH was 12. The reaction was stirred for 20 minutes. Then 3.52 g of calcium chloride dihydrate was added to the solution to form the product. The product was collected by filtration and dried in an oven.

PREPARATION EXAMPLE EX33

This example demonstrates the production of the zinc salt of N-cyclobutyl-terephthalamic acid having the following structure

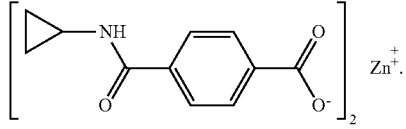

In a beaker, 2.51 g of N-cyclopropyl-terephthalamic acid was mixed with 50 mL of water. Then, a 50% solution of sodium hydroxide was added until the pH was 12. The reaction was stirred for 20 minutes. Then, 3.27 g of zinc chloride was added to the solution to form the product. The product was collected by filtration and dried in an oven.

PREPARATION EXAMPLE EX34

This example demonstrates the production of 4-(4-methoxy-benzoylamino)benzoic acid having the following structure

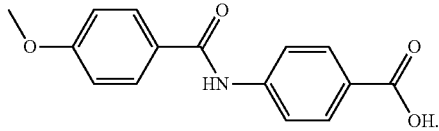 [SMILES: COc1ccc(C(=O)Nc2ccc(C(=O)O)cc2)cc1]

In a 1 L three-neck flask equipped with an overhead stirrer, temperature probe, dry ice bath and a reflux condenser, 25 g of 4-aminobenzoic acid, 45.39 g of soda ash, and 200 mL of tetrahydrofuran were added. With stirring, 31.10 g of 4-methoxyebzoyl chloride was added dropwise over a 1-1.5 hour period. The temperature was kept below 10° C. during addition. After completion of the reaction, the mixture was diluted with 2 L of water. The pH was lowered to about 2 with hydrochloric acid to precipitate the product. The product was collected by filtration and dried in an oven.

PREPARATION EXAMPLE EX35

This example demonstrates the production of the sodium salt of 4-(4-methoxy-benzoylamino)benzoic acid having the following structure

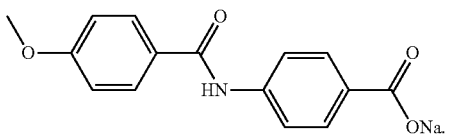

In a beaker, 24 g of 4-(4-methoxy-benzoylamino)benzoic acid was mixed with 200 mL of water. Then, a 50% solution of sodium hydroxide was slowly added until a stable pH value of 12 was obtained. The solution was concentrated in vaccuo to provide the sodium salt of 4-(4-methoxy-benzoylamino) benzoic acid.

PREPARATION EXAMPLE EX36

This example demonstrates the production of the lithium salt of 4-(4-methoxy-benzoylamino)benzoic acid having the following structure

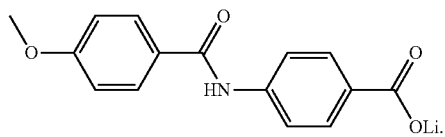

In a beaker, 6 g of 4-(4-methoxy-benzoylamino)benzoic acid was mixed with 100 mL of water and lithium hydroxide monohydrate was slowly added until the pH stabilized at 12. The reaction was stirred for 20 minutes and then was concentrated in vaccuo to provide the product.

PREPARATION EXAMPLE EX37

This example demonstrates the production of N-cycloheptyl-terephthalamic acid having the following structure

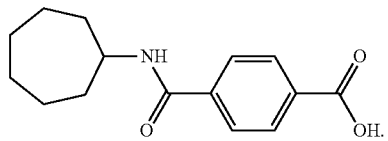 [SMILES: O=C(O)c1ccc(C(=O)NC2CCCCCC2)cc1]

A 1 L round bottom flask was charged with 9.3 g of sodium bicarbonate, 5 g of cycloheptylamine, and 80 mL of tetrahydrofuran (THF). The flask was chilled with an ice bath. Then, a solution of 4-chlorocarbonyl-benzoic acid methyl ester (8.32 g in about 30 mL of THF) was added dropwise to the flask. After the addition, the reaction was heated to reflux. The reaction was monitored with IR until the peak at 1780 cm$^{-1}$ disappeared. Then the mixture was poured into about 400 mL of water and stirred for about 20 minutes. The product was collected by filtration and dried in an oven at 100° C.

In a flask, 9.1 g of the product from the previous step was mixed with 200 mL of water. A 50% NaOH solution was added until the pH was about 12. The reaction was heated to 80° C., stirred for 4 hours, and the pH was maintained at 12 during the reaction. After thin layer chromatography showed the completion of the reaction, the pH was adjusted to 2 to precipitate the product. The product was filtered and washed.

PREPARATION EXAMPLE EX38

This example demonstrates the production of the sodium salt of N-cycloheptyl-terephthalamic acid having the following structure

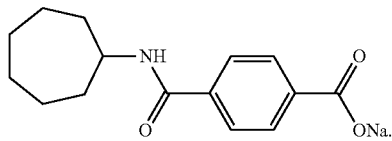

In a flask 8.8 g of N-Cycloheptyl-terephthalamic acid was mixed with 200 mL of water and a 50% solution of sodium hydroxide was added slowly until the pH stabilized at 12. For 20 more minutes, the solution was stirred and then was concentrated in vaccuo to yield the product.

PREPARATION EXAMPLE EX39

This example demonstrates the production of 4-(1,3-Dioxo-1H,3H-benzo[de]isoquinolin-2-yl)-2-hydroxy-benzoic acid having the following structure

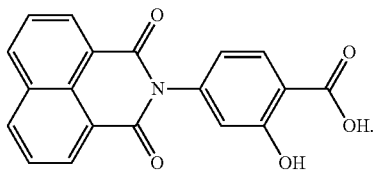 [SMILES: O=C(O)c1ccc(N2C(=O)c3cccc4cccc(c34)C2=O)cc1O]

In a 500 mL four-neck round bottom equipped with a temperature probe, heating mantle, agitator, and condenser, 17.95 g of naphthalic anhydride and 87 mL of acetic acid were charged. The mixture was heated to 70° C. and stirred until a clear solution was obtained. The solution was a light amber color. Then, 14.58 g of 4-aminosalicylic acid was added to the solution. After heating at reflux for 6 hours, the reaction mixture was poured into water. The product was collected by filtration and then washed with water. After drying, 22.18 g of product was obtained as a tan powder.

PREPARATION EXAMPLE EX40

This example demonstrates the production of the sodium salt of 4-(1,3-dioxo-1H,3H-benzo[de]isoquinolin-2-yl)-2-hydroxy-benzoic acid having the following structure

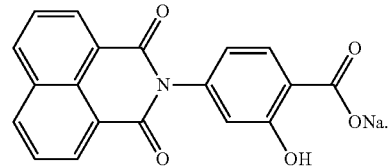

In a beaker, 4-(1,3-Dioxo-1H,3H-benzo[de]isoquinolin-2-yl)-2-hydroxy-benzoic acid was mixed with 200 mL of water.

Then a 50% solution of sodium hydroxide was slowly added until a stable pH value of 12 was obtained. The solution was concentrated in vaccuo to yield the sodium salt of 4-(1,3-dioxo-1H,3H-benzo[de]isoquinolin-2-yl)-2-hydroxy-benzoic acid.

PREPARATION EXAMPLE EX41

This example demonstrates the production of the potassium salt of 4-(1,3-Dioxo-1H,3H-benzo[de]isoquinolin-2-yl)-2-hydroxy-benzoic acid have the following structure

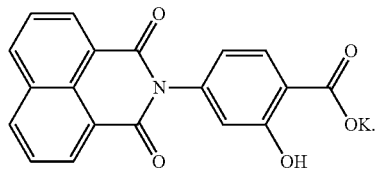

In a beaker, 4-(1,3-Dioxo-1H,3H-benzo[de]isoquinolin-2-yl)-2-hydroxy-benzoic acid was mixed with 200 mL of water. Then, potassium hydroxide was slowly added until a stable pH value of 12 was obtained. The solution was concentrated in vaccuo providing the potassium salt of 4-(1,3-dioxo-1H,3H-benzo[de]isoquinolin-2-yl)-2-hydroxy-benzoic acid.

PREPARATION EXAMPLE EX42

This example demonstrates the production of N-(3,4-dimethyl-phenyl)-terephthalamic acid having the following structure

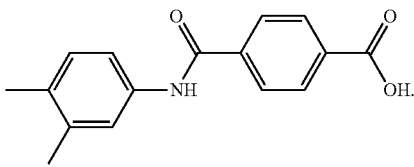 [SMILES: Cc1ccc(NC(=O)c2ccc(C(=O)O)cc2)cc1C]

The product was prepared in a similar manner to that used in PREPARATION EXAMPLE EX37 using the 3,4-dimethyl aniline in the place of cycloheptylamine.

PREPARATION EXAMPLE EX43

This example demonstrates the production of the potassium salt of N-(3,4-Dimethyl-phenyl)-terephthalamic acid having the following structure

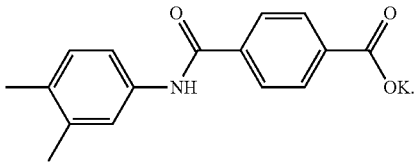

In a beaker, N-(3,4-Dimethyl-phenyl)-terephthalamic acid was mixed with 200 mL of water. Then, potassium hydroxide was slowly added until a stable pH of 12 and a clear solution was obtained. The solution was concentrated in vaccuo providing the desired product.

PREPARATION EXAMPLE EX44

This example demonstrates the production of the lithium salt of N-(3,4-Dimethyl-phenyl)-terephthalamic acid having the following structure

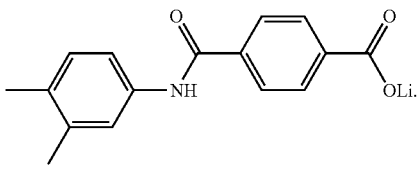

In a beaker, N-(3,4-Dimethyl-phenyl)-terephthalamic acid was mixed with 200 mL of water. Then, lithium hydroxide monohydrate was slowly added until a stable pH value of 12 was obtained. The solution was concentrated in vaccuo providing the desired product.

PREPARATION EXAMPLE EX45

This example demonstrates the production of 4-benzoylamino benzoic acid having the following structure

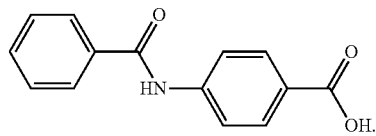 [SMILES: O=C(O)c1ccc(NC(=O)c2ccccc2)cc1]

In a 1 L beaker with mechanical stirring, 27.4 g of 4-aminobenzoic acid (0.2 mol) was mixed in 300 mL of DI $H_2O$. Then, 21.2 g (0.2 mol) of sodium carbonate was added until the pH value became 9.1 and all the 4-amino benzoic acid dissolved in the water.

Then, 56.24 g (0.4 mol) of benzoyl chloride was added dropwise to the beaker at room temp. The reaction was stirred overnight. A solid formed during the reaction, and the pH stabilized at 4.0. The pH was further lowered to about 2 with hydrochloric acid. The product was collected by filtration and washed with hot water to remove excess benzoic acid. The solid product was dried in an oven at 110° C. and 44.21 g of the product was obtained (yield 96.7%).

PREPARATION EXAMPLE EX46

This example demonstrates the production of the lithium salt of 4-benzoylamino benzoic acid having the following structure

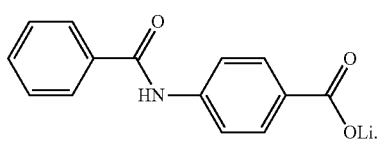

In a 500 mL beaker, 44.21 g of 4-benzoamido-benzoic acid was mixed with about 250 mL of water. Then, 7.69 g of lithium hydroxide monohydrate (dissolved in about 100 mL of water) was added. The reaction was stirred overnight and the pH value became neutral. The solid product was collected by filtration and dried in an oven at 110° C., 39.7 g of material was obtained (yield 88%).

PREPARATION EXAMPLE 47

This example demonstrates the production of the magnesium salt of 4-benzoylamino benzoic acid having the following structure

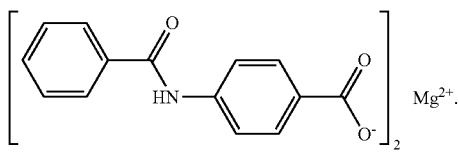

In a 500 mL beaker, 30 g of 4-benzoamido-benzoic acid was mixed with about 250 mL of water. Then, 6.98 g of potassium hydroxide (dissolved in about 50 mL of water) was added. The resulting mixture was stirred overnight. All of the solids dissolved, and the pH value became neutral. Then, 25.3 g of magnesium chloride hexahydrate in about 100 mL water was added. The product precipitated out immediately. The mixture was stirred one more hour after the addition and then filtered to collect the product. The product was washed with DI water and dried in an oven at 110° C.

PREPARATION EXAMPLE EX48

This example demonstrates the production of 4-N-cyclohexyl-amidobenzoic acid having the following structure

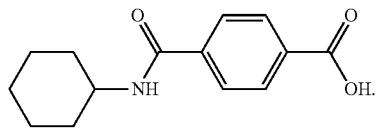 [SMILES: O=C(O)c1ccc(C(=O)NC2CCCCC2)cc1]

In a 2 L round bottom flask equipped with an ice bath, 3.83 g of sodium bicarbonate, 4.53 g of cyclohexylamine, 0.5 g of triethylamine, and 200 mL of tetrahydrofuran were added. Then, 9.06 g of 4-carbomethoxybenzoyl chloride (dissolved in 9.70 g of tetrahydrofuran) was added dropwise over an hour to the flask. After addition, the reaction was gently heated to reflux. IR was monitored for completion of the reaction (the disappearance of the peak at 1780 cm$^{-1}$). After completion, the reaction was diluted with 2 L of $H_2O$, stirred 20-30 min, and then filtered to collect the solid as the product. The product was dried in an oven at 110° C.; 11.31 g of product was obtained.

To a 2 L three-necked round bottom flask, 11.31 g of the product made in the previous step and 150 mL of methanol were added. Then, 2.72 g of potassium hydroxide (dissolved in methanol) was added dropwise to the flask. After completion of the addition, the reaction was heated to reflux. IR was monitored for completion of the reaction (the disappearance of the peak at 1720 cm$^{-1}$). After the reaction, 750 mL of water was added and filtered to remove any insoluble impurities. The pH of the filtrate was adjusted to about 2 with hydrochloric acid to precipitate the product. The mixture was filtered to collect the product, and the product was washed with DI water. The product was dried in an oven at 110° C.

PREPARATION EXAMPLE EX49

This example demonstrates the production of the potassium salt of 4-N-cyclohexyl-amidobenzoic acid having the following structure

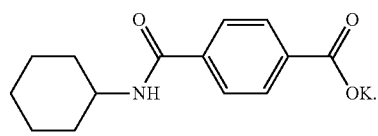

In a beaker, 6 g of 4-N-cyclohexyl-amidobenzoic acid was dispersed in 50 mL of $H_2O$. Then, 1.36 g of potassium hydroxide was dissolved in another beaker with about 20 mL of $H_2O$ and then added to the slurry. Most of material dissolved and the residual insoluble solid was removed by filtration. The $H_2O$ was stripped off from the filtrate to collect the product. The product was dried in an oven overnight at 110° C.

PREPARATION EXAMPLE EX50

This example demonstrates the production of the aluminum salt of 4-N-cyclohexyl-amidobenzoic acid having the following structure

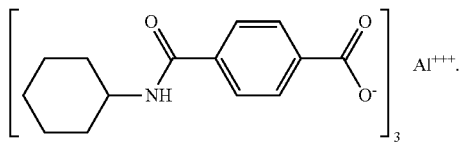

1 gram of the potassium salt of 4-N-cyclohexyl-amidobenzoic acid was dissolved in a beaker with about 25 mL of $H_2O$. In another beaker, 0.78 g of aluminum sulfate octadecahydrate was dissolved with about 15 mL of $H_2O$. The two solutions were mixed and a precipitate formed instantly. The solid was collected by suction filtration and dried in an oven overnight at 110° C.

PREPARATION EXAMPLE EX51

This example demonstrates the production of 4-(1,3-dioxo-1H,3H-benzo[de]isoquinolin-2-yl)-benzoic acid having the following structure

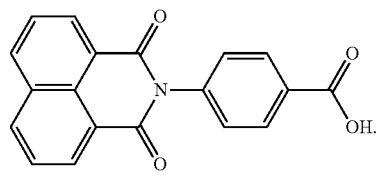 [SMILES: O=C(O)c1ccc(N2C(=O)c3cccc4cccc(c34)C2=O)cc1]

In a 1 L four-neck round bottom flask equipped with a temperature probe, heating mantle, agitator, and condenser, 25 g of naphthalic anhydride and 80 mL of acetic acid were charged. After the formation of a dark red-orange solution, 17.31 g of 4-aminobenzoic acid was added and the reaction was heated to reflux overnight. The reaction mixture was poured into excess amount of DI water to precipitate the product. The product was collected by filtration, washed with more DI water, and then dried in an oven.

PREPARATION EXAMPLE EX52

This example demonstrates the production of the lithium salt of 4-(1,3-dioxo-1H,3H-benzo[de]isoquinolin-2-yl)-benzoic acid having the following structure

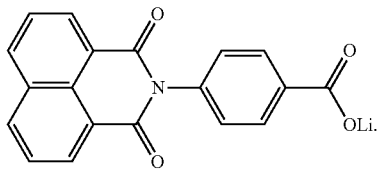

In a 1000 mL beaker equipped with an overhead agitator, 5.09 g of 4-(1,3-dioxo-1H,3H-benzo[de]isoquinolin-2-yl)-benzoic acid and 100 mL of DI H$_2$O was charged. The reaction was stirred, and the pH was adjusted with lithium hydroxide until all the acid was in solution. Water was removed by rotary evaporation. 5.231 g of the product was obtained.

PREPARATION EXAMPLE EX53

This example demonstrates the production of the lithium salt of N-benzyl-terephthalamic acid having the following structure

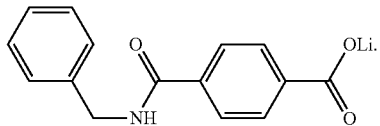

In a three-neck round bottom flask fitted with a condenser and addition funnel, 6.345 g of sodium bicarbonate, 8.09 g of benzylamine, 0.5 g of triethylamine and 350 mL of tetrahydrofuran were added. The mixture temperature was cooled to below 10° C. Then, 15 g of carbomethoxybenzoyl chloride (dissolved in about 150 mL of tetrahyfrofuran) was added dropwise over one hour. After addition, the mixture was gently heated to reflux. The reaction was monitored to completion with IR (disappearance of peak at 1780 cm$^{-1}$). Upon completion, the mixture was diluted with about 2 L of DI water and stirred for 20-30 min. The product was collected by filtration and dried in an oven at 100° C. 18.68 gram of material was obtained (yield 91.84%)

In a 2 L beaker, 2.12 g of the product from the previous step and 300 mL of DI water were added. Then, 1.89 g of a 10% solution of lithium hydroxide was added and stirred until the reaction was completed (disappearance of peak at 1720 cm$^{-1}$ in IR). Then, all the water was removed by rotary evaporation to collect the product; 1.94 g of the product was obtained (yield 94.37%).

PREPARATION EXAMPLE EX54

This example demonstrates the production of the lithium salt of N-pyridin-2-yl-terephthalamic acid having the following structure

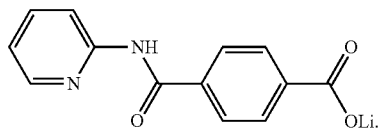

In a 250 mL three-neck round bottom flask equipped with overhead stirring, temperature probe, ice bath and reflux condenser, 4.71 g of 3-aminopyridine, 4.2 g of sodium bicarbonate, about 0.1 g of triethylamine, and 50 mL of tetrahydrofuran were added. The temperature was cooled to below 10° C. and then 9.9 gram of carbomethoxybenzoyl chloride (a solution in 20 mL of tetrahydrofuran) was added dropwise over 1-1.5 hours. The reaction was stirred overnight and then heated to reflux for about 2 hours. Then, 500 mL of DI water was used to dilute the reaction and the resulting mixture was stirred for 20-30 minutes. The solid product was collected by filtration and dried in an oven at 110° C.

In a 250 mL beaker equipped with a magnetic stir bar, 2.56 g of the product made in the previous step, 0.42 g of lithium hydroxide monohydrate, and 50 mL of DI water were added. The beaker was heated to 90° C. until the pH was below 10. The solid product was collected by filtration and any water was removed by evaporation.

PREPARATION EXAMPLE EX55

This example demonstrates the production of N-(2-chlorophenyl)-terephthalamic acid having the following structure

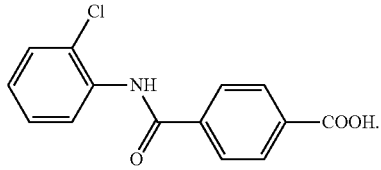 [SMILES: O=C(O)c1ccc(C(=O)Nc2ccccc2Cl)cc1]

In a 2 L round bottom flask, 6.34 g of sodium bicarbonate, 9.63 g of 2-chloroaniline, 0.5 g of triethylamine, and 200 mL of tetrahydrofuran were added. After the reaction was cooled with an ice bath, 15 g of carbomethoxybenzoyl chloride (dissolved in about 100 mL of THF) was added dropwise to the flask. After addition, the reaction was heated to reflux. IR was monitored for completion (the disappearance of the peak at 1780 cm$^{-1}$). After completion, the solution was diluted with 2 L of DI H$_2$O and stirred 20-30 min. The solid product was collected by filtration and dried in an oven at 110° C.

To a 2 L three-necked round bottom flask, 20.12 g of the product from the previous step and 150 mL of methanol were added. The reaction was heated to reflux. Upon starting heating, 3.90 g of potassium (dissolved in methanol) was added dropwise to the reaction. IR was monitored for completion (the disappearance of the peak at 1720 cm$^{-1}$). After completion, the solution was diluted with excess H$_2$O. Filtration was used to remove any residual solid, and then HCl was added to the filtrate until the pH value was about 2. The product precipitated out at this step, was collected by filtration, and then dried in an oven at 110° C.

PREPARATION EXAMPLE EX56

This example demonstrates the production of the lithium salt of N-(2-chloro-phenyl)-terephthalamic acid having the following structure

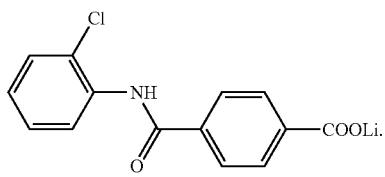

In a beaker, 1 gram of N-(2-Chloro-phenyl)-terephthalamic acid was suspended in about 20 mL water and then 0.1527 g of lithium hydroxide monohydrate was added. The reaction was stirred until the pH decreased to below 10. The solid product was collected by filtration.

PREPARATION EXAMPLE EX57

This example demonstrates the production of the potassium salt of N-(2-chloro-phenyl)-terephthalamic acid having the following structure

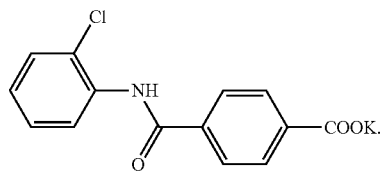

In a beaker, 12 gram of N-(2-Chloro-phenyl)-terephthalamic acid was suspended in about 200 mL of water and then 2.448 g of potassium hydroxide was added. The reaction was stirred until the pH decreased to below 10. The product was collected after rotary evaporation to remove excess water.

PREPARATION EXAMPLE EX58

This example demonstrates the production of N-(3,5-dicyano-4-methyl-thiophen-2-yl)-terephthalamic acid having the following structure

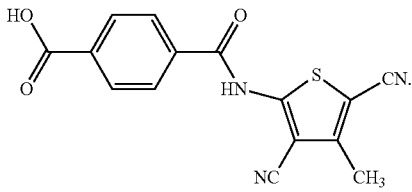 [SMILES: Cc1c(C#N)sc(NC(=O)c2ccc(C(=O)O)cc2)c1C#N]

In a three-neck round bottom flask equipped with overhead stirring, temperature probe, dry ice bath and reflux condenser, 12.32 g of 5-amino-3-methylthiophene-2,4-dicarbonitrile, 6.27 g of soda ash, and 200 mL of tetrahydrofuran were added. The temperature was lowered to below 10° C. and then 30 gram of a carbomethoxybenzoyl chloride solution (50% solution in tetrahydrofuran) were added dropwise over 1-1.5 hours. After addition, the mixture was heated to about 40° C. until the reaction was complete (monitored by IR, the peak at 1780 cm$^{-1}$ disappeared). Then, the reaction was diluted with about 2 L of DI water and filtered to collect the product.

In a 32 oz jar equipped with a magnetic stir bar, 17.4 g of the product made in the previous step was dissolved in 300 mL methanol. And then 30.05 g of a potassium hydroxide solution (10% in methanol) was added. The reaction was monitored by IR. After the completion of the reaction, the mixture was diluted with 1 liter of water. The mixture was filtered to remove any insoluble impurities, and the filtrate was acidified with hydrochloric acid until the pH was about 2. The product precipitated out at this step. The mixture was filtered to collect the product. The product washed with DI water and dried.

PREPARATION EXAMPLE EX59

This example demonstrates the production of the sodium salt of N-(3,5-dicyano-4-methyl-thiophen-2-yl)-terephthalamic acid having the following structure

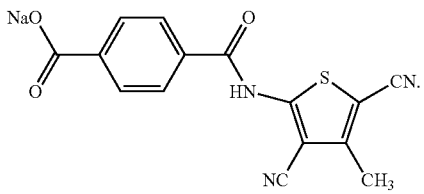

In a beaker, N-(3,5-Dicyano-4-methyl-thiophen-2-yl)-terephthalamic acid was mixed with 200 mL of water. Then, a 25% solution of sodium hydroxide was slowly added until a stable pH value of 12 was obtained. The solution was concentrated in vaccuo providing the desired product.

PREPARATION EXAMPLE EX60

This example demonstrates the production of the lithium salt of N-(3,5-dicyano-4-methyl-thiophen-2-yl)-terephthalamic acid having the following structure

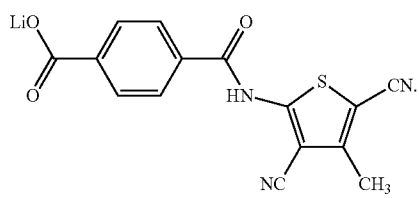

In a beaker, N-(3,5-Dicyano-4-methyl-thiophen-2-yl)-terephthalamic acid was mixed with 200 mL of water. Then, lithium hydroxide monohydrate was slowly added until a stable pH value of 12 was obtained. The solution was concentrated in vaccuo providing the desired product.

PREPARATION EXAMPLE EX61

This example demonstrates the production of the zinc salt of N-(3,5-dicyano-4-methyl-thiophen-2-yl)-terephthalamic acid having the following structure

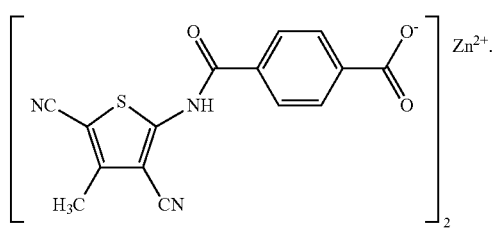

In a beaker, N-(3,5-Dicyano-4-methyl-thiophen-2-yl)-terephthalamic acid was mixed with 200 mL of water. Then, a 25% solution of potassium hydroxide was slowly added until a stable pH value of 12 was obtained. One equivalent of zinc chloride (dissolved in water) was then added to the solution and the product precipitated out. The product was collected by filtration and washed with DI water.

PREPARATION EXAMPLE EX62

This example demonstrates the production of the lithium salt of N-Pyridin-3-yl-terephthalamic acid having the following structure

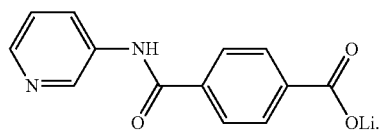

In a 250 mL three-neck flask equipped with overhead stirring, temperature probe, ice bath and reflux condenser, 4.71 g of 3-aminopyridine, 4.2 g of sodium bicarbonate, about 0.1 g of triethylamine, and 50 mL of tetrahydrofuran were added. The temperature was lowered to below 10° C., and then 9.9 gram of carbomethoxybenzoyl chloride (a solution in 20 mL tetrahydrofuran) was added dropwise over 1-1.5 hours. The reaction was stirred overnight and then was heated to reflux for about 2 hours. Then, the reaction was diluted with about 500 mL of DI water and stirred for 20-30 minutes. The solid product was collected by filtration and dried in an oven at 110° C.

In a 250 mL beaker equipped with a magnetic stir bar, 2.56 g of the product made in the previous step, 0.42 g of lithium hydroxide monohydrate, and 75 mL of DI water were added. The beaker was heated to 90° C. until the pH was below 10. Any solids were removed through filtration, and the filtrate was collected. The product was collected after excess water was removed through evaporation.

PREPARATION EXAMPLE EX63

This example demonstrates the production of N-(2-Methoxy-phenyl)-terephthalamic acid having the following structure

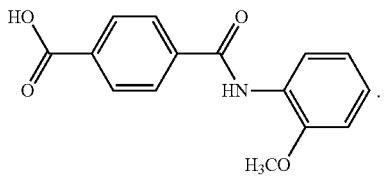

In a three-neck flask equipped with overhead stirring, temperature probe, dry ice bath and reflux condenser, 7.44 g of o-anisidine, 5.01 g of soda ash, and 200 mL of tetrahydrofuran were added. The temperature was lowered to below 10° C. and then 25 gram of a carbomethoxybenzoyl chloride solution (48% in tetrahydrofuran) was added dropwise over 1-1.5 hours. After addition, the reaction was heated to about 40° C. until the reaction was completed (monitored by IR, the peak at 1780 cm$^{-1}$ disappeared). Then, the mixture was diluted with about 2 L of DI water, and the product was collected by filtration.

In a 32 oz jar equipped with a magnetic stir bar, 13.95 g of the product made in previous step was dissolved in 300 mL methanol. Then, 27.5 g of potassium hydroxide solution (10% in methanol) was added. The reaction was monitored by IR. After the completion of the reaction, the mixture was diluted with about 1 L water. Insoluble impurities were removed by filtration. The filtrate was acidified with hydrochloric acid until the pH was about 2. The product precipitated out at this step. The product was collected by filtration, washed with DI water, and dried.

PREPARATION EXAMPLE EX64

This example demonstrates the production of the potassium salt of N-(2-methoxy-phenyl)-terephthalamic acid having the following structure

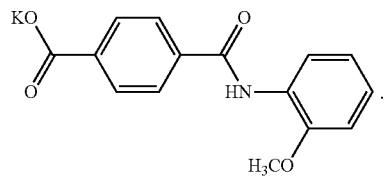

In a beaker, N-(2-methoxy-phenyl)-terephthalamic acid was mixed with 200 mL of water. Then, a 25% solution of potassium hydroxide was slowly added until a stable pH value of 12 was obtained. The solution was concentrated in vaccuo to yield the desired product.

PREPARATION EXAMPLE EX65

This example demonstrates the production of the magnesium salt of 4-N-phenyl-terephthalamic acid having the following structure

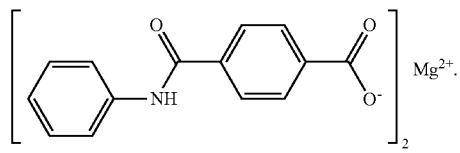

In a 250 mL beaker equipped with a magnetic stir bar and stir plate, 10 g of 4-N-phenylamidobenzoic acid and 50 mL of water were added. The reaction was heated to near boiling and 1.5 g magnesium oxide was added. IR was used to monitor the reaction to completion, and the product was collected by filtration.

PREPARATION EXAMPLE EX66

This example demonstrates the production of the lithium salt of 4-N-(3,4-dichlorophenyl)amidobenzoic acid having the following structure

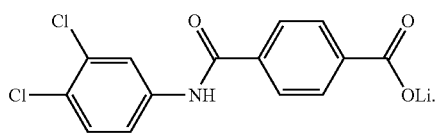

In a 1 L three-neck round bottom flask equipped with magnetic stirring, addition funnel, ice bath, nitrogen inlet and a hotplate, 12.48 g of 3,4-dichloroaniline, 6.34 g of sodium bicarbonate, 0.5 g of triethylamine, and 200 mL of tetrahydrofuran were added. The temperature was lowered to below 10° C. and then 15 gram of carbomethoxybenzoyl chloride (a solution in 100 mL tetrahydrofuran) was added dropwise over 1-1.5 hours. After addition, the reaction was heated to about 40° C. until the reaction was complete (monitored by IR, the peak at 1780 cm$^{-1}$ disappeared). Then, the reaction was diluted with about 2 L of DI water and the product was collected by filtration. 23.87 g of product was obtained (yield: 97.5%).

In a 250 mL beaker, 3 g of the product from the previous step was mixed with 50 mL water. The mixture was heated to near boiling, and 2.22 gram of a 10% solution of lithium hydroxide was added. The reaction was monitored to completion by IR. The reaction mixture was evaporated to near dryness and the product was collected by filtration. 1.92 g of the product was obtained (yield 65.6%).

PREPARATION EXAMPLE EX67

This example demonstrates the production of the calcium salt of 4-N-(2,6-diisopropylphenyl)amidobenzoic acid having the following structure

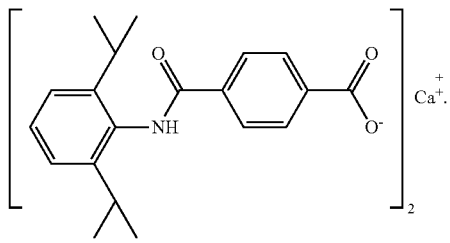

In a 1 L three-neck round bottom flask equipped with a magnetic stirrer, addition funnel, ice bath, nitrogen sweep, scrubber, and hot plate, 14.73 g of 2,6-diisopropylaniline, 6.34 g of sodium bicarbonate, 0.5 g of triethylamine, and 200 mL of tetrhydrofuran were charged. The mixture was cooled to below 10° C., and then 15 g of carbomethoxybenzoyl chloride (dissolved in 100 mL of tetrahydrofuran) was added dropwise over 1-1.5 hours. After addition, the reaction was slowly heated to reflux. After the reaction was complete (disappearance of peak at 1780 cm$^{-1}$ in IR), it was diluted with cold DI water and stirred for 20-30 minutes. The product was collected by filtration and dried in an oven at 110° C.

In a 600 mL beaker, 13.79 gram of the product from the previous step was mixed in 200 mL water. The mixture was heated to near boiling, and 22.8 gram of a 10% solution of potassium hydroxide was added. After the completion of the reaction was monitored by IR, 6.72 g of calcium chloride dihydrate (dissolved to form 10% solution) was added. The product precipitated out and was collected by filtration.

PREPARATION EXAMPLE EX68

This example demonstrates the production of 4-benzoylamino-2-hydroxy-benzoic acid having the following structure

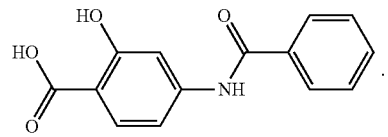

In a three-neck flask equipped with overhead stirring, temperature probe, dry ice bath, and a reflux condenser, 25 g of 4-aminosalicyclic acid, 5.01 g of soda ash, and 200 mL of tetrahydrofuran were added and stirred. The temperature was lowered to below 10° C., and 7.32 g benzoyl chloride was added dropwise over 1-1.5 hour. After addition, the flask was gently heated to 40° C. After the completion of the reaction (monitored by IR as the peak at 1780 cm$^{-1}$ disappears), the reaction mixture was diluted with 300 mL of water. The organic layer was separated. After drying off the solvent, about 16 grams of product was obtained.

PREPARATION EXAMPLE EX69

This example demonstrates the production of the lithium salt of 4-benzoylamino-2-hydroxy-benzoic acid having the following structure

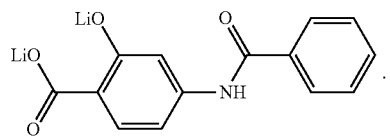

In a beaker, 3 grams of 4-Benzoylamino-2-hydroxy-benzoic acid was mixed with 20 mL of water. Then, 1.05 g of lithium hydroxide monohydrate was added. The mixture was stirred for 20 minutes, and then the reaction mixture was concentrated in vaccuo to provide the desired lithium salt.

PREPARATION EXAMPLE EX70

This example demonstrates the production of the calcium salt of 4-benzoylamino-2-hydroxy-benzoic acid having the following structure

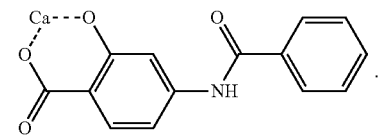

In a beaker, 3 grams of 4-Benzoylamino-2-hydroxy-benzoic acid was mixed with 20 mL of water. Then, 2.51 g of a 50% sodium hydroxide solution was added. After the solution became clear, a solution containing 3.53 g of calcium chloride dehydrate was added. The product precipitated out and was collected by filtration.

PREPARATION EXAMPLE EX71

This example demonstrates the production of 4-[(biphenyl-4-carbonyl)-amino]-benzoic acid having the following structure

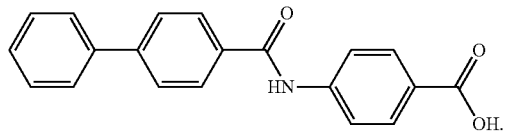 [SMILES: O=C(O)c1ccc(NC(=O)c2ccc(-c3ccccc3)cc2)cc1]

In a 5 L three-neck round bottom flask, 316.5 g of 4-aminobenzoic acid was dissolved in about 3 L of dioxane. Then, 250 grams of biphenyl-4-carbonyl chloride (dissolved in about 150 mL of dioxane) was added dropwise over 1 hour. The reaction was stirred overnight and filtered to collect the solid. The solid was washed with boiling DI water and then cold DI water until the pH of the water was about neutral. The washed solid was then dried in a vacuum oven.

PREPARATION EXAMPLE EX72

This example demonstrates the production of the lithium salt of 4-[(biphenyl-4-carbonyl)-amino]-benzoic acid having the following structure

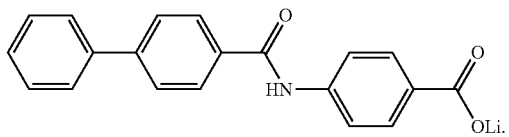

In a beaker, 364.62 g of 4-[(biphenyl-4-carbonyl)-amino]-benzoic acid was suspended in about 3 L of water. Then, a solution of lithium hydroxide monohydrate (41.96 g in about 500 mL water) was added to the suspension. The reaction was stirred overnight, and the pH value became 7.5. The solid product was collected by filtration, washed with water, and dried in an oven at 110° C. 334.7 g of the product was obtained (90% yield).

PREPARATION EXAMPLE EX73

This example demonstrates the production of 4-(benzylidene-amino)-benzoic acid having the following structure

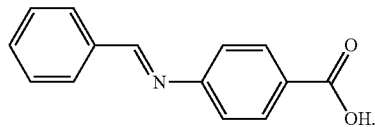 [SMILES: O=C(O)c1ccc(/N=C/c2ccccc2)cc1]

In a 500 mL three-neck round bottom flask equipped with a condenser, hearing mantle, magnetic stir and two stoppers, 10 gram of 4-aminobenoic acid, 7.75 g of benzaldehyde, and 200 mL of ethanol were added. The reaction mixture was heated to reflux for 6 hours. The product crystalized out of solution after the solution was cooled to room temperature.

The product was collected by filtration. Additional product was recovered by concentrating the filtrate. 15.41 g of the product was obtained (yield: 94%).

PREPARATION EXAMPLE EX74

This example demonstrates the production of the lithium salt of 4-(benzylidene-amino)-benzoic acid having the following structure

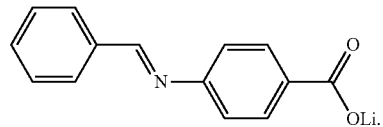

In a 2 L beaker, 15.41 of 4-(benzylidene-amino)-benzoic acid was dissolved in 200 mL of water. The mixture was gently heated and stirred on a hot plate until a clear solution was obtained. Then, 2.85 g of lithium hydroxide monohydrate was slowly added. The solution became slight hazy. After the completion of the reaction, it was cooled down and the water was evaporated off. A yellow solid was collected. The product was washed with acetone and then dried in an oven at 110° C.

PREPARATION EXAMPLE EX75

This example demonstrates the production of 4-chlorophenylamido-benzoic acid having the following structure

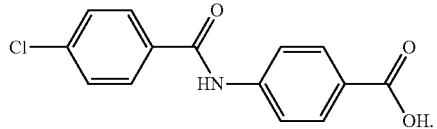 [SMILES: O=C(O)c1ccc(NC(=O)c2ccc(Cl)cc2)cc1]

In a 5 L flask, 274.3 g of 4-aminobenzoic acid (2 mol) and 2800 mL of acetone were added. The reaction was stirred until a uniform slurry formed. Then, 175 g of 4-chorobenzoyl chloride was added dropwise to the 5 L flask while the contents were being stirred. The reaction was stirred overnight and then filtered to collect the solid. The product was rinsed with about 500 mL of acetone and then three times with water (500 mL each time). After washing, the solid was moved to a 4 L beaker and suspended in about 2 L of boiling water for an hour. The solid product was collected by filtration and washed with more boiling water until the water was colorless.

PREPARATION EXAMPLE EX76

This example demonstrates the production of the sodium salt of 4-chlorophenylamido-benzoic acid having the following structure

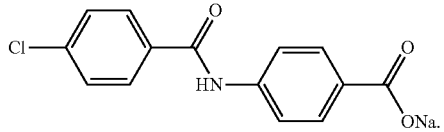

In a 2 L beaker equipped with a mechanical stirrer, 400 mL of water and 27.5 g of 4-chlorophenylamido-benzoic acid were added. In another beaker, 8.4 grams of NaOH (50% solution) was diluted in 100 mL of water. The NaOH solution was added to the 4-chlorophenylamido-benzoic acid suspension, and the mixture was stirred overnight. The product was collected by filtration. The product was washed with DI water until the pH of the water was below 10, and the product was then dried in an oven at 110° C.

PREPARATION EXAMPLE EX77

This example demonstrates the production of 4-(4-fluoro-benzoylamino)-benzoic acid having the following structure

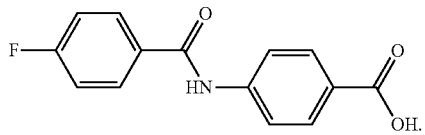

In a 4 L beaker, 21.27 g of 4-aminobenzoic acid and 1 L of DI H₂O were added. Then, 33.38 g of sodium carbonate was added. Next, 100 g of 4-fluorobenzoyl chloride was added dropwise to flask (over about 45 min-1 h) and the reaction was stirred overnight. The solid product was collected by vacuum filtration and washed with boiling water to remove excess 4-fluorobenzoic acid. The product was dried overnight in a vacuum oven. 59.08 g of product was obtained.

PREPARATION EXAMPLE EX78

This example demonstrates the production of the lithium salt of 4-(4-fluoro-benzoylamino)-benzoic acid having the following structure

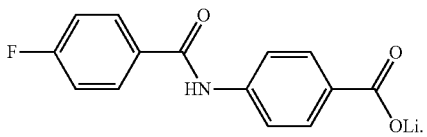

In a beaker, 10 gram of 4-(4-fluoro-benzoylamino)benzoic acid was suspended in 100 mL of DI water. Then, 1.62 g of lithium hydroxide monohydrate was first dissolved in 25 mL of DI water and then added into the acid suspension. The reaction was stirred overnight and the product was collected by evaporating off the water.

PREPARATION EXAMPLE EX79

This example demonstrates the production of 4-benzoylamino-2,3,4,5-tetrafluoro-benzoic acid having the following structure

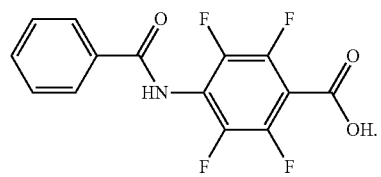 [SMILES: O=C(Nc1c(F)c(F)c(C(=O)O)c(F)c1F)c1ccccc1]

In a 250 mL flask equipped with a stirrer, 3.37 g of 4-amino-2,3,4,5-tetrafluoro benzoic acid, 1.06 g of sodium carbonate, and 20 mL of water were added. Then, 6.8 g of 4-benzoyl chloride was added dropwise to the flask (over about 45 min-1 h). The pH was recorded below 1 the next morning. The solid product was collected by filtration, washed with DI water 5 times, and then dried in an oven at 110° C.

PREPARATION EXAMPLE EX80

This example demonstrates the production of the lithium salt of 4-(4-fluoro-benzoylamino)-benzoic acid having the following structure

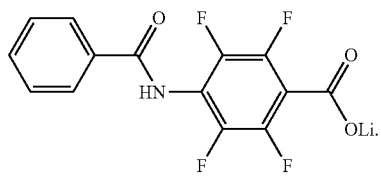

In a 250 mL beaker, 2 gram of 4-Benzoylamino-2,3,4,5-tetrafluoro-benzoic acid and 20 mL of DI water were added. Then, 0.27 g of lithium hydroxide monohydrate was first dissolved in 10 mL of DI water and then added into the acid suspension. The reaction was stirred overnight, and the product was collected by evaporating off the water.

PREPARATION EXAMPLE EX81

This example demonstrates the production of benzene-1,3,5-tricarboxylic acid tris-(4-carboxybenzene)amide having the following structure

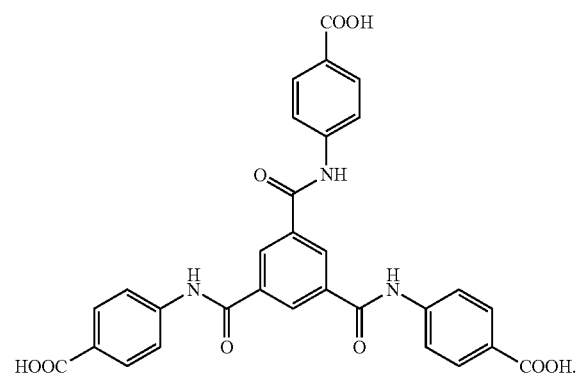 [SMILES: O=C(O)c1ccc(NC(=O)c2cc(C(=O)Nc3ccc(C(=O)O)cc3)cc(C(=O)Nc3ccc(C(=O)O)cc3)c2)cc1]

In a three neck round bottom flask, 21.2 g of sodium carbonate and 100 mL of tetrahydrofuran were added. Then, 13.75 g of 4-aminobenzoic acid and 8 g of 1,3,5-benzenetricarbonyl trichloride were each separately diluted in 15 mL of THF and added into the reaction simultaneously via two addition funnels. The reaction was stirred overnight at room temperature. About 80 mL of tetrahydrofuran was added to compensate the evaporation during the reactions and an additional 10.6 gram of sodium carbonate was added. Three hours later, the reaction was transferred to a 1 L beaker with 600 mL of water. The pH was adjusted to about 2 with hydrochloric acid. The product precipitated out and was collected by filtration. The product was then partially dried in a vacuum oven at 40° C. About 35 gram of wet product was obtained.

PREPARATION EXAMPLE EX82

This example demonstrates the production of the sodium salt of benzene-1,3,5-tricarboxylic acid tris-(4-carboxybenzene)amide having the following structure

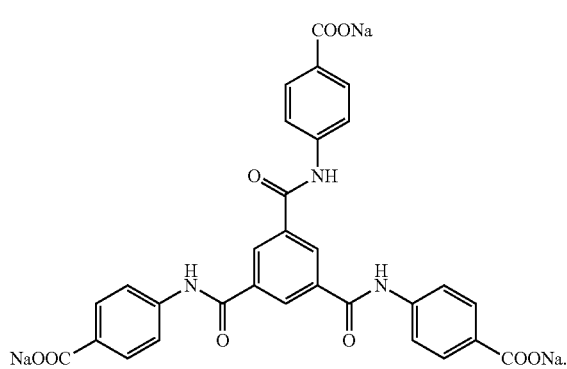

In a beaker, 32 grams of benzene-1,3,5-tricarboxylic acid tris-(4-carboxybenezene)amide was mixed with 200 mL of water. Then, a 50% sodium hydroxide solution was slowly added to the mixture until the pH was 12. The mixture was stirred for 20 minutes and then was concentrated in vaccuo to yield the product.

PREPARATION EXAMPLE EX83

This example demonstrates the production of biphenyl-4,4'-dicarboxylic acid bis-(4-carboxybenezene)amide having the following structure

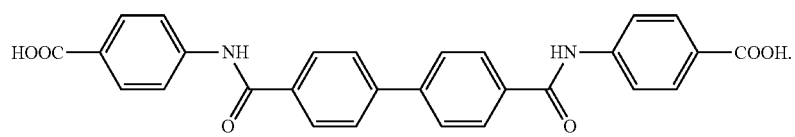

In a three neck round bottom flask, 5.67 g of sodium carbonate and about 40 mL of tetrahydrofuran were added. Then, 4.9 g of 4-aminobenzoic acid and 5.0 g of 4,4'-Biphenyldicarbonyl chloride were each separately diluted in 15 mL of THF and then added to the reaction simultaneously via two addition funnels. The reaction was stirred overnight at room temperature. Then, the reaction was transferred to a 1 L beaker with 600 mL of water. The pH was adjusted to about 2 with hydrochloric acid. The product precipitated out and was collected by filtration. The product was dried in vacuum oven at 50° C.

PREPARATION EXAMPLE EX84

This example demonstrates the production of the sodium salt of biphenyl-4,4'-dicarboxylic acid bis-(4-carboxybenezene)amide having the following structure

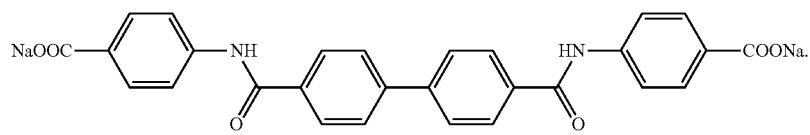

In a beaker, 12 grams of acid (biphenyl-4,4'-dicarboxylic acid bis-(4-carboxybenezene)amide was mixed with 100 mL of water. Then, a 50% sodium hydroxide solution was slowly added to the mixture until the pH was 12.5. The mixture was stirred for 20 minutes and then was concentrated in vaccuo to yield the product.

PREPARATION EXAMPLE EX85

This example demonstrates the production of 4-(4-methyl-benzoylamino)benzoic acid having the following structure

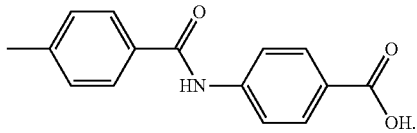 [SMILES: Cc1ccc(C(=O)Nc2ccc(C(=O)O)cc2)cc1]

In a 5 L three neck round bottom flask, 274 g of 4-aminobenzoic acid and 3000 mL of acetone were added. The mixture was stirred to form a clear solution. Then, 154.5 g of 4-methylbenzoyl chloride was added dropwise to the reaction. After addition, the reaction stirred overnight and then was filtered to collect the solid. The solid was washed with boiling water and then cold DI water until the pH of the water was neutral. The product was dried at 110° C.

PREPARATION EXAMPLE EX86

This example demonstrates the production of the lithium salt of 4-(4-methyl-benzoylamino)benzoic acid having the following structure

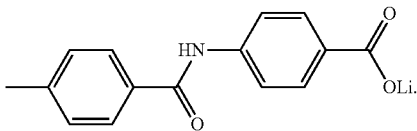

In a beaker, 25.5 g of 4-(4-methyl-benzoylamino)benzoic acid and 200 mL of DI water were added. The mixture was stirred until it formed a uniform slurry. Then, 4.2 g of lithium hydroxide monohydrate was added. The reaction was stirred overnight, and the pH value dropped to 10. The solid product was filtered and then dried in an oven at 110° C.

PREPARATION EXAMPLE EX87

This example demonstrates the production of the lithium salt of N-cyclopentyl-terephthalamic acid having the following structure

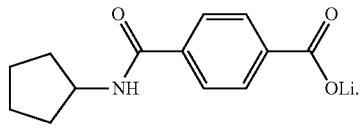

In a beaker, 23.3 g of N-cyclopentyl-terephthalamic acid was added to 100 mL of $H_2O$. Then, 4.2 g of lithium hydroxide monohydrate was dissolved in a separate beaker with about 50 mL of $H_2O$. The lithium hydroxide solution was added to the N-cyclopentyl-terephthalamic acid slurry and stirred until the pH value was about neutral. The product was partially soluble in water. The water was removed by evaporation to yield the product. The product was dried overnight in an oven at 110° C.

PREPARATION EXAMPLE EX88

This example demonstrates the production of the lithium salt of 4-(cyclopentanecarbonyl-amino)-benzoic acid having the following structure

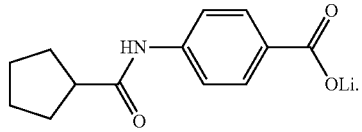

In a 1 liter 2-neck roundbottom flask, 40 grams of 4-aminobenzoic acid was dissolved in about 400 mL of dioxane. Then, 19.35 g of cyclopentanecarbonyl chloride was added dropwise to the solution. The reaction intermediate, 4-(cyclopentanecarbonyl-amino)-benzoic acid, formed as a white solid in the step and was collected by filtration. After washing the product with about 200 mL dioxane and then with about 1 liter of boiling water, the reaction intermediate was dried in an oven at 110° C. The yield at this step was about 27.7 g (81%).

The 27.7 gram of 4-(cyclopentanecarbonyl-amino)-benzoic acid was suspended in about 277 mL of water. Then, 5 grams of lithium hydroxide monohydrate was added. The mixture was stirred overnight, and the pH became about 7. After evaporating off the excess water, the final product (the lithium salt of 4-(cyclopentanecarbonyl-amino)-benzoic acid) was collected as a white solid and dried in an oven at 110° C.

EXAMPLE T1

Various additives from the Preparation Examples above were individually pulverized and mixed with a high density polyethylene polymer having a density of approximately 0.952 $g/cm^3$ and a melt flow index of approximately 19 dg/minute (ExxonMobil™ HDPE HD 6719). Then the mixture was either inject molded into bars or cast into thin films. The peak polymer recrystallization temperature ($T_c$) for each thermoplastic polymer composition was measured using a differential scanning calorimeter (Mettler-Toledo DSC822 differential scanning calorimeter). In particular, a sample was taken from the target part and heated at a rate of 20° C./minute from a temperature of 60° C. to 220° C., held at 220° C. for two minutes, and cooled at a rate of approximately 10° C./minute to a temperature of 60° C. The temperature at which peak polymer crystal reformation occurred (which corresponds to the peak polymer recrystallization temperature) was recorded for each sample and is reported in Table 1 below.

Comparative example CTCEX1 is the high density polyethylene polymer having a density of approximately 0.952 $g/cm^3$ and a melt flow index of approximately 19 dg/minute (ExxonMobil™ HDPE HD 6719), which was injection molded into sample bars. Comparative example CTCEX2 and CTCEX3 are the same high density polyethylene polymer containing 1000 ppm of sodium benzoate and aluminum bis[4-1(1,1-dimethylethy)benzoate]hydroxide (Al-pTBBA), respectively. Comparative example CTCEX4 is the same high density polyethylene polymer cast into a film. The examples TCEX1 to example TCEX56 are the high density polyethylene polymer cast film containing 1500 ppm of the Preparation Examples as disclosed in this application.

TABLE 1

Peak polymer recrystallization temperature (Tc) of various additives in PE.

| Example # | Additive | $T_c$ improvement (° C.) |
|---|---|---|
| CTCEX1 | None | 0.0 |
| CTCEX2 | sodium benzoate | −0.7 |
| CTCEX3 | Al-pTBBA | 0.0 |
| CTCEX4 | None | 0.0 |
| TCEX1 | EX3 | 2.0 |
| TCEX2 | EX5 | 3.0 |
| TCEX3 | EX7 | 1.8 |
| TCEX4 | EX8 | 2.5 |
| TCEX5 | EX9 | 2.2 |
| TCEX6 | EX11 | 2.8 |
| TCEX7 | EX12 | 1.7 |
| TCEX8 | EX13 | 2.7 |
| TCEX9 | EX15 | 1.7 |
| TCEX10 | EX17 | 1.8 |
| TCEX11 | EX18 | 1.5 |
| TCEX12 | EX20 | 1.2 |
| TCEX13 | EX21 | 2 |
| TCEX14 | EX22 | 2 |
| TCEX15 | EX24 | 1.2 |
| TCEX16 | EX26 | 1.7 |
| TCEX17 | EX27 | 1.5 |
| TCEX18 | EX29 | 2.7 |
| TCEX19 | EX31 | 2.5 |
| TCEX20 | EX32 | 1.5 |
| TCEX21 | EX33 | 1.8 |
| TCEX22 | EX35 | 1.5 |
| TCEX23 | EX36 | 2.7 |
| TCEX24 | EX38 | 2.3 |
| TCEX25 | EX40 | 2.0 |
| TCEX26 | EX41 | 1.7 |
| TCEX27 | EX43 | 1.8 |
| TCEX28 | EX44 | 1.0 |
| TCEX29 | EX46 | 1.8 |
| TCEX30 | EX47 | 1.7 |
| TCEX31 | EX50 | 1.7 |
| TCEX32 | EX52 | 1.5 |
| TCEX33 | EX53 | 1.5 |
| TCEX34 | EX54 | 1.0 |
| TCEX35 | EX56 | 1.3 |
| TCEX36 | EX57 | 1.5 |
| TCEX37 | EX59 | 1.5 |
| TCEX38 | EX60 | 1.3 |
| TCEX39 | EX61 | 1.2 |
| TCEX40 | EX62 | 1.7 |

TABLE 1-continued

Peak polymer recrystallization temperature (Tc) of various additives in PE.

| Example # | Additive | $T_c$ improvement (° C.) |
|---|---|---|
| TCEX41 | EX64 | 1.2 |
| TCEX42 | EX65 | 0.8 |
| TCEX43 | EX66 | 1.0 |
| TCEX44 | EX67 | 0.8 |
| TCEX45 | EX69 | 0.8 |
| TCEX46 | EX70 | 0.8 |
| TCEX47 | EX72 | 2.5 |
| TCEX48 | EX74 | 1.8 |
| TCEX49 | EX76 | 2.5 |
| TCEX50 | EX78 | 2.3 |
| TCEX51 | EX79 | 1.2 |
| TCEX52 | EX82 | 1.7 |
| TCEX53 | EX84 | 2.0 |
| TCEX54 | EX86 | 2.2 |
| TCEX55 | EX87 | 3.3 |
| TCEX56 | EX88 | 2.5 |

From Table 1, it is clear that all the metal salt compounds of the invention can increase the recrystallization temperature ($T_c$) of polyethylene to some degree. While $T_c$ is not the only important factor when choosing a suitable nucleator for a semi-crystalline thermoplastic polymer, the improvement in $T_c$ is very desirable as it improves crystallization rate during processing, shortens cycle time, and improves production efficiency.

Manufacture of Nucleated Blown Films

For all the blown film examples, the polyethylene resins used were first ground to about a 35 mesh powder. Then, 1000 ppm of Irganox 1010, 800 ppm of Irgafos 168, 1000 ppm of DHT4-A, and the inventive nucleating agent were added to the resin and blended in a Henschel high intensity mixer for about 2 minutes with a blade speed of about 2100 rpm. The samples were then melt compounded in a MPM single screw extruder with a 38 mm diameter screw. The barrel temperature of the extruder was ramped from 160 to 190° C. The extrudate in the form of strands, was cooled in a water bath and then subsequently pelletized.

Films were produced in a pilot scale blown film line, with a 4 in monolayer die, using a 2 mm die gap. The line included a Future Design dual lip air ring with chilled air. The extruder had a 55 mm diameter barrier screw, with a length to width ratio of 24:1. The barrel temperature of the extruder was ramped up from 190 to 220° C.

Testing of Nucleated Polyethylene Blown Films

The % haze of the parts was measured using a BYK Gardner Haze meter, according to ASTM D1023. The clarity of the parts was measured using a BYK Gardner Haze meter. Permeation, measured as Water Vapor Transmission Rate, was measured using an Illinois Instruments 7000 Water Vapor Permeation Analyzer, according to ASTM E398. Tear strength was measured using a ProTear tear tester according to ASTM D1922. Dart drop impact testing was performed using a Dynisco Model D2085AB-P dart drop polymer tester, according to ASTM D1709. Film tensile test was performed using a MTS Q-Test-5 instrument, according to ASTM D882.

The peak polymer recrystallization temperature ($T_c$) for the thermoplastic polymer compositions was measured using a differential scanning calorimeter (Mettler-Toledo DSC822 differential scanning calorimeter). In particular, a compression molded plaque was prepared from the pellets, and a sample was taken from the plaque and heated at a rate of 20° C./minute from a temperature of 60° C. to 220° C., held at 220° C. for two minutes, and cooled at a rate of approximately 10° C./minute to a temperature of 60° C. The temperature at which peak polymer crystal reformation occurred (which corresponds to the peak polymer recrystallization temperature) was recorded for each sample.

EXAMPLE F1

This example demonstrates some of the physical properties exhibited by a high density polyethylene polymer that has been nucleated with a nucleating agent according to the invention. Polymer compositions were prepared by compounding (as described above) 2000 ppm of EX5 into a commercially-available, high density polyethylene polymer (Sclair® 19G from Nova Chemicals) having a density of approximately 0.962 g/cm$^3$ and a melt flow index of approximately 1.2 dg/minute. The formed polymer composition pellet was then used to produce blown films (3 mil thickness) using the following setup: 101.6 mm (4 in) die, 2.0 mm die gap, BUR 2.3, DDR 11.4, and output 30 kg/h. The peak polymer recrystallization temperature, permeation, tear strength, dart drop impact, 1% secant modulus, and optical properties of the resulting films were measured and are reported in Tables F1 to F4.

EXAMPLE F2

Example F2 was prepared the same way as example F1 except EX46 was used in the place of EX5.

EXAMPLE F3

Example F3 was prepared the same way as example F1 except EX76 was used in the place of EX5.

COMPARATIVE EXAMPLE CF1

Comparative example CF1 was prepared the same way as example F1 except no nucleating agent was used.

TABLE F1

Peak polymer recrystallization temperature ($T_c$), vapor permeation, and dart drop impact of comparative example CF1 and examples F1, F2, and F3.

| Sample | Additive | loading (ppm) | $T_c$ (° C.) | Permeation (g · mil/m$^2$ · day) | Impact (g) |
|---|---|---|---|---|---|
| CF1 | None | | 115.2 | 3.9 | 95 |
| F1 | EX5 | 2000 | 120.2 | 5.8 | 119 |
| F2 | EX46 | 2000 | 119.2 | 5.0 | 133 |
| F3 | EX76 | 2000 | 118.8 | 1.7 | 94 |

TABLE F2

Haze and clarity of comparative example CF1 and examples F1, F2, and F3.

| Sample | Additive | loading (ppm) | Haze (%) | Standard deviation (%) | Clarity | Standard deviation |
|---|---|---|---|---|---|---|
| CF1 | None | | 49.9 | 2.1 | 93.4 | 0.7 |
| F1 | EX5 | 2000 | 42.3 | 1.2 | 96.3 | 0.3 |

TABLE F2-continued

Haze and clarity of comparative example CF1 and examples F1, F2, and F3.

| Sample | Additive | loading (ppm) | Haze (%) | Standard deviation (%) | Clarity | Standard deviation |
|---|---|---|---|---|---|---|
| F2 | EX46 | 2000 | 43.0 | 0.4 | 96.5 | 0.2 |
| F3 | EX76 | 2000 | 36.0 | 0.7 | 96.2 | 0.1 |

TABLE F3

1% secant modulus of comparative example CF1 and examples F1, F2, and F3.

| | | | Machine Direction | | Transverse Direction | |
|---|---|---|---|---|---|---|
| Sample | Additive | Loading (ppm) | 1% secant modulus (MPa) | Standard deviation (MPa) | 1% secant modulus (MPa) | Standard deviation (MPa) |
| CF1 | None | | 583 | 19 | 704 | 42 |
| F1 | EX5 | 2000 | 639 | 31 | 607 | 69 |
| F2 | EX46 | 2000 | 513 | 29 | 514 | 8 |
| F3 | EX76 | 2000 | 684 | 58 | 616 | 48 |

TABLE F4

Tear strength of comparative example CF1 and examples F1, F2, and F3.

| | | | Machine Direction | | Transverse Direction | |
|---|---|---|---|---|---|---|
| Sample | Additive | loading (ppm) | Tear Strength (g) | Standard deviation (g) | Tear Strength (g) | Standard deviation (g) |
| CF1 | None | | 60 | 3 | 168 | 4 |
| F1 | EX5 | 2000 | 88 | 3 | 134 | 3 |
| F2 | EX46 | 2000 | 86 | 4 | 147 | 6 |
| F3 | EX76 | 2000 | 78 | 5 | 85 | 2 |

From the data in Tables F1-F4, it is clear that all the additives, EX5, EX46, and EX76 increased the peak polymer recrystallization temperature, lowered the haze, and increased the clarity. In addition, EX5 and EX46 increased the machine direction tear strength, dart drop impact, and vapor permeation. EX76 also increased the machine tear resistance. More importantly, EX76 generated balanced tear strength in the machine and transverse directions, improved barrier property (evidenced by the lower permeation number), and improved machine direction stiffness (1% secant modulus).

EXAMPLE F4

This example demonstrates some of the physical properties exhibited by a linear low density polyethylene polymer that has been nucleated with a nucleating agent according to the invention. Polymer compositions were prepared compounding (as described above) 2000 ppm of EX5 into a commercially-available, butene linear low density polyethylene polymer (ExxonMobil™ LLDPE LL 1001.32) having a density of approximately 0.918 g/cm³ and a melt flow index of approximately 1.0 dg/minute. The formed polymer composition pellet was then used to produce blown films (2 mil thickness) using the following setup: 101.6 mm (4 in) die, 2.0 mm die gap, BUR 2.35, DDR 17, and output 30 kg/h. The peak polymer recrystallization temperature, permeation, dart drop impact, 1% secant modulus, and tear strength were measured and are reported in Tables F5 and F6.

EXAMPLE F5

Example F5 was prepared the same way as example F4 except EX46 was used in the place of EX5.

EXAMPLE F6

Example F6 was prepared the same way as example F4 except EX76 was used in the place of EX5.

COMPARATIVE EXAMPLE CF2

COMPARATIVE EXAMPLE CF2 was prepared the same way as example F4 except no nucleating agent was used.

TABLE F5

Peak polymer recrystallization temperature ($T_c$), vapor permeation, and dart drop impact of comparative example CF2 and samples F4, F5, and F6.

| Sample | Additive | loading (ppm) | $T_c$ (° C.) | Permeation (g · mil/m² · day) | Impact (g) |
|---|---|---|---|---|---|
| CF2 | None | | 105.5 | 17.21 | 203 |
| F4 | EX5 | 2000 | 112.0 | 17.53 | 206 |
| F5 | EX46 | 2000 | 111.0 | 15.94 | 215 |
| F6 | EX76 | 2000 | 111.5 | 10.66 | 208 |

TABLE F6

1% Secant modulus and tear strength of comparative sample CF2 and samples F4, F5, and F6.

| | Machine Direction | | Transverse Direction | | Machine Direction | | Transverse Direction | |
|---|---|---|---|---|---|---|---|---|
| Sample | 1% Secant (MPa) | Std Dev (MPa) | 1% Secant (MPa) | Std Dev (MPa) | Tear Strength (g) | Std Dev (g) | Tear Strength (g) | Std Dev (g) |
| CF2 | 169 | 5 | 197 | 6 | 388 | 22 | 578 | 16 |
| F4 | 174 | 6 | 174 | 8 | 436 | 35 | 579 | 33 |
| F5 | 170 | 7 | 180 | 6 | 431 | 21 | 575 | 23 |
| F6 | 196 | 8 | 214 | 12 | 399 | 53 | 569 | 48 |

From the data in Tables F5 and F6, it is clear that the additives, EX5, EX46, and EX76 increased the peak polymer recrystallization temperature. EX5 and EX46 increased the machine direction tear strength and EX76 significantly increased the machine direction modulus. All three nucleating agents of the invention increase the dart impact resistance slightly.

EXAMPLE F7

This example demonstrates some of the physical properties exhibited by a linear low density polyethylene polymer that has been nucleated with a nucleating agent according to the invention. Polymer compositions were prepared by compounding (as described above) 2000 ppm of EX46 into a commercially-available, linear low density polyethylene polymer (Dowlex™ 2056G) having a density of approximately 0.922 g/cm³ and a melt flow index of approximately 1.0 dg/minute. The formed polymer composition pellet was then used to produce blown films (1 mil thickness) using the following setup: 101.6 mm (4 in) die, 2.0 mm die gap, BUR 2.38, DDR 33, and output 22 kg/h. The peak polymer recrystallization temperature, permeation, dart drop impact, 1% secant modulus, and tear strength were measured and are reported in Tables F7 and F8.

COMPARATIVE EXAMPLE CF3

Comparative example CF3 was prepared the same way as example F7 except no nucleating agent was used.

TABLE F7

Peak polymer recrystallization temperature ($T_c$), vapor permeation, and dart drop impact of comparative sample CF3 and samples F7.

| Sample | Additive | loading (ppm) | $T_c$ (° C.) | Permeation (g · mil/m² · day) | Impact (g) |
|---|---|---|---|---|---|
| CF3 | None | | 104.0 | 17.3 | 236 |
| F7 | EX46 | 2000 | 112.0 | 19.2 | 333 |

From the data in Tables F7 and F8, it is clear that the additive EX46 increased the peak polymer recrystallization temperature, increased the machine direction tear strength, and dart drop impact.

EXAMPLE F8

This example demonstrates some of the physical properties exhibited by a linear low density polyethylene polymer that has been nucleated with a nucleating agent according to the invention. Polymer compositions were prepared by compounding (as described above) 2000 ppm of EX76 into a commercially-available, linear low density polyethylene polymer (Dowlex™ 2056G) having a density of approximately 0.922 g/cm³ and a melt flow index of approximately 1.0 dg/minute. The formed polymer composition pellet was then used to produce blown films (3 mil thickness) using the following setup: 101.6 mm (4 in) die, 2.0 mm die gap, BUR 2.38, DDR 11, and output 23 kg/h. The peak polymer recrystallization temperature, permeation, dart drop impact, dart drop impact, 1% secant modulus, and tear strength were measured and are reported in Tables F9 and F10.

COMPARATIVE EXAMPLE CF4

Comparative example CF4 was prepared the same way as example F8 except no nucleating agent was used.

TABLE F9

Peak polymer recrystallization temperature ($T_c$) and dart drop impact of comparative sample CF4 and samples F8.

| Sample | Additive | loading (ppm) | $T_c$ (° C.) | Permeation (g · mil/m² · day) | Impact (g) |
|---|---|---|---|---|---|
| CF4 | None | | 104.0 | 18.5 | 725 |
| F8 | EX76 | 2000 | 111.3 | 10.5 | 757 |

TABLE F8

1% Secant Modulus and tear strength of comparative sample CF3 and samples F7.

| Sample | Machine Direction 1% Secant (MPa) | Machine Direction Std Dev (MPa) | Transverse Direction 1% Secant (MPa) | Transverse Direction Std Dev (MPa) | Machine Direction Tear Strength (g) | Machine Direction Std Dev (g) | Transverse Direction Tear Strength (g) | Transverse Direction Std Dev (g) |
|---|---|---|---|---|---|---|---|---|
| CF3 | 159 | 5 | 171 | 5 | 433 | 32 | 707 | 21 |
| F7 | 156 | 5 | 152 | 3 | 476 | 20 | 618 | 12 |

TABLE F10

1% Secant Modulus and tear strength of comparative sample CF4 and samples F8.

| Sample | Machine Direction 1% Secant (MPa) | Std Dev (MPa) | Transverse Direction 1% Secant (MPa) | Std Dev (MPa) | Machine Direction Tear Strength (g) | Std Dev (g) | Transverse Direction Tear Strength (g) | Std Dev (g) |
|---|---|---|---|---|---|---|---|---|
| CF4 | 174 | 4 | 183 | 3 | 1587 | 47 | 1771 | 76 |
| F8 | 224 | 15 | 172 | 3 | 1421 | 51 | 1341 | 29 |

From the data in Tables F9 and F10, it is clear that additive EX76 increased the crystalline peak temperature, dart drop impact, and MD 1% secant modulus. Also, it provides a balanced tear strength in the machine and transverse directions.

EXAMPLE F9

This example demonstrates some of the physical properties exhibited by a linear low density polyethylene polymer that has been nucleated with a nucleating agent according to the invention. Polymer compositions were prepared by compounding (as described above) 2000 ppm of EX5 into a commercially-available, linear low density polyethylene polymer (Dow Elite™ 5100G) having a density of approximately 0.922 g/cm$^3$ and a melt flow index of approximately 0.85 dg/minute. The formed polymer composition pellet was then used to produce blown films (2 and 3 mil thickness) the following setup: 101.6 mm (4 in) die, 2.0 mm die gap, BUR 2.38, DDR 16.5 and 11 respectively for 2 mil and 3 mil films, and output 30 kg/h. The peak polymer recrystallization temperature, permeation, 1% secant modulus, and tear strength were measured and are reported in Tables F11 and F12.

EXAMPLE F10

Example F10 was prepared the same way as example F9 except EX46 was used in the place of EX5.

EXAMPLE F11

Example F11 was prepared the same way as example F9 except EX76 was used in the place of EX5.

COMPARATIVE EXAMPLE CF5

Comparative example CF1 was prepared the same way as example F9 except no nucleating agent was used.

TABLE F11

Peak polymer recrystallization temperature (T$_c$) and vapor permeation of comparative sample CF1 and samples F9, F10, and F11.

| Sample | Additive | loading (ppm) | T$_c$ (° C.) | Thickness | Permeation (g · mil/m$^2$ · day) |
|---|---|---|---|---|---|
| CF5 | None | | 106.3 | 2 mil | 15.6 |
| | | | | 3 mil | 13.7 |
| F9 | EX5 | 2000 | 114.3 | 2 mil | 15.7 |
| | | | | 3 mil | 15.4 |
| F10 | EX46 | 2000 | 113.5 | 2 mil | 17.6 |
| | | | | 3 mil | 15.8 |
| F11 | EX76 | 2000 | 112.7 | 2 mil | 10.8 |
| | | | | 3 mil | 9.8 |

TABLE F12

Tear strength of comparative sample CF1 and samples F9, F10, and F11.

| Sample | Thickness (mil) | Machine Direction Tear Strength (g) | Std dev (g) | Transverse Direction Tear Strength (g) | Std dev (g) | Machine Direction 1% Secant (MPa) | Std Dev (MPa) | Transverse Direction 1% Secant (MPa) | Std Dev (MPa) |
|---|---|---|---|---|---|---|---|---|---|
| CF5 | 2 | 721 | 33 | 1057 | 26 | 165 | 5 | 177 | 5 |
| | 3 | 1089 | 37 | 1518 | 34 | 171 | 4 | 184 | 10 |
| F9 | 2 | 720 | 26 | 1083 | 16 | 159 | 4 | 164 | 5 |
| | 3 | 1214 | 43 | 1645 | 22 | 166 | 5 | 180 | 7 |
| F10 | 2 | 774 | 30 | 1100 | 24 | 159 | 3 | 172 | 8 |
| | 3 | 1173 | 57 | 1608 | 31 | 170 | 6 | 178 | 7 |
| F11 | 2 | 632 | 25 | 921 | 21 | 228 | 19 | 181 | 5 |
| | 3 | 1030 | 40 | 1276 | 23 | 239 | 3 | 178 | 9 |

From the data in Tables F11-F12, it is clear that additives, EX5, EX46, and EX76 increased the peak polymer recrystallization temperature. In addition, EX5 and EX46 increased the machine direction tear strength, especially when the film was 3 mil thick. EX76 increased the tensile modulus in the machine direction and generated more balanced tear strength in the machine and transverse directions. EX5 and EX46 increased the permeation while EX76 reduced permeation.

Manufacture of Nucleated Polyethylene by Injection Molding

In the following injection molding examples, the polyethylene resins used were first ground to a 35 mesh powder. Then, the inventive nucleating agent was added to the resin and blended in a Henschel high intensity mixer for about 2 minutes with a blade speed of about 2100 rpm. The samples were then melt compounded on a DeltaPlast single screw extruder, with a 25 mm diameter screw and a length to diameter ratio of 30:1. The barrel temperature of the extruder was ramped from 160 to 190° C. and the screw speed was set at about 130 rpm. The extrudate in the form of a strand, was cooled in a water bath and then subsequently pelletized.

Plaques and bars were formed through injection molding on an Arburg 40 ton injection molder with a 25.4 mm diameter screw. The barrel temperature of the injection molder was 230° C. unless otherwise specified and the mold temperature was controlled at 25° C.

Unless otherwise specified, the injection speed for the plaques was 2.4 cc/sec, and their dimensions are about 60 mm long, 60 mm wide and 2 mm thick. These plaques were used to measure recrystallization temperature, bi-directional stiffness, and multi-axial impact resistance.

Unless otherwise specified, the injection speed for the bars was 15 cc/sec, and their dimensions are about 127 mm long, 12.7 mm wide and 3.3 mm thick. These bars were used to measure 1% secant modulus, HDT and Izod impact resistance.

Testing of Nucleated Polyethylene

Flexural properties testing (reported as bi-directional modulus) was performed on the above mentioned plaques using an MTS Q-Test-5 instrument with a span of 32 mm, a fixed deflection rate of 8.53 mm/minute, and a nominal sample width of 50.8 mm. Samples were prepared by cutting square sections (approximately 50 mm×50 mm) from the centers of the plaques in order to obtain an isotropically sized sample. In addition to testing the samples across the machine/flow direction as is customary (labeled as "Transverse Direction" in the results table), samples were also tested by flexing across the transverse direction to flow to measure stiffness in that direction as well (labeled as "Machine Direction" in the results table) in order to examine the bi-directional stiffness of the plaques.

Multi-axial Impact testing was performed in the above mentioned plaques using an Instron Ceast 9350 tester according to ISO 6603 standard, using a 2.2 m/sec speed and a chamber temperature of −30° C. Flexural modulus testing (reported as 1% secant modulus) was performed in the above mentioned bars using a MTS Qtest/5 instrument, according to ASTM D790 procedure B. Heat deflection temperature was performed in the above mentioned bars using a Ceast HDT 3 VICAT instrument, according to ASTM D648-07 method B. Izod impact testing was performed in the above mentioned bars, using a Tinius-Olsen 892T instrument, according to ASTM D256, method A.

The peak polymer recrystallization temperature ($T_c$) for the thermoplastic polymer compositions was measured using a differential scanning calorimeter (Mettler-Toledo DSC822 differential scanning calorimeter). In particular, a sample was taken from the target part and heated at a rate of 20° C./minute from a temperature of 60° C. to 220° C., held at 220° C. for two minutes, and cooled at a rate of approximately 10° C./minute to a temperature of 60° C. The temperature at which peak polymer crystal reformation occurred (which corresponds to the peak polymer recrystallization temperature) was recorded for each sample.

EXAMPLE I1-I3

These examples demonstrate some of the physical properties exhibited by a high density polyethylene polymer that has been nucleated with nucleating agents according to the invention. Polymer compositions were prepared by compounding (as described above) Preparation Example EX5 and different acid scavengers into a commercially available high density polyethylene (Dowlex™ IP 40) having a density of approximately 0.954 g/cm$^3$ and a melt flow index of approximately 40 dg/minute. The resin was first ground, mixed with the additives, and then compounded and extruded to form pellets. The formed polymer composition pellet was then injection molded into testing plaques and bars.

The formulation information for Examples I1 to I3 and Comparative Example CI1 is listed in table I1. The peak polymer recrystallization temperature (Tc), multi-axial impact at temperatures of −30° C. and bi-directional modulus (measured on plaques), and 1% secant modulus and heat deflection temperature (measured on bars) are reported in Tables I2 and I3 below.

TABLE I1

Formulation information for Samples CI1, I1, I2 and I3.

| | Additives | | |
|---|---|---|---|
| Examples | EX5 | Zinc Stearate | DHT-4A |
| CI1 | None | None | None |
| I1 | 1500 ppm | None | None |
| I2 | 1500 ppm | 1500 ppm | None |
| I3 | 1500 ppm | None | 500 ppm |

TABLE I2

Multi-axial impact at temperature of −30° C. and bi-directional modulus of sample CI1, I1, I2 and I3.

| | Multi-Axial Impact (2.2 m/s at −30° C.) | | | | Bi-directional Modulus | | | |
|---|---|---|---|---|---|---|---|---|
| Sample | Total Energy (J) | Std Dev (J) | Ductility Index | Std Dev | Machine Direction (MPa) | Std Dev (MPa) | Transverse Direction (MPa) | Std Dev (MPa) |
| CI1 | 12.0 | 0.5 | 2.6 | 0.5 | 988 | 6 | 1060 | 3 |
| I1 | 15.5 | 0.8 | 7.8 | 1.5 | 1069 | 2 | 1053 | 15 |
| I2 | 13.4 | 1.5 | 4.3 | 1.7 | 979 | 12 | 1129 | 10 |
| I3 | 16.7 | 1.2 | 13.1 | 3.8 | 1058 | 3 | 1062 | 6 |

TABLE I3

1% secant modus, heat deflection temperature, and peak polymer recrystallization temperature of CI1, I1, I2, and I3.

| Sample | 1% Secant Modulus (MPa) | Std Dev (MPa) | Heat Deflection temperature (° C.) | $T_c$ (° C.) |
|---|---|---|---|---|
| CI1 | 810 | 1 | 61 | 116.0 |
| I1 | 862 | 14 | 69 | 117.8 |
| I2 | 788 | 4 | 61 | 117.7 |
| I3 | 856 | 12 | 68 | 118.3 |

EXAMPLE I4-I6

These examples demonstrate some of the physical properties exhibited by a high density polyethylene polymer that has been nucleated with nucleating agents according to the invention. Polymer compositions were prepared by compounding (as described above) Preparation Example EX46 and different acid scavengers into commercially available high density polyethylene (Dowlex™ IP 40) having a density of approximately 0.954 g/cm³ and a melt flow index of approximately 40 dg/minute. The resin was first ground, mixed with the additives, and then compounded and extruded to form pellets. The formed polymer composition pellet was then injection molded into testing plaques and bars. The formulation information for examples I4 to I6 and Comparative Example CI2 is listed in Table I4. The peak polymer recrystallization temperature ($T_c$), multi-axial impact at temperature of −30° C. and bi-directional modulus (measured on plaques), and 1% secant modulus and heat deflection temperature (measured on bars) are reported in Table I5 and I6 below.

TABLE I4

Formulation information for Samples CI2, I4, I5 and I6.

| | Additives | | |
|---|---|---|---|
| Examples | EX46 | Calcium Stearate | DHT-4A |
| CI2 | None | None | None |
| I4 | 1500 ppm | None | None |
| I5 | 1500 ppm | 1500 ppm | None |
| I6 | 1500 ppm | None | 500 ppm |

TABLE I5

Multi-axial impact at temperature of −30° C. and bi-directional modulus of sample CI2, I4, I5 and I6

| | Multi-Axial Impact (2.2 m/s at −30° C.) | | | | Bi-directional Modulus | | | |
|---|---|---|---|---|---|---|---|---|
| Sample | Total Energy (J) | Std Dev (J) | Ductility Index | Std Dev | Machine Direction (MPa) | Std Dev (MPa) | Transverse Direction (MPa) | Std Dev (MPa) |
| CI2 | 13.1 | 0.8 | 4.0 | 1.2 | 946 | 10 | 1017 | 14 |
| I4 | 18.1 | 1.5 | 12.7 | 4.8 | 978 | 8 | 991 | 3 |
| I5 | 16.8 | 1.2 | 8.7 | 3.5 | 946 | 15 | 1022 | 1 |
| I6 | 17.5 | 0.4 | 10.2 | 2.5 | 998 | 13 | 1009 | 5 |

TABLE I6

1% secant modus, peak polymer recrystallization temperature, and heat deflection temperature of CI2, I4, I5 and I6.

| | Property | | | |
|---|---|---|---|---|
| Sample | 1% Secant Modulus (MPa) | Std Dev (MPa) | Heat Deflection temperature (° C.) | $T_c$ (° C.) |
| CI2 | 839 | 7 | 63 | 116.2 |
| I4 | 882 | 5 | 67 | 117.2 |
| I5 | 850 | 8 | 65 | 117.2 |
| I6 | 879 | 6 | 68 | 118.0 |

EXAMPLE I7

This example demonstrates some of the physical properties exhibited by a high density polyethylene polymer that has been nucleated with nucleating agents according to the invention. Polymer compositions were prepared by compounding (as described above) Preparation Example EX76 into a commercially available high density polyethylene (Dowlex™ IP 40) having a density of approximately 0.954 g/cm³ and a melt flow index of approximately 40 dg/minute. The resin was first ground, mixed with the additives, and then compounded and extruded to form pellets. The formed polymer composition pellet was then injection molded into testing plaques and bars. The formulation information for Example I7 and Comparative Example CI3 is listed in Table I7. The peak polymer recrystallization temperature ($T_c$), multi-axial impact at temperature of −30° C. and bi-directional modulus (measured on plaques), and 1% secant modulus and heat deflection temperature (measured on bars) were measured and reported in Table I8 and I9 below.

TABLE I7

Formulation information for Samples CI3 and I7.

| | Additives | | |
|---|---|---|---|
| Examples | EX76 | Calcium Stearate | DHT-4A |
| CI3 | None | None | None |
| I7 | 2000 ppm | None | None |

TABLE I8

Multi-axial impact at temperature of −30° C. and bi-directional modulus of samples CI3 and I7

| | Property | | | | | | | |
|---|---|---|---|---|---|---|---|---|
| | Multi-Axial Impact (2.2 m/s at −30° C.) | | | | Bi-directional Modulus | | | |
| Sample | Total Energy (J) | Std Dev (J) | Ductility Index | Std Dev | Machine Direction (MPa) | Std Dev (MPa) | Transverse Direction (MPa) | Std Dev (MPa) |
| CI3 | 11.6 | 4.9 | 3.0 | 0.7 | 931 | 15 | 957 | 11 |
| I7 | 17.3 | 0.9 | 14.0 | 5.0 | 918 | 8 | 989 | 12 |

TABLE I9

1% secant modulus, heat deflection temperature, and peak polymer recrystallization temperature of CI3 and I7.

| | Property | | | |
|---|---|---|---|---|
| Sample | 1% Secant Modulus (MPa) | Std Dev (MPa) | Heat Deflection temperature (° C.) | $T_c$ (° C.) |
| CI3 | 805 | 1 | 61 | 116.3 |
| I7 | 888 | 14 | 70 | 117.7 |

EXAMPLE I8-I10

These examples demonstrate some of the physical properties exhibited by a high density polyethylene polymer that has been nucleated with nucleating agents according to the invention. Polymer compositions were prepared by compounding (as described above) Preparation Example EX5 and different acid scavengers into a commercially available high density polyethylene (ExxonMobil™ HDPE HD 6719) having a density of approximately 0.952 g/cm³ and a melt flow index of approximately 19 dg/minute. The resin was first ground, mixed with the additives, and then compounded and extruded to form pellets. The formed polymer composition pellet was then injection molded into testing plaques and bars. The formulation information for Examples I8 to I10 and Comparative Example CI4 is listed in Table I10. The peak polymer recrystallization temperature, multi-axial impact at temperature of −30° C. and bi-directional modulus (measured on plaques), and 1% secant modulus and heat deflection temperature (measured on bars) were measured and are reported in Table I11 and I12 below.

TABLE I10

Formulation information for Samples CI4, I8, I9 and I10.

| | Additives | | |
|---|---|---|---|
| Examples | EX5 | Calcium Stearate | DHT-4A |
| CI4 | None | None | None |
| I8 | 1500 ppm | None | None |
| I9 | 1500 ppm | 1500 ppm | None |
| I10 | 1500 ppm | None | 500 ppm |

TABLE I11

Multi-axial impact at temperature of −30° C. and bi-directional modulus of sample CI4, I8, I9 and I10.

| | Property | | | | | | | |
|---|---|---|---|---|---|---|---|---|
| | Multi-Axial Impact (2.2 m/s at −30° C.) | | | | Bi-directional Modulus | | | |
| Sample | Total Energy (J) | Std Dev (J) | Ductility Index | Std Dev | Machine Direction (MPa) | Std Dev (MPa) | Transverse Direction (MPa) | Std Dev (MPa) |
| CI4 | 28.4 | 0.6 | 42.5 | 0.7 | 1020 | 12 | 1142 | 7 |
| I8 | 29.9 | 0.3 | 44.9 | 1.0 | 1137 | 4 | 1128 | 7 |
| I9 | 29.6 | 0.4 | 44.9 | 0.7 | 1107 | 4 | 1130 | 11 |
| I10 | 29.9 | 0.7 | 45.4 | 1.3 | 1143 | 13 | 1129 | 14 |

TABLE I12

1% secant modulus, heat deflection temperature, and peak polymer recrystallization temperature of CI4, I8, I9 and I10.

| | Property | | | |
|---|---|---|---|---|
| Sample | 1% Secant Modulus (MPa) | Std Dev (MPa) | Heat Deflection temperature (° C.) | $T_c$ (° C.) |
| CI4 | 869 | 13 | 64 | 117.2 |
| I8 | 948 | 10 | 69 | 119.7 |
| I9 | 916 | 5 | 70 | 119.3 |
| I10 | 957 | 10 | 71 | 120.0 |

EXAMPLE I11-I12

These examples demonstrate some of the physical properties exhibited by a high density polyethylene polymer that has been nucleated with nucleating agents according to the invention. Polymer compositions were prepared by compounding (as described above) Preparation Examples EX46 and EX76 into a commercially available high density polyethylene (ExxonMobil™ HDPE HD 6719) having a density of approximately 0.952 g/cm³ and a melt flow index of approximately 19 dg/minute. The resin was first ground, mixed with the additives, and then compounded and extruded to form pellets. The formed polymer composition pellet was then injection molded into testing plaques and bars. In this example, the plaques were molded at 15 cc/sec and the bars at 40 cc/sec, keeping the other processing conditions the same as described above. The formulation information for Examples I11 and I12 and Comparative Example CI5 is listed in Table I13. The peak polymer recrystallization temperature, multi-axial impact at temperature of −30° C. and bi-directional modulus (measured on plaques), and 1% secant modulus, izod impact at −30° C., and heat distortion temperature (measured on bars) were measured and are reported in Table I14 and I15 below.

TABLE I13

Formulation information for Samples CI5, I11 and I12.

| | Additives | |
|---|---|---|
| Examples | EX46 | EX76 |
| CI5 | None | None |
| I11 | 2000 ppm | None |
| I12 | None | 2000 ppm |

TABLE I14

Multi-axial impact at temperature of −30° C. and Bi-directional modulus of sample CI5, I11 and I12. Plaques molded at 15 cc/sec

| | Property | | | | | | | |
|---|---|---|---|---|---|---|---|---|
| | Multi-Axial Impact (2.2 m/s at −30° C.) | | | | Bi-directional Modulus | | | |
| Sample | Total Energy (J) | Std Dev (J) | Ductility Index | Std Dev | Machine Direction (MPa) | Std Dev (MPa) | Transverse Direction (MPa) | Std Dev (MPa) |
| CI5 | 30.6 | 0.3 | 45.9 | 0.4 | 879 | 9 | 952 | 9 |
| I11 | 31.4 | 0.7 | 45.6 | 0.9 | 958 | 12 | 957 | 13 |
| I12 | 29.9 | 0.1 | 46.7 | 0.4 | 890 | 6 | 1162 | 4 |

TABLE I15

1% secant modulus, peak polymer recrystallization temperature, and heat deflection temperature of CI5, I11 and I12. Bars molded at 40 cc/sec

| | Property | | | | | |
|---|---|---|---|---|---|---|
| Sample | 1% Secant Modulus (MPa) | Std Dev (MPa) | Izod Impact (J/m) | Std Dev (J/m) | Heat Deflection temperature (° C.) | $T_c$ (° C.) |
| CI5 | 854 | 3 | 30.6 | 6.3 | 67 | 116.8 |
| I11 | 915 | 8 | 32.8 | 1.9 | 69 | 118.8 |
| I12 | 965 | 1 | 33.2 | 1.1 | 71 | 119.0 |

EXAMPLE I13-I15

These examples demonstrate some of the physical properties exhibited by a high density polyethylene polymer that has been nucleated with nucleating agents according to the invention. Polymer compositions were prepared by compounding Preparation Examples EX5, EX46 and EX76 into a commercially available high density polyethylene (LyondellBasell Hostalen® ACP 6541A UV) having a density of approximately 0.954 g/cm³ and a melt flow index of approximately 1.5 dg/minute. The resin was first ground, mixed with the additives, and then compounded and extruded to form pellets. The formed polymer composition pellet was then injection molded into testing plaques and bars. In this example, the plaques were molded at 220° C. and 20 cc/sec and the bars were molded at 220° C. and 40 cc/sec, keeping the other processing conditions the same as described above. The formulation information for Examples I13, I14, I15 and Comparative Example CI6 is listed in Table I16. The peak polymer recrystallization temperature, multi-axial impact at temperature of −30° C. and bi-directional modulus (measured on plaques), and 1% secant modulus, Izod impact, and heat deflection temperature (measured on bars) were measured and are reported in Table I17 and I18 below.

TABLE I16

Formulation information for Samples CI6, I13, I14 and I15.

| | Additives | | |
|---|---|---|---|
| Examples | EX5 | EX46 | EX76 |
| CI6 | None | None | None |
| I13 | 2000 ppm | None | None |
| I14 | None | 2000 ppm | None |
| I15 | None | None | 2000 ppm |

TABLE I17

Multi-axial impact at temperature of −30° C. and bi-directional modulus of sample CI6, I13, I14 and I15. Plaques molded at 20 cc/sec

| | Property | | | | | | | |
|---|---|---|---|---|---|---|---|---|
| | Multi-Axial Impact (2.2 m/s at −30° C.) | | | | Bi-directional Modulus | | | |
| Sample | Total Energy (J) | Std Dev (J) | Ductility Index | Std Dev | Machine Direction (MPa) | Std Dev (MPa) | Transverse Direction (MPa) | Std Dev (MPa) |
| CI6 | 30.3 | 0.5 | 43.8 | 0.8 | 1016 | 7 | 1239 | 4 |
| I13 | 29.9 | 0.2 | 43.5 | 1.0 | 1061 | 14 | 1305 | 8 |
| I14 | 29.9 | 0.4 | 42.6 | 1.0 | 1057 | 3 | 1314 | 4 |
| I15 | 28.3 | 0.3 | 44.5 | 1.0 | 1052 | 12 | 1198 | 11 |

TABLE I18

1% secant modulus, peak polymer recrystallization temperature, and heat deflection temperature of CI6, I13, I14 and I15.

| Sample | Property | | | | | |
|---|---|---|---|---|---|---|
| | 1% Secant Modulus (MPa) | Std Dev (MPa) | Izod Impact (J/m) | Std Dev (J/m) | Heat Deflection temperature (°C.) | $T_c$ (°C.) |
| CI6 | 923 | 13 | 46.7 | 1.4 | 61 | 117.0 |
| I13 | 894 | 9 | 48.7 | 1.4 | 53 | 119.2 |
| I14 | 858 | 6 | 47.2 | 1.3 | 54 | 119.0 |
| I15 | 1061 | 4 | 36.2 | 1.7 | 80 | 118.5 |

Manufacture of Nucleated Thin Wall Injection Molded Deli-Cups

The polyethylene resins used were first ground to a 35 mesh powder. The inventive nucleating agent was added to the resin and blended in a Henschel high intensity mixer for about 2 minutes with a blade speed of about 2100 rpm. The samples were then melt compounded in a MPM single screw extruder, with a 38 mm diameter screw. The barrel temperature of the extruder was ramped from 160 to 190° C. The extrudate in the form of strands, was cooled in a water bath and then subsequently pelletized. Deli-cups with a volumetric capacity of 16 oz. were produced in a Husky S-90 RS40/32 injection molder, 90 ton clamp and accumulator assisted/high speed injection unit, using a single cavity mold. The injection molder has a 32 mm diameter reciprocating screw, with a length to diameter ratio of 25:1. The barrel temperature of the extruder was between 190 and 210° C. depending on the melt index of the resin, with the hot runners temperatures also set at about 210° C. The mold temperature was set at about 12° C. The dimensions of the Deli-cups are approximately 117 mm diameter and 76 mm high.

Testing of Nucleated Polyethylene Deli Cups

The % haze of the parts was measured on the side wall using a BYK Gardner Haze meter, according to ASTM D1023. The clarity of the parts was measured on the side wall using a BYK Gardner Haze meter. The top load of the parts was measured using a MTS Q-Test-5 instrument according to ASTM D 2659. The peak polymer recrystallization temperature ($T_c$) for the thermoplastic polymer compositions was measured using a differential scanning calorimeter (Mettler-Toledo DSC822 differential scanning calorimeter). In particular, a compression molded plaque was prepared from the pellets and a sample was taken from the plaque and heated at a rate of 20° C./minute from a temperature of 60° C. to 220° C., held at 220° C. for two minutes, and cooled at a rate of approximately 10° C./minute to a temperature of 60° C. The temperature at which peak polymer crystal reformation occurred (which corresponds to the peak polymer recrystallization temperature) was recorded for each sample.

EXAMPLE I16-I18

These examples demonstrate some of the physical properties exhibited by high density polyethylene polymer articles (Deli-cups) that have produced using a composition containing a nucleating agent according to the invention. The polyethylene articles were prepared by compounding (as described above) Preparation Examples EX5, EX46, and EX76 into a commercially available high density polyethylene (Dowlex IP 40) having a density of approximately 0.954 g/cm³ and a melt flow index of approximately 40 dg/minute. The resin was first ground, mixed with the additives, and then compounded and extruded to form pellets as described above. The formed polymer composition pellet was then processed by thin wall injection molding (TWIM) to form the polyethylene articles. In this example, the Deli-cups were produced using a fill time of 0.21 sec. The formulation information for Examples I16, I17, I18 and Comparative Example CI7 is listed in Table I19. The recrystallization peak time (measured in a compression molded plaque produced with the pellets), the clarity, haze, and the top load of the deli cups were measured and reported in Table I20 below.

TABLE I19

Formulation information for Samples CI7 and I16 to I18.
All the compositions contain 1000 ppm of
Irganox1010 and 800 ppm of Irgafos 168.

| Examples | Additives | | |
|---|---|---|---|
| | EX5 | EX46 | EX76 |
| CI7 | 0 | 0 | 0 |
| I16 | 1500 ppm | 0 | 0 |
| I17 | 0 | 1500 ppm | 0 |
| I18 | 0 | 0 | 1500 ppm |

TABLE I20

Select physical properties of Comparative Samples CI17 and sample I16 to I18.

| Sample | Properties | | | | | |
|---|---|---|---|---|---|---|
| | DSC $T_c$ (°C.) | Optical Properties | | | | Top Load | |
| | | Haze | Std Dev | Clarity | Std Dev | Peak Load (N) | Std Dev |
| CI17 | 114.3 | 98.2 | 0.11 | 75.1 | 0.89 | 658 | 10 |
| I16 | 117.2 | 77.6 | 0.41 | 96.1 | 0.11 | 698 | 14 |
| I17 | 115.7 | 79.6 | 0.22 | 97.4 | 0.08 | 705 | 12 |
| I18 | 116.5 | 88.1 | 0.08 | 95.7 | 0.09 | 653 | 9 |

Manufacture of Nucleated Injection Molded Food Storage Container

The polyethylene resins used were first ground to a 35 mesh powder. The inventive nucleating agents were added to the resin and blended in a Henschel high intensity mixer for about 2 minutes with a blade speed of about 2100 rpm. The samples were then melt compounded in a MPM single screw extruder, with a 38 mm diameter screw. The barrel temperature of the extruder was ramped from 160 to 190° C. The extrudate in the form of strands, was cooled in a water bath and then subsequently pelletized. Reusable food storage containers with an approximate weight of 62 g were produced in a Husky S-90 RS40/32 injection molder, 90 ton clamp and accumulator assisted/high speed injection unit, using a single cavity mold. The injection molder has a 32 mm diameter reciprocating screw, with a length to diameter ratio of 25:1. The barrel temperature of the extruder was between 190 and 220° C. depending on the melt index of the resin, with the hot runners temperatures also set at about 220° C. The mold temperature was set at about 12° C. The dimensions of the food storage containers are 190.5 mm×98.4 mm×76.2 mm, and the wall thickness is about 1 mm.

Testing of nucleated polyethylene food storage containers

The % haze of the parts was measured on the side wall using a BYK Gardner Haze meter, according to ASTM D1023. The clarity of the parts was measured on the side wall using a BYK Gardner Haze meter. The top load of the parts was measured using a MTS Q-Test-5 instrument according to ASTM D 2659. The peak polymer recrystallization temperature ($T_c$) for the thermoplastic polymer compositions was measured using a differential scanning calorimeter (Mettler-Toledo DSC822 differential scanning calorimeter). In particular, a compression molded plaque was prepared from the pellets and a sample was taken from the plaque and heated at a rate of 20° C./minute from a temperature of 60° C. to 220° C., held at 220° C. for two minutes, and cooled at a rate of approximately 10° C./minute to a temperature of 60° C. The temperature at which peak polymer crystal reformation occurred (which corresponds to the peak polymer recrystallization temperature) was recorded for each sample.

EXAMPLE H1-H3

These examples demonstrate some of the physical properties exhibited by a high density polyethylene polymer article (food storage container) that has been nucleated with nucleating agents according to the invention. The polyethylene articles were prepared by compounding Preparation Examples EX5, EX46, and EX76 into a commercially available high density polyethylene (ExxonMobil™ HDPE HD 6719) having a density of approximately 0.952 g/cm³ and a melt flow index of approximately 19 dg/minute. The resin was first ground, mixed with the additives, and then compounded and extruded to form pellets as described above. The formed polymer composition pellet was then processed by injection molding (IM) to form the polyethylene articles. In this example, the Housewares were produced using a fill time of 2.8 sec. The formulation information for Examples H1, H2, H3 and Comparative Example CH1 is listed in Table TH1. The recrystallization peak time (measured in a compression molded plaque produced with the pellets), the clarity, haze, and the top load were measured and are reported in Table TH2 below.

TABLE TH1

Formulation information for Samples CH1 and H1 to H3.
All the compositions contain 1000 ppm of
Irganox1010 and 800 ppm of Irgafos 168.

| Examples | Additives | | |
|---|---|---|---|
| | EX5 | EX46 | EX76 |
| CH1 | 0 | 0 | 0 |
| H1 | 1500 ppm | 0 | 0 |
| H2 | 0 | 1500 ppm | 0 |
| H3 | 0 | 0 | 1500 ppm |

TABLE TH2

Select physical properties of Comparative Samples
CH1 and H1 to H3.

| Sample | Properties | | | | | |
|---|---|---|---|---|---|---|
| | DSC $T_c$ (° C.) | Optical Properties | | | | Top Load | |
| | | Haze | Std Dev | Clarity | Std Dev | Peak Load (N) | Std Dev |
| CH1 | 114.5 | 103.0 | 0.5 | 2.8 | 0.1 | 1594 | 26 |
| H1 | 118.2 | 96.5 | 0.3 | 91.9 | 0.2 | 1632 | 29 |
| H2 | 117.7 | 97.5 | 0.2 | 93.5 | 0.1 | 1691 | 14 |
| H3 | 118.0 | 99.7 | 0.1 | 89.2 | 0.1 | 1690 | 11 |

EXAMPLE H4-H6

These examples demonstrate some of the physical properties exhibited by a high density polyethylene polymer article (food storage container) that has been made with a resin nucleated with a nucleating agent according to the invention. Polyethylene articles were prepared by compounding Preparation Examples EX5, EX46, and EX76 into a commercially available high density polyethylene (Dow™ HDPE DMDA-8965 NT 7) having a density of approximately 0.954 g/cm³ and a melt flow index of approximately 66 dg/minute. The resin was first ground, mixed with the additives, and then compounded and extruded to form pellets as described above. The formed polymer composition pellet was then processed by injection molding (IM) to form the polyethylene articles. In this example, the housewares were produced using a fill time of 3.0 sec. The formulation information for Examples H4, H5, H6 and Comparative Example CH2 is listed in Table TH3. The recrystallization peak time (measured in a compression molded plaque produced with the pellets), the clarity, haze, and the top load were measured and are reported in Table TH4 below.

TABLE TH3

Formulation information for Samples CH2 and H4 to H6.
All the compositions contain 1000 ppm of
Irganox1010 and 800 ppm of Irgafos 168.

| Examples | Additives | | |
|---|---|---|---|
| | EX5 | EX46 | EX76 |
| CH2 | 0 | 0 | 0 |
| H4 | 1500 ppm | 0 | 0 |
| H5 | 0 | 1500 ppm | 0 |
| H6 | 0 | 0 | 1500 ppm |

TABLE TH4

Select physical properties of Comparative Samples
CH2 and H4 to H6.

| Sample | Properties | | | | | |
|---|---|---|---|---|---|---|
| | DSC $T_c$ (° C.) | Optical Properties | | | | Top Load | |
| | | Haze | Std Dev | Clarity | Std Dev | Peak Load (N) | Std Dev |
| CH2 | 113.5 | 103.0 | 0.0 | 2.1 | 0.3 | 1659 | 11 |
| H4 | 118.5 | 98.4 | 0.1 | 91.2 | 0.3 | 1731 | 12 |
| H5 | 117.3 | 100.0 | 0.0 | 89.9 | 0.1 | 1690 | 15 |
| H6 | 118.0 | 101.0 | 0.0 | 83.8 | 0.4 | 1737 | 8 |

EXAMPLE H7-H9

These examples demonstrate some of the physical properties exhibited by a high density polyethylene polymer article (food storage container) that has been produced using a resin nucleated with a nucleating agent according to the invention. Polyethylene articles were prepared by compounding Preparation Examples EX5, EX46, and EX76 into a commercially available linear low density polyethylene (ExxonMobil™ LLDPE LL 6100.17) having a density of approximately 0.925 g/cm³ and a melt flow index of approximately 20 dg/minute. The resin was first ground, mixed with the additives, and then compounded and extruded to form pellets as described above. The formed polymer composition pellet was then processed by injection molding (IM) to form the polyethylene articles. In this example, the housewares were produced using a fill time of 2.7 sec. The formulation information for Exmaples H7, H8, H9 and Comparative Example CH3 is listed in Table TH5. The recrystallization peak time (measured in a compression molded plaque produced with the pellets), the clarity, haze, and the top load were measured and are reported in Table TH6 below.

TABLE TH5

Formulation information for Samples CH3 and H7 to H9.
All the compositions contain 1000 ppm of
Irganox1010 and 800 ppm of Irgafos 168.

| | Additives | | |
|---|---|---|---|
| Examples | EX5 | EX46 | EX76 |
| CH3 | 0 | 0 | 0 |
| H7 | 1500 ppm | 0 | 0 |
| H8 | 0 | 1500 ppm | 0 |
| H9 | 0 | 0 | 1500 ppm |

TABLE TH6

Select physical properties of comparative samples
CH3 and H7 to H9.

| | Properties | | | | | |
|---|---|---|---|---|---|---|
| | | Optical Properties | | | Top Load | |
| Sample | DSC $T_c$ (° C.) | Haze | Std Dev | Clarity | Std Dev | Peak Load (N) | Std Dev |
| CH3 | 106.5 | 90.0 | 0.1 | 93.2 | 0.2 | 618 | 8 |
| H7 | 115.3 | 78.0 | 0.1 | 95.2 | 0.1 | 642 | 8 |
| H8 | 114.2 | 78.6 | 0.3 | 96.5 | 0.1 | 650 | 9 |
| H9 | 114.5 | 86.1 | 0.1 | 95.7 | 0.1 | 646 | 4 |

EXAMPLE H10-H12

These examples demonstrate some of the physical properties exhibited by a high density polyethylene polymer article (food storage container) that has been made with a resin nucleated with a nucleating agent according to the invention. Polyethylene articles were prepared by compounding Preparation Examples EX5, EX46, and EX76 into a commercially available linear low density polyethylene (Dowlex™ 2517) having a density of approximately 0.919 g/cm³ and a melt flow index of approximately 25 dg/minute. The resin was first ground, mixed with the additives, and then compounded and extruded to form pellets as described above. The formed polymer composition pellet was then processed by injection molding (IM) to form the polyethylene articles. In this example, the housewares were produced using a fill time of 2.5 sec. The formulation information for Examples H10, H11, H12 and Comparative Example CH4 is listed in Table TH7. The recrystallization peak time (measured in a compression molded plaque produced with the pellets), the clarity, haze, and the top load were measured and are reported in Table TH8 below.

TABLE TH7

Formulation information for Sample CH4 and H10 to H12.
All the compositions contain 1000 ppm of
Irganox1010 and 800 ppm of Irgafos 168.

| | Additives | | |
|---|---|---|---|
| Examples | EX5 | EX46 | EX76 |
| CH4 | 0 | 0 | 0 |
| H10 | 1500 ppm | 0 | 0 |
| H11 | 0 | 1500 ppm | 0 |
| H12 | 0 | 0 | 1500 ppm |

TABLE TH8

Select physical properties of Comparative Samples
CH4 and H10 to H12.

| | Properties | | | | | |
|---|---|---|---|---|---|---|
| | | Optical Properties | | | Top Load | |
| Sample | DSC $T_c$ (° C.) | Haze | Std Dev | Clarity | Std Dev | Peak Load (N) | Std Dev |
| CH4 | 100.3 | 97.0 | 0.1 | 84.9 | 0.2 | 426 | 7 |
| H10 | 116.0 | 78.9 | 0.2 | 95.4 | 0.1 | 471 | 5 |
| H11 | 115.0 | 82.0 | 0.1 | 97.8 | 0.0 | 464 | 5 |
| H12 | 114.0 | 88.8 | 0.3 | 96.7 | 0.1 | 481 | 3 |

Formation of Nucleated Polypropylene

The different additives were added to the polypropylene base resin and blended in a Henschel high intensity mixer for about 2 minutes with a blade speed of about 2100 rpm. The samples were then melt compounded on a DeltaPlast single screw extruder, with a 25 mm diameter screw and a length to diameter ratio of 30:1. The barrel temperature of the extruder was ramped from 190 to 230° C. and the screw speed was set at about 130 rpm. The extrudate in the form of a strand, was cooled in a water bath and then subsequently pelletized.

Plaques and bars were formed through injection molding on an Arburg 40 ton injection molder with a 25.4 mm diameter screw. The barrel temperature of the injection molder was 230° C. and the mold temperature was controlled at 25° C. The injection speed for the plaques was 2.4 cc/sec, and their dimensions are about 60 mm long, 60 mm wide and 2 mm thick. These plaques were used to measure recrystallization temperature, bi-directional stiffness. The injection speed for the bars was 15 cc/sec, and their dimensions are about 127 mm long, 12.7 mm wide and 3.3 mm thick. These bars were used to measure 1% secant modulus, HDT and Izod impact resistance.

Testing of Nucleated Polypropylene

Flexural properties testing (reported bi-directional modulus) was performed on the above mentioned plaques using an MTS Q-Test-5 instrument with a span of 32 mm, a fixed deflection rate of 8.53 mm/minute, and a nominal sample width of 50.8 mm. Samples were prepared by cutting square sections (approximately 50 mm×50 mm) from the centers of the plaques in order to obtain an isotropically sized sample. In addition to testing the samples across the machine/flow direction as is customary (labeled as "Transverse Direction" in the results table), samples were also tested by flexing across the transverse direction to flow to measure stiffness in that direction as well (labeled as "Machine Direction" in the results table) in order to examine the bi-directional stiffness of the plaques.

Flexural modulus testing (reported as 1% secant modulus) was performed in the above mentioned bars using a MTS Qtest/5 instrument, according to ASTM D790 procedure B. Heat deflection temperature was performed in the above mentioned bars using a Ceast HDT 3 VICAT instrument, according to ASTM D648-07 method B. Izod impact testing was performed in the above mentioned bars, using a Tinius-Olsen 892T instrument, according to ASTM D256, method A. The peak polymer recrystallization temperature ($T_c$) for the thermoplastic polymer compositions was measured using a differential scanning calorimeter (Mettler-Toledo DSC822 differential scanning calorimeter). This was accomplished by heating a roughly 5 milligram sample obtained from the target plaques at 20° C./minute from 50° C. to 220° C., holding at 220° C. for 2 minutes, cooling the plaques at a rate of about 20° C./minute back to 50° C., and recording the temperature at which peak polymer crystal reformation occurs (Tc).

EXAMPLE P1-P6

These examples demonstrate some of the physical properties exhibited by a polypropylene polymer that has been nucleated with nucleating agents according to the invention. Polymer compositions were prepared by compounding Preparation Examples EX5, EX46, EX9, EX8, EX36 and EX76 into a commercially available polypropylene homopolymer (LyondellBasell Pro-Fax™ 6301) having a melt flow index of approximately 12 dg/minute. The resin was first mixed with the inventive nucleating agent with antioxidant and acid scavengers, then the mixture compounded and extruded to form pellets. The formed pellet was injection molded into testing plaques and bars as described above. The formulation information for Examples P1 to P6 and Comparative Example CP1 is listed in Table P1. The peak polymer recrystallization temperature, bi-directional modulus, Izod impact, and heat deflection temperature were measured and reported in Table P2 and P3 below.

TABLE P1

Formulation information for Samples CP1 and P1 to P6. All the compositions contain 500 ppm of Irganox 1010, 1000 ppm of Irgafos 168, and 800 ppm of calcium stearate.

| Examples | EX5 | EX46 | EX9 | EX8 | EX36 | EX76 |
|---|---|---|---|---|---|---|
| CP1 | 0 | 0 | 0 | 0 | 0 | 0 |
| P1 | 2000 ppm | 0 | 0 | 0 | 0 | 0 |
| P2 | 0 | 2000 ppm | 0 | 0 | 0 | 0 |
| P3 | 0 | 0 | 2000 ppm | 0 | 0 | 0 |
| P4 | 0 | 0 | 0 | 2000 ppm | 0 | 0 |
| P5 | 0 | 0 | 0 | 0 | 2000 ppm | 0 |
| P6 | 0 | 0 | 0 | 0 | 0 | 2000 ppm |

TABLE P2

Bi-directional modulus of comparative example CP1 and examples P1 to P6

| | Property Bi-directional Modulus | | | |
|---|---|---|---|---|
| Sample | Machine Direction (MPa) | Std Dev (MPa) | Transverse Direction (MPa) | Std Dev (MPa) |
| CP1 | 1599 | 9 | 1562 | 11 |
| P1 | 1840 | 21 | 1818 | 12 |
| P2 | 1744 | 13 | 1759 | 11 |
| P3 | 1709 | 20 | 1750 | 15 |
| P4 | 1695 | 18 | 1771 | 17 |
| P5 | 1745 | 13 | 1711 | 14 |
| P6 | 1681 | 17 | 1652 | 12 |

TABLE P3

Peak polymer recrystallization temperature, Izod impact at room temperature, and heat deflection temperature of comparative example CP1 and examples P1 to P6

| | Property | | | |
|---|---|---|---|---|
| Sample | $T_c$ (° C.) | Izod Impact (J/m) | Std Dev (J/m) | Heat Deflection temperature (° C.) |
| CP1 | 117.8 | 18.0 | 0.3 | 95 |
| P1 | 123.5 | 23.6 | 8.5 | 113 |
| P2 | 122.5 | 33.5 | 6.0 | 110 |
| P3 | 123.5 | 37.6 | 1.4 | 106 |
| P4 | 129.4 | 32.2 | 4.1 | 111 |
| P5 | 128.7 | 32.5 | 6.2 | 108 |
| P6 | 124.4 | 34.3 | 7.3 | 102 |

EXAMPLE P7-P12

These examples demonstrate some of the physical properties exhibited by a polypropylene polymer that has been nucleated with a nucleating agent according to the invention. Polymer compositions were prepared by compounding Preparation Examples EX5, EX46, EX9, EX8, EX36 and EX76 into a commercially available polypropylene homopolymer (LyondellBasell Pro-Fax™ 6301) having a melt flow index of approximately 12 dg/minute. The resin was first mixed with the nucleating agents of invention with antioxidant and acid scavengers, then the mixture compounded and extruded to form pellets. The formed pellet was injection molded into testing plaques and bars as described above. The formulation information for Examples P7 to P12 and Comparative Example CP2 is listed in Table P4. The peak polymer recrystallization temperature, bi-directional modulus, Izod impact, and heat deflection temperature were measured and reported in Table P5 and P6 below.

TABLE P4

Formulation information for Samples CP2 and P7 to P12. All the compositions contain 500 ppm of Irganox 1010, 1000 ppm pf Irgafos 168, and 500 ppm of DHT-4A.

| Examples | Additives | | | | | |
|---|---|---|---|---|---|---|
| | EX5 | EX46 | EX9 | EX8 | EX36 | EX76 |
| CP2 | 0 | 0 | 0 | 0 | 0 | 0 |
| P7 | 2000 ppm | 0 | 0 | 0 | 0 | 0 |
| P8 | 0 | 2000 ppm | 0 | 0 | 0 | 0 |
| P9 | 0 | 0 | 2000 ppm | 0 | 0 | 0 |
| P10 | 0 | 0 | 0 | 2000 ppm | 0 | 0 |
| P11 | 0 | 0 | 0 | 0 | 2000 ppm | 0 |
| P12 | 0 | 0 | 0 | 0 | 0 | 2000 ppm |

TABLE P5

Bi-directional modulus of comparative example CP2 and examples P7 to P12

| Sample | Property Bi-directional Modulus | | | |
|---|---|---|---|---|
| | Machine Direction (MPa) | Std Dev (MPa) | Transverse Direction (MPa) | Std Dev (MPa) |
| CP2 | 1540 | 9 | 1543 | 18 |
| P7 | 1769 | 15 | 1733 | 11 |
| P8 | 1776 | 6 | 1746 | 7 |
| P9 | 1719 | 12 | 1762 | 8 |
| P10 | 1691 | 9 | 1660 | 11 |
| P11 | 1697 | 14 | 1638 | 7 |
| P12 | 1691 | 9 | 1660 | 11 |

TABLE P6

Peak polymer recrystallization temperature, Izod impact at room temperature, and heat deflection temperature of comparative example CP2 and examples P7 to P12

| Sample | $T_c$ (° C.) | Izod Impact (J/m) | Std Dev (J/m) | Heat Deflection temperature (° C.) |
|---|---|---|---|---|
| CP2 | 116.6 | 22.6 | 5.6 | 93 |
| P7 | 126.3 | 32.4 | 6.3 | 111 |
| P8 | 126.4 | 30.1 | 5.8 | 111 |
| P9 | 129.5 | 30.2 | 6.9 | 109 |
| P10 | 127.2 | 31.2 | 7.0 | 108 |
| P11 | 127.7 | 31.7 | 5.3 | 108 |
| P12 | 127.2 | 31.2 | 7.0 | 108 |

EXAMPLE P13-P18

These examples demonstrate some of the physical properties exhibited by a polypropylene polymer that has been nucleated with a nucleating agent according to the invention. Polymer compositions were prepared by compounding Preparation Examples EX5, EX46, EX9, EX8, EX36 and EX76 into a commercially available impact polypropylene copolymer (LyondellBasell Pro-Fax™ SD375S) having a melt flow index of approximately 18 dg/minute.

The resin was first mixed with the nucleating agents of invention with antioxidant and acid scavengers, then the mixture compounded and extruded to form pellets. The formed pellet was injection molded into testing plaques and bars as described above. The formulation information for Examples P13 to P18 and Comparative Example CP3 is listed in Table P7. The peak polymer recrystallization temperature, bi-directional modulus, Izod impact, and heat deflection temperature were measured and reported in Table P8 and P9 below.

TABLE P7

Formulation information for Samples CP3 and P13 to P18. All the compositions contain 500 ppm of Irganox 1010, 1000 ppm of Irgafos 168, and 800 ppm of calcium stearate.

| Examples | Additives | | | | | |
|---|---|---|---|---|---|---|
| | EX5 | EX46 | EX9 | EX8 | EX36 | EX76 |
| CP3 | 0 | 0 | 0 | 0 | 0 | 0 |
| P13 | 2000 ppm | 0 | 0 | 0 | 0 | 0 |
| P14 | 0 | 2000 ppm | 0 | 0 | 0 | 0 |
| P15 | 0 | 0 | 2000 ppm | 0 | 0 | 0 |
| P16 | 0 | 0 | 0 | 2000 ppm | 0 | 0 |
| P17 | 0 | 0 | 0 | 0 | 2000 ppm | 0 |
| P18 | 0 | 0 | 0 | 0 | 0 | 2000 ppm |

TABLE P8

Bi-directional modulus of comparative example CP3 and examples P13 to P18

| Sample | Property Bi-directional Modulus | | | |
|---|---|---|---|---|
| | Machine Direction (MPa) | Std Dev (MPa) | Transverse Direction (MPa) | Std Dev (MPa) |
| CP3 | 1168 | 12 | 1090 | 4 |
| P13 | 1314 | 8 | 1262 | 13 |
| P14 | 1320 | 13 | 1228 | 12 |
| P15 | 1300 | 12 | 1277 | 4 |
| P16 | 1272 | 7 | 1249 | 3 |
| P17 | 1280 | 9 | 1220 | 14 |
| P18 | 1294 | 15 | 1229 | 12 |

TABLE P9

Peak polymer recrystallization temperature, and heat deflection temperature of comparative example CP3 and examples P13 to P18

| Sample | $T_c$ (° C.) | Izod Impact (J/m) | Std Dev (J/m) | Heat Deflection temperature (° C.) |
|---|---|---|---|---|
| CP3 | 117.0 | 107.2 | 9.8 | 76 |
| P13 | 125.9 | 83.4 | 11.2 | 97 |
| P14 | 124.6 | 94.4 | 10 | 96 |
| P15 | 125.2 | 87.4 | 11.7 | 94 |
| P16 | 130.5 | 87.2 | 8.3 | 98 |
| P17 | 128.7 | 83.4 | 10.3 | 96 |
| P18 | 128.3 | 89.8 | 9.2 | 96 |

EXAMPLE P19-P24

These examples demonstrate some of the physical properties exhibited by a polypropylene polymer that has been nucleated with a nucleating agent according to the invention.

Polymer compositions were prepared by compounding Preparation Examples EX5, EX46, EX9, EX8, EX36 and EX76 into a commercially available impact polypropylene copolymer (LyondellBasell Pro-Fax™ SD375S) having a melt flow index of approximately 18 dg/minute.

The resin was first mixed with the nucleating agents of invention with antioxidant and acid scavengers, then the mixture compounded and extruded to form pellets. The formed pellet was injection molded into testing plaques and bars as described above. The formulation information for Examples P19 to P24 and Comparative Example CP4 is listed in Table P10. The peak polymer recrystallization temperature, bi-directional modulus, Izod impact, and heat deflection temperature were measured and reported in Table P11 and P12 below.

TABLE P10

Formulation information for Samples CP4 and P19 to P24. All the compositions contain 500 ppm of Irganox 1010, 1000 ppm of Irgafos 168, and 500 ppm of DHT-4A.

| Examples | Additives | | | | | |
|---|---|---|---|---|---|---|
| | EX5 | EX46 | EX9 | EX8 | EX36 | EX76 |
| CP4 | 0 | 0 | 0 | 0 | 0 | 0 |
| P19 | 2000 ppm | 0 | 0 | 0 | 0 | 0 |
| P20 | 0 | 2000 ppm | 0 | 0 | 0 | 0 |
| P21 | 0 | 0 | 2000 ppm | 0 | 0 | 0 |
| P22 | 0 | 0 | 0 | 2000 ppm | 0 | 0 |
| P23 | 0 | 0 | 0 | 0 | 2000 ppm | 0 |
| P24 | 0 | 0 | 0 | 0 | 0 | 2000 ppm |

TABLE P11

Bi-directional modulus of comparative example CP4 and examples P19 to P24

| | Property Bi-directional Modulus | | | |
|---|---|---|---|---|
| Sample | Machine Direction (MPa) | Std Dev (MPa) | Transverse Direction (MPa) | Std Dev (MPa) |
| CP4 | 1205 | 12 | 1155 | 11 |
| P19 | 1353 | 4 | 1298 | 4 |
| P20 | 1343 | 11 | 1280 | 9 |
| P21 | 1340 | 9 | 1297 | 6 |
| P22 | 1349 | 19 | 1300 | 15 |
| P23 | 1311 | 10 | 1271 | 18 |
| P24 | 1335 | 8 | 1217 | 9 |

TABLE P12

Peak polymer recrystallization temperature, and heat deflection temperature of comparative example CP4 and examples P19 to P24

| | Property | | | |
|---|---|---|---|---|
| Sample | $T_c$ (° C.) | Izod Impact (J/m) | Std Dev (J/m) | Heat Deflection temperature (° C.) |
| CP4 | 120.8 | 99.6 | 5.3 | 83 |
| P19 | 128.9 | 82.5 | 7.6 | 101 |
| P20 | 128.1 | 90.8 | 11.3 | 100 |
| P21 | 128.7 | 92.3 | 6.1 | 96 |
| P22 | 132.7 | 83.5 | 4.9 | 99 |
| P23 | 132.8 | 84.8 | 5.7 | 100 |
| P24 | 131.3 | 84.9 | 12.1 | 98 |

Manufacture of Nucleated Polyethylene by Injection Molding

In the following injection molding examples, the polyethylene resins were prepared as described above in connection with the preceding injection molding examples. Plaques and bars were formed through injection molding on an Arburg 40 ton injection molder with a 25.4 mm diameter screw. The barrel temperature of the injection molder was between 190 and 230° C. depending on the melt index of the resin and the mold temperature was controlled at 25° C.

Unless otherwise specified, the injection speed for the plaques was 15 cc/sec, and their dimensions were about 60 mm long, 60 mm wide and 2 mm thick. These plaques were used to measure bi-directional shrinkage, recrystallization temperature, and bi-directional stiffness.

Unless otherwise specified, the injection speed for the bars was 40 cc/sec, and their dimensions were about 127 mm long, 12.7 mm wide and 3.3 mm thick. These bars were used to measure 1% secant modulus and HDT.

Testing of Nucleated Polyethylene

Shrinkage is measured in the plaques, in both the machine direction (MD) and the transverse direction (TD), after 48 hours aging at ambient conditions according to ASTM D955. The percent shrinkage for each direction is calculated using the following equation:

$$\left(\frac{\text{Mold Dimension} - \text{Test Specimen Dimension}}{\text{Mold Dimension}}\right) \times 100\%$$

Flexural properties testing (reported as bi-directional modulus) was performed on the above mentioned plaques using an MTS Q-Test-5 instrument with a span of 32 mm, a fixed deflection rate of 8.53 mm/minute, and a nominal sample width of 50.8 mm. Samples were prepared by cutting square sections (approximately 50 mm×50 mm) from the centers of the plaques in order to obtain an isotropically sized sample. In addition to testing the samples across the machine/flow direction as is customary (labeled as "Transverse Direction" in the results table), samples were also tested by flexing across the direction perpendicular to the flow direction to measure stiffness in that direction (labeled as "Machine Direction" in the results table) in order to examine the bi-directional stiffness of the plaques.

The peak polymer recrystallization temperature ($T_c$) for the thermoplastic polymer compositions was measured using a differential scanning calorimeter (Mettler-Toledo DSC822 differential scanning calorimeter). In particular, a sample was taken from the target part and heated at a rate of 20° C./minute from a temperature of 60° C. to 220° C., held at 220° C. for two minutes, and cooled at a rate of approximately 10°

C./minute to a temperature of 60° C. The temperature at which peak polymer crystal reformation occurred (which corresponds to the peak polymer recrystallization temperature) was recorded for each sample.

EXAMPLES Q1-012

These examples demonstrate some of the physical properties exhibited by a high density polyethylene polymer that has been nucleated with a blend of EX76 and an acid scavenger, specifically zinc stearate (ZnSt) or a synthetic dihydrotalcite compound (DHT-4A). Polymer compositions were prepared by compounding (as described above) Preparation Example EX76 and different acid scavengers into a commercially available high density polyethylene (Nova Sclair® 19G) having a density of approximately 0.960 g/cm$^3$ and a melt flow index of approximately 1.2 dg/minute. The resin was first ground, mixed with the additives, and then compounded and extruded to form pellets. The formed polymer composition pellet was then injection molded into testing plaques and bars.

The formulation information for Examples Q1 to Q12 and Comparative Example CQ1 is listed in table Q1. The peak polymer recrystallization temperature (Tc), bi-directional modulus (measured on plaques), and 1% secant modulus and heat deflection temperature (measured on bars) are reported in Tables Q2 and Q3 below.

TABLE Q1

Formulation information for Samples CQ1 and Q1 to Q12.

| | Additives | | |
|---|---|---|---|
| Examples | EX76 | DHT-4A | ZnSt |
| CQ1 | None | None | None |
| Q1 | 500 ppm | None | None |
| Q2 | 375 ppm | 125 ppm | None |
| Q3 | 375 ppm | None | 125 ppm |
| Q4 | 1000 ppm | None | None |
| Q5 | 750 ppm | 250 ppm | None |
| Q6 | 750 ppm | None | 250 ppm |
| Q7 | 1500 ppm | None | None |
| Q8 | 1125 ppm | 375 ppm | None |
| Q9 | 1125 ppm | None | 375 ppm |
| Q10 | 2000 ppm | None | None |
| Q11 | 1500 ppm | 500 ppm | None |
| Q12 | 1500 ppm | None | 500 ppm |

TABLE Q2

Bi-directional modulus and bi-directional shrinkage of samples CQ1 and Q1 to Q12.

| | Property | | | | | |
|---|---|---|---|---|---|---|
| | Bi-directional Modulus | | | | Bi-directional Shrinkage | |
| Sample | Machine Direction (MPa) | Std Dev (MPa) | Transverse Direction (MPa) | Std Dev (MPa) | Machine Direction (MPa) | Transverse Direction (MPa) |
| CQ1 | 1085 | 14 | 1282 | 29 | 2.17 | 1.54 |
| Q1 | 1016 | 6 | 1353 | 3 | 1.28 | 0.81 |
| Q2 | 1042 | 8 | 1343 | 6 | 1.2 | 0.93 |
| Q3 | 1197 | 12 | 1394 | 8 | 0.83 | 1.27 |
| Q4 | 1057 | 3 | 1336 | 3 | 1.07 | 0.92 |
| Q5 | 1081 | 7 | 1354 | 10 | 1.09 | 0.99 |
| Q6 | 1247 | 14 | 1313 | 7 | 0.65 | 1.48 |
| Q7 | 1067 | 4 | 1329 | 9 | 1.05 | 0.96 |
| Q8 | 1108 | 14 | 1334 | 7 | 1.03 | 1.06 |
| Q9 | 1271 | 5 | 1278 | 5 | 0.6 | 1.54 |
| Q10 | 1086 | 11 | 1322 | 12 | 1.02 | 1.01 |
| Q11 | 1118 | 15 | 1336 | 7 | 0.95 | 1.16 |
| Q12 | 1298 | 11 | 1292 | 3 | 0.54 | 1.55 |

EX76 without ZnSt or DHT-4A imparts some machine direction (MD) crystal growth orientation as evidenced by the decrease in MD shrinkage. When DHT-4A is used as the acid scavenger at a 3:1 ratio of EX76 to DHT-4A, a stronger MD orientation (lower MD than TD shrinkage) is present at loadings of 1,500 ppm of the blend. When ZnSt is used as the acid scavenger, the strong MD orientation is apparent at loadings of the blend as low as 500 ppm. This is evident from the lower MD shrinkage, the higher MD stiffness, and a decrease in the TD stiffness.

TABLE Q3

1% secant modulus, heat deflection temperature, and peak polymer recrystallization temperature of CQ1 and Q1 to Q12.

| | Property | | | |
|---|---|---|---|---|
| Sample | 1% Secant Modulus (MPa) | Std Dev (MPa) | Heat Deflection temperature (° C.) | $T_c$ (° C.) |
| CQ1 | 982.4 | 0.9 | 59.70 | 117.17 |
| Q1 | 1121.7 | 1.2 | 67.80 | 119.17 |
| Q2 | 1133.6 | 1.1 | 69.00 | 119.00 |
| Q3 | 1221.9 | 2.1 | 78.30 | 118.67 |
| Q4 | 1155.3 | 1.9 | 68.10 | 118.83 |
| Q5 | 1162.2 | 3.1 | 70.50 | 119.00 |
| Q6 | 1312.2 | 0.7 | 85.70 | 119.00 |
| Q7 | 1182.4 | 3.4 | 71.90 | 119.00 |
| Q8 | 1189.1 | 0.4 | 75.10 | 119.17 |
| Q9 | 1376.3 | 1.1 | 91.00 | 119.00 |
| Q10 | 1203.8 | 0.7 | 74.50 | 119.33 |
| Q11 | 1214.2 | 1.1 | 75.30 | 119.33 |
| Q12 | 1416.4 | 3 | 93.40 | 118.83 |

As can be seen from Table Q3, the blends of EX76 with an acid scavenger had the same effect on the $T_c$ as EX76 alone. The stiffness measurements and HDT in flex bars confirmed that using EX76 together with ZnSt or DHT-4A significantly improves the performance of EX76 as compared to EX76 alone. When a blend of the nucleating agent and acid scavenger are used, lower loadings of the nucleating agent (EX76) are able to impart similar or better properties than higher loadings of EX76 alone.

EXAMPLES R1-R9

These examples demonstrate some of the physical properties exhibited by a high density polyethylene polymer that has been nucleated with blends of EX76 and ZnSt at different ratios. Polymer compositions were prepared by compounding (as described above) Preparation Example EX76 and ZnSt into a commercially available high density polyethylene (Nova Sclair® 19G) having a density of approximately 0.960 g/cm$^3$ and a melt flow index of approximately 1.2 dg/minute.

The resin was first ground, mixed with the additives, and then compounded and extruded to form pellets. The formed polymer composition pellet was then injection molded into testing plaques and bars.

The formulation information for Examples R1 to R9 and Comparative Examples CR1 and CR2 are listed in table R1. The peak polymer recrystallization temperature ($T_c$), bi-directional modulus (measured on plaques), and 1% secant modulus and heat deflection temperature (measured on bars) are reported in Tables R2 and R3 below.

TABLE R1

Formulation information for Samples CR1, CR2, and R1 to R9.

| Examples | Additives | |
|---|---|---|
| | EX76 | ZnSt |
| CR1 | None | None |
| CR2 | None | 1000 ppm |
| R1 | 1000 ppm | None |
| R2 | 2000 ppm | None |
| R3 | 875 ppm | 125 ppm |
| R4 | 750 ppm | 250 ppm |
| R5 | 667 ppm | 333 ppm |
| R6 | 500 ppm | 500 ppm |
| R7 | 333 ppm | 667 ppm |
| R8 | 250 ppm | 750 ppm |
| R9 | 125 ppm | 875 ppm |

TABLE R2

Bi-directional modulus and bi-directional shrinkage of samples CR1, CR2, and R1 to R9.

| Sample | Bi-directional Modulus | | | | Bi-directional Shrinkage | |
|---|---|---|---|---|---|---|
| | Machine Direction (MPa) | Std Dev (MPa) | Transverse Direction (MPa) | Std Dev (MPa) | Machine Direction (MPa) | Transverse Direction (MPa) |
| CR1 | 1168 | 7.6 | 1382 | 8.4 | 2.11 | 1.33 |
| CR2 | 1164 | 9.3 | 1375 | 4 | 2.13 | 1.32 |
| R1 | 1140 | 6.6 | 1525 | 8.7 | 1.14 | 0.57 |
| R2 | 1201 | 8.2 | 1483 | 1.9 | 0.95 | 0.65 |
| R3 | 1297 | 4.8 | 1338 | 6.4 | 0.59 | 1.05 |
| R4 | 1301 | 6.1 | 1294 | 7.5 | 0.51 | 1.16 |
| R5 | 1286 | 5.6 | 1253 | 2.6 | 0.49 | 1.22 |
| R6 | 1287 | 6.7 | 1289 | 9.1 | 0.57 | 1.24 |
| R7 | 1237 | 1.6 | 1284 | 8.2 | 0.72 | 1.18 |
| R8 | 1221 | 8.4 | 1309 | 11.8 | 0.79 | 1.12 |
| R9 | 1214 | 3.6 | 1342 | 6.8 | 1.01 | 1.07 |

The data for Sample CR2 show that the addition of ZnSt alone does not have a significant effect on the bi-directional stiffness or the shrinkage of this resin. This is evidence that the ZnSt does not nucleate the resin. Samples R1 and R2 show that EX76 without ZnSt imparts MD crystal growth orientation (decreasing the MD shrinkage compared to CR1 and CR2). When ZnSt is used together with EX76, a much stronger MD orientation (very low MD shrinkage) is observed. This is true even with a 1:4 ratio blend, where EX76 is only present at 125 ppm in the resin.

When EX76 and ZnSt are used together, a very high MD stiffness and a decrease in the TD stiffness are observed, which is indicative of a very strong MD orientation. The MD stiffness imparted by all of the blends is higher than the MD stiffness of EX76 alone at both 1,000 ppm and 2,000 ppm. This is surprising since the resins compounded with the blends contain less EX76. The highest MD stiffness is obtained with blends of EX76 and ZnSt having ratios ranging from 4:1, 3:1, 2:1 and 1:1. But even at ratios of 1:3 and 1:4 (which refer to EX76 loadings of 250 ppm and 125 ppm, with ZnSt at 750 ppm and 875 ppm respectively), MD stiffness is similar or slightly higher than EX76 alone at 2,000 ppm.

TABLE R3

1% secant modulus, heat deflection temperature, and peak polymer recrystallization temperature of CR1, CR2, and R1 to R9.

| Sample | Property | | | |
|---|---|---|---|---|
| | 1% Secant Modulus (MPa) | Std Dev (MPa) | Heat Deflection temperature (° C.) | $T_c$ (° C.) |
| CR1 | 889 | 21.9 | 62.20 | 116.33 |
| CR2 | 882 | 7 | 61.70 | 116.33 |
| R1 | 1070 | 6.2 | 67.40 | 118.50 |
| R2 | 1073 | 5.6 | 74.10 | 118.17 |
| R3 | 1164 | 6.3 | 84.50 | 118.17 |
| R4 | 1182 | 9.1 | 86.90 | 118.17 |
| R5 | 1195 | 4.2 | 85.00 | 118.00 |
| R6 | 1173 | 8 | 86.20 | 118.33 |
| R7 | 1115 | 6.5 | 81.60 | 118.17 |
| R8 | 1077 | 15.6 | 77.30 | 117.83 |
| R9 | 1049 | 9.9 | 74.20 | 117.67 |

As can be seen from the data in Table R3, EX76 increased the $T_c$ of the resin. The different blends of EX76 with ZnSt did not improve the $T_c$ over that observed with EX76 alone. Indeed, the $T_c$ decreased slightly as the amount of EX76 decreased.

The stiffness measurements and HDT in flex bars confirmed the synergy between EX76 and ZnSt. The blends having ratios of 4:1, 3:1, 2:1, 1:1 and 1:2 (EX76:ZnSt) imparted much higher stiffness and HDT than EX76 alone. And the blends of EX76 with ZnSt at ratios of 1:3 and 1:4 imparted stiffness and HDT values similar to those of EX76 alone. This means that one could use a resin containing a blend of EX76 at 125 ppm and ZnSt at 875 ppm and still obtain similar performance to a resin containing EX76 alone at 2,000 ppm.

EXAMPLES S1-S5

These examples demonstrate some of the physical properties exhibited by a high density polyethylene polymer that has been nucleated with blends of EX76 and ZnSt at different ratios. Polymer compositions were prepared by compounding (as described above) Preparation Example EX76 and different acid scavengers into a commercially available high density polyethylene (Dow HDPE DMDA-8007 NT7) having a density of approximately 0.967 g/cm$^3$ and a melt flow index of approximately 8.3 dg/minute. The resin was first ground, mixed with the additives, and then compounded and extruded to form pellets. The formed polymer composition pellet was then injection molded into testing plaques and bars.

The formulation information for Examples S1 to S5 and Comparative Example CS1 and CS2 are listed in table S1. The peak polymer recrystallization temperature ($T_c$), bi-directional modulus (measured on plaques), and 1% secant modulus and heat deflection temperature (measured on bars) are reported in Tables S2 and S3 below.

TABLE S1

Formulation information for Samples CS1, CS2, and S1 to S5.

| | Additives | |
|---|---|---|
| Examples | EX76 | ZnSt |
| CS1 | None | None |
| CS2 | None | 1000 ppm |
| S1 | 1000 ppm | None |
| S2 | 2000 ppm | None |
| S3 | 875 ppm | 125 ppm |
| S4 | 750 ppm | 250 ppm |
| S5 | 667 ppm | 333 ppm |

TABLE S2

Bi-directional modulus and bi-directional shrinkage of samples CS1, CS2, and S1 to S5.

| | Property | | | | | |
|---|---|---|---|---|---|---|
| | Bi-directional Modulus | | | | Bi-directional Shrinkage | |
| Sample | Machine Direction (MPa) | Std Dev (MPa) | Transverse Direction (MPa) | Std Dev (MPa) | Machine Direction (MPa) | Transverse Direction (MPa) |
| CS1 | 1146 | 10.8 | 1233 | 19.0 | 1.96 | 1.75 |
| CS2 | 1114 | 12.6 | 1212 | 10.2 | 1.98 | 1.74 |
| S1 | 1127 | 18.4 | 1302 | 15.6 | 0.90 | 0.90 |
| S2 | 1194 | 7.0 | 1340 | 5.2 | 0.87 | 0.94 |
| S3 | 1301 | 15.1 | 1234 | 19.1 | 0.58 | 1.23 |
| S4 | 1286 | 16.5 | 1187 | 18.0 | 0.57 | 1.25 |
| S5 | 1238 | 11.5 | 1192 | 8.9 | 0.57 | 1.26 |

The data for Sample CS2 show that the addition of ZnSt alone does not have a significant effect on the bi-directional stiffness or the shrinkage of this resin. These observations confirm that the ZnSt does not nucleate the resin. The data for Samples S1 and S2 show that EX76 alone imparts MD crystal growth orientation (decreasing the MD shrinkage compared to CS1 and CS2). When ZnSt and EX76 are used together, a much stronger MD orientation (very low MD shrinkage) is observed. This is true for all of the blend ratios tested.

When a blend of EX76 and ZnSt is used, a very high MD stiffness and a decrease in the TD stiffness are observed, which is indicative of a very strong MD orientation. The MD stiffness imparted by any of the blends at a total loading of 1,000 ppm is higher than that imparted by EX76 alone, even at a loading of 2,000 ppm. These results are consistent with those observed with lower melt flow index polyethylene resins.

TABLE S3

1% secant modulus, heat deflection temperature, and peak polymer recrystallization temperature of CS1, CS2, and S1 to S5.

| | Property | | | |
|---|---|---|---|---|
| Sample | 1% Secant Modulus (MPa) | Std Dev (MPa) | Heat Deflection temperature (° C.) | $T_c$ (° C.) |
| CS1 | 958 | 5.2 | 66.50 | 116.67 |
| CS2 | 940 | 3.8 | 64.60 | 117.67 |
| S1 | 1137 | 7.8 | 77.60 | 120.33 |
| S2 | 1227 | 14.2 | 82.00 | 120.67 |
| S3 | 1328 | 15.3 | 90.10 | 120.17 |
| S4 | 1322 | 6.1 | 89.00 | 120.00 |
| S5 | 1288 | 4.6 | 88.40 | 120.50 |

As can be seen from the data in Table S3, EX76 increased the $T_c$ of the resin. The different blends of EX76 with ZnSt did not improve the $T_c$ over that observed with EX76 alone. In fact, the $T_c$ slightly decreased as the amount of EX76 decreased.

The stiffness measurements and HDT in flex bars confirmed the synergy between EX76 and ZnSt. The blends at ratios of 3:1, 2:1 and 1:1 (EX76:ZnSt) imparted much higher stiffness and HDT values than EX76 alone.

EXAMPLES T1-T5

These examples demonstrate some of the physical properties exhibited by a high density polyethylene polymer that has been nucleated with blends of EX76 and ZnSt at different ratios. Polymer compositions were prepared by compounding (as described above) Preparation Example EX76 and different acid scavengers into a commercially available high density polyethylene (Dowlex™ IP40) having a density of approximately 0.952 g/cm³ and a melt flow index of approximately 40 dg/minute. The resin was first ground, mixed with the additives, and then compounded and extruded to form pellets. The formed polymer composition pellet was then injection molded into testing plaques and bars.

The formulation information for Examples T1 to T5 and Comparative Example CT1 and CT2 are listed in table T1. The peak polymer recrystallization temperature ($T_c$), bi-directional modulus (measured on plaques), and 1% secant modulus and heat deflection temperature (measured on bars) are reported in Tables T2 and T3 below.

TABLE T1

Formulation information for Samples CT1, CT2, and T1 to T5.

| | Additives | |
|---|---|---|
| Examples | EX76 | ZnSt |
| CT1 | None | None |
| CT2 | None | 1000 ppm |
| T1 | 1000 ppm | None |
| T2 | 2000 ppm | None |
| T3 | 875 ppm | 125 ppm |
| T4 | 750 ppm | 250 ppm |
| T5 | 667 ppm | 333 ppm |

TABLE T2

Bi-directional modulus and bi-directional shrinkage of samples CT1, CT2, and T1 to T5.

| | Property | | | | | |
|---|---|---|---|---|---|---|
| | Bi-directional Modulus | | | | Bi-directional Shrinkage | |
| Sample | Machine Direction (MPa) | Std Dev (MPa) | Transverse Direction (MPa) | Std Dev (MPa) | Machine Direction (MPa) | Transverse Direction (MPa) |
| CT1 | 896 | 4.2 | 921 | 5.3 | 1.78 | 1.63 |
| CT2 | 910 | 4.9 | 931 | 5.5 | 1.79 | 1.64 |
| T1 | 926 | 1.3 | 985 | 3.1 | 1.41 | 1.28 |
| T2 | 946 | 1.0 | 970 | 2.8 | 0.95 | 1.00 |
| T3 | 967 | 3.3 | 959 | 4.0 | 1.10 | 1.29 |
| T4 | 1006 | 0.5 | 934 | 0.6 | 0.91 | 1.39 |
| T5 | 1044 | 3.7 | 906 | 2.5 | 0.81 | 1.46 |

The data for Sample CT2 shows that the addition of ZnSt alone does not have a significant effect on the bi-directional stiffness or the shrinkage of this resin. This is evidence that the ZnSt does not nucleate the resin. Samples T1 and T2 show that EX76 alone imparts MD crystal growth orientation (decreasing the MD shrinkage compared to CT1 and CT2). When both ZnSt and EX76 are used together, a much stronger MD orientation (very low MD shrinkage) is present. This is true for all of the different blend ratios tested.

When EX76 and ZnSt are used together, a very high MD stiffness and a decrease in the TD stiffness are observed, which is indicative of a very strong MD orientation. The MD stiffness imparted by all of the blends is higher than the MD stiffness of EX76 alone at loadings of 1,000 and 2,000 ppm. These results are consistent with those observed with other HDPE resins.

TABLE T3

1% secant modulus, heat deflection temperature, and peak polymer recrystallization temperature ($T_c$) of CT1, CT2, and T1 to T5.

| Sample | 1% Secant Modulus (MPa) | Std Dev (MPa) | Heat Deflection temperature (° C.) | $T_c$ (° C.) |
|---|---|---|---|---|
| CT1 | 753 | 9.6 | 62.30 | 114.83 |
| CT2 | 768 | 9.2 | 62.10 | 114.67 |
| T1 | 845 | 9 | 66.40 | 116.17 |
| T2 | 943 | 1.5 | 74.30 | 116.67 |
| T3 | 892 | 6.6 | 73.10 | 116.50 |
| T4 | 961 | 8.7 | 79.30 | 115.83 |
| T5 | 996 | 10 | 80.70 | 115.67 |

As can be seen from the data in Table T3, EX76 increased the $T_c$ of the resin. The different blends of EX76 with ZnSt did not improve the $T_c$ over that observed with EX76 alone.

The stiffness measurement and HDT in flex bars confirm the synergy between EX76 and ZnSt. The blends having ratios of 3:1, 2:1 and 1:1 imparted much higher stiffness and HDT values than EX76 alone.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A compound of Formula (C)

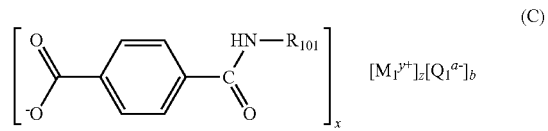

wherein $R_{101}$ is selected from the group consisting of a cyclopentyl group and moieties of Formula (CI); Formula (CI) is

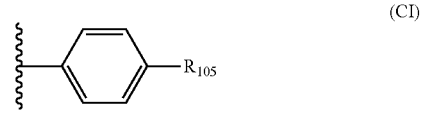

$R_{105}$ is selected from the group consisting of hydrogen and halogens; x is a positive integer; each $M_1$ is a metal cation; y is the valence of the cation; z is a positive integer; b is zero or a positive integer; when b is a positive integer, each $Q_1$ is a negatively-charged counterion and a is the valence of the negatively-charged counterion; and the values of x, y, z, a, and b satisfy the equation x+(ab)=yz.

2. The compound of claim 1, wherein $M_1$ is a cation of a metal selected from the group consisting of alkali metals and alkaline earth metals.

3. The compound of claim 2, wherein $M_1$ is a cation of a metal selected from the group consisting of alkali metals.

4. The compound of claim 3, wherein $M_1$ is a lithium cation.

5. The compound of claim 1, wherein $R_{101}$ is a cyclopentyl group.

6. The compound of claim 5, wherein x is 1, $M_1$ is a lithium cation, y is 1, z is 1, and b is zero.

7. The compound of claim 1, wherein $R_{101}$ is a moiety conforming to the structure of Formula (CI).

8. The compound of claim 7, wherein $R_{105}$ is hydrogen.

9. The compound of claim 8, wherein x is 1, $M_1$ is a lithium cation, y is 1, z is 1, and b is zero.

10. The compound of claim 7, wherein $R_{105}$ is a halogen.

11. The compound of claim 10, wherein $R_{105}$ is bromine.

12. The compound of claim 11, wherein x is 1, $M_1$ is a lithium cation, y is 1, z is 1, and b is zero.

13. A composition comprising a polyolefin polymer and the compound of claim 1.

14. A composition comprising a polyolefin polymer and the compound of claim 4.

15. A composition comprising a polyolefin polymer and the compound of claim 6.

16. A composition comprising a polyolefin polymer and the compound of claim 7.

17. A composition comprising a polyolefin polymer and the compound of claim 9.

18. A composition comprising a polyolefin polymer and the compound of claim 10.

19. A composition comprising a polyolefin polymer and the compound of claim 12.

* * * * *